US009499810B2

(12) United States Patent
Belani et al.

(10) Patent No.: US 9,499,810 B2

(45) Date of Patent: Nov. 22, 2016

(54) THROMBOPOIETIC ACTIVITY OF TYROSYL-TRNA SYNTHETASE POLYPEPTIDES

(71) Applicant: aTyr Pharma, Inc., San Diego, CA (US)

(72) Inventors: Rajesh Belani, San Diego, CA (US); Jeffry Dean Watkins, Encinitas, CA (US); Wei Zhang, San Diego, CA (US); Alain Phillippe Vasserot, Carlsbad, CA (US)

(73) Assignee: aTyr Pharma, Inc., San Diego, CA (US)

(*) Notice: Subject to any disclaimer, the term of this patent is extended or adjusted under 35 U.S.C. 154(b) by 0 days.

(21) Appl. No.: 14/180,126

(22) Filed: Feb. 13, 2014

(65) Prior Publication Data

US 2014/0255375 A1 Sep. 11, 2014

Related U.S. Application Data

(63) Continuation of application No. 12/482,151, filed on Jun. 10, 2009, now abandoned.

(60) Provisional application No. 61/060,747, filed on Jun. 11, 2008.

(51) Int. Cl.

| | |
|---|---|
| ***A61K 38/54*** | (2006.01) |
| ***A61K 38/00*** | (2006.01) |
| ***C07K 1/00*** | (2006.01) |
| ***C12N 9/00*** | (2006.01) |
| ***A61K 38/53*** | (2006.01) |
| ***C12N 9/96*** | (2006.01) |

(52) U.S. Cl.

CPC ................. *C12N 9/93* (2013.01); *A61K 38/53* (2013.01); *C12N 9/96* (2013.01)

(58) Field of Classification Search

CPC ........... A61K 38/53; A61K 9/93; A61K 9/96

USPC ................................ 424/94.3, 94.5; 530/350

See application file for complete search history.

(56) References Cited

U.S. PATENT DOCUMENTS

| | | | | |
|---|---|---|---|---|
| 6,013,483 | A | 1/2000 | Coleman et al. | |
| 6,225,060 | B1 | 5/2001 | Clark et al. | |
| 6,428,960 | B1 | 8/2002 | Clark et al. | |
| 6,548,060 | B1 | 4/2003 | Kim | |
| 6,864,226 | B1 | 3/2005 | Coleman et al. | |
| 6,903,189 | B2 * | 6/2005 | Schimmel et al. | 530/350 |
| 7,045,301 | B2 | 5/2006 | Coleman et al. | |
| 7,067,126 | B2 | 6/2006 | Schimmel et al. | |
| 7,144,984 | B2 | 12/2006 | Schimmel et al. | |
| 7,196,068 | B2 | 3/2007 | Kim et al. | |
| 7,273,844 | B2 | 9/2007 | Schimmel et al. | |
| 7,413,885 | B2 | 8/2008 | Schimmel et al. | |
| 7,459,529 | B2 | 12/2008 | Kim | |
| 7,476,651 | B2 | 1/2009 | Schimmel et al. | |
| 7,482,326 | B2 | 1/2009 | Coleman et al. | |
| 7,521,215 | B2 | 4/2009 | Schimmel et al. | |
| 7,528,106 | B2 | 5/2009 | Friedlander et al. | |
| 7,901,917 | B2 | 3/2011 | Schimmel et al. | |
| 7,902,165 | B2 | 3/2011 | Kim | |
| 8,003,780 | B2 | 8/2011 | Kim et al. | |
| 8,017,593 | B2 | 9/2011 | Schimmel et al. | |
| 8,026,088 | B2 * | 9/2011 | Yang | 435/183 |
| 8,101,566 | B2 | 1/2012 | Schimmel et al. | |
| 8,148,125 | B2 | 4/2012 | Schimmel et al. | |
| 2002/0182666 | A1 | 12/2002 | Schimmel et al. | |
| 2003/0017564 | A1 | 1/2003 | Schimmel et al. | |
| 2003/0215827 | A1 | 11/2003 | Yue et al. | |
| 2004/0018505 | A1 | 1/2004 | Lee et al. | |
| 2004/0048290 | A1 | 3/2004 | Lee et al. | |
| 2004/0101879 | A1 | 5/2004 | Seidel-Dugan et al. | |
| 2004/0152079 | A1 | 8/2004 | Schimmel et al. | |
| 2006/0024288 | A1 | 2/2006 | Glidden | |
| 2006/0046250 | A1 | 3/2006 | Kim | |
| 2006/0078553 | A1 | 4/2006 | Glidden | |
| 2007/0048322 | A1 | 3/2007 | Schimmel et al. | |
| 2007/0061916 | A1 | 3/2007 | Kovalic et al. | |
| 2007/0111238 | A1 | 5/2007 | Jamieson et al. | |
| 2009/0227662 | A1 | 9/2009 | Schimmel et al. | |
| 2009/0285792 | A1 | 11/2009 | Friedlander et al. | |
| 2010/0003230 | A1 | 1/2010 | Glidden | |
| 2010/0028352 | A1 | 2/2010 | Greene et al. | |
| 2010/0092434 | A1 | 4/2010 | Belani et al. | |
| 2010/0138941 | A1 | 6/2010 | Kim et al. | |

(Continued)

FOREIGN PATENT DOCUMENTS

| | | |
|---|---|---|
| CN | 1341725 | 3/2002 |
| CN | 1341727 | 3/2002 |

(Continued)

OTHER PUBLICATIONS

Broun et al., Catalytic plasticity of fatty acid modification enzymes underlying chemical diversity of plant lipids. Science, 1998, vol. 282: 1315-1317.*

Chica et al., Semi-rational approaches to engineering enzyme activity: combining the benefits of directed evolution and rational design. Curr. Opi. Biotechnol., 2005, vol. 16: 378-384.*

Devos et al., Practical limits of function prediction. Proteins: Structure, Function, and Genetics. 2000, vol. 41: 98-107.*

Quinn et al., Species-specific microhelix aminoacylation by a eukaryotic pathogen tRNA synthetase dependent on a single base pair. Biochemistry, 1995, vol. 34 (39): 12489-12495.*

Seffernick et al., Melamine deaminase and Atrazine chlorohydrolase: 98 percent identical but functionally different. J. Bacteriol., 2001, vol. 183 (8): 2405-2410.*

Sen et al., Developments in directed evolution for improving enzyme functions. Appl. Biochem. Biotechnol., 2007, vol. 143: 212-223.*

Whisstock et al., Prediction of protein function from protein sequence. Q. Rev. Biophysics., 2003, vol. 36 (3): 307-340.*

(Continued)

*Primary Examiner* — Ganapathirama Raghu

(74) *Attorney, Agent, or Firm* — Cooley LLP

(57) ABSTRACT

Thrombopoietic compositions are provided comprising tyrosyl tRNA synthetase polypeptides, including truncations and/or variants thereof. Also provided are methods of using such compositions in the treatment of conditions that benefit from increased thrombopoiesis, such as thrombocytopenia.

10 Claims, 29 Drawing Sheets

(56) References Cited

U.S. PATENT DOCUMENTS

| | | | |
|---|---|---|---|
| 2010/0297149 A1 | 11/2010 | Zhou et al. | |
| 2010/0310576 A1 | 12/2010 | Adams et al. | |
| 2011/0110917 A1 | 5/2011 | Schimmel et al. | |
| 2011/0117572 A1 | 5/2011 | Kim et al. | |
| 2011/0136119 A1 | 6/2011 | Kim et al. | |
| 2011/0150885 A1 | 6/2011 | Watkins et al. | |
| 2011/0189195 A1 | 8/2011 | Kim et al. | |
| 2011/0250701 A1 | 10/2011 | Kim et al. | |
| 2011/0256119 A1 | 10/2011 | Kim et al. | |
| 2012/0004185 A1 | 1/2012 | Greene | |
| 2012/0015383 A1 | 1/2012 | Park et al. | |
| 2012/0058133 A1 | 3/2012 | Whitman et al. | |
| 2012/0064082 A1 | 3/2012 | Watkins et al. | |

FOREIGN PATENT DOCUMENTS

| | | | |
|---|---|---|---|
| CN | 1352242 | 6/2002 | |
| CN | 1352252 | 6/2002 | |
| EP | 0893494 | 1/1999 | |
| EP | 0893496 | 1/1999 | |
| EP | 0897004 | 2/1999 | |
| EP | 1275720 | 1/2003 | |
| EP | 1300468 | 4/2003 | |
| EP | 1377305 | 1/2009 | |
| EP | 1776138 | 10/2009 | |
| EP | 1274834 | 7/2010 | |
| JP | 2003-529354 | 10/2003 | |
| JP | 2004-516009 | 6/2004 | |
| JP | 2005-523682 | 8/2005 | |
| WO | WO 97/26351 | 7/1997 | |
| WO | WO 97/39017 | 10/1997 | |
| WO | WO 99/45130 | 9/1999 | |
| WO | WO 01/74841 | 10/2001 | |
| WO | WO 01/75078 | 10/2001 | |
| WO | WO 01/90330 | 11/2001 | |
| WO | WO 01/94568 | 12/2001 | |
| WO | WO 02/04611 | 1/2002 | |
| WO | WO 02/055663 | 7/2002 | |
| WO | WO 02/059323 | 8/2002 | |
| WO | WO 02/067970 | 9/2002 | |
| WO | WO 03/009813 | 2/2003 | |
| WO | WO 03/031589 | 4/2003 | |
| WO | WO 03/072035 | 9/2003 | |
| WO | WO 03/080648 | 10/2003 | |
| WO | WO 03/094862 | 11/2003 | |
| WO | WO 2005/102395 | 11/2005 | |
| WO | WO 2005/117954 | 12/2005 | |
| WO | WO 2006/016217 | 2/2006 | |
| WO | WO 2006/057500 | 6/2006 | |
| WO | WO 2007/064941 A2 * | 7/2007 | ............... C12N 9/22 |
| WO | WO 2008/007818 | 1/2008 | |
| WO | WO 2008/016356 | 2/2008 | |
| WO | WO2008/067195 A2 * | 6/2008 | ............... C12Q 1/68 |
| WO | WO 2008/133359 | 11/2008 | |
| WO | WO 2009/114623 | 9/2009 | |
| WO | WO 2009/152247 | 12/2009 | |
| WO | WO 2009/158649 | 12/2009 | |
| WO | WO 2010/021415 | 2/2010 | |
| WO | WO 2010/041892 | 4/2010 | |
| WO | WO 2010/041913 | 4/2010 | |
| WO | WO 2010/090471 | 8/2010 | |
| WO | WO 2010/096170 | 8/2010 | |
| WO | WO 2010/099477 | 9/2010 | |
| WO | WO 2010/107825 | 9/2010 | |
| WO | WO 2010/120509 | 10/2010 | |
| WO | WO 2011/072265 | 6/2011 | |
| WO | WO 2011/072266 | 6/2011 | |
| WO | WO 2011/097031 | 8/2011 | |

OTHER PUBLICATIONS

Witkowski et al., Conversion of b-ketoacyl synthase to a Malonyl Decarboxylase by replacement of the active cysteine with glutamine. Biochemistry, 1999, vol. 38: 11643-11650.*

Office Action for European Application No. 09719533, mailed Mar. 28, 2011.

International Preliminary Report on Patentability for International Application No. PCT/US2009/036826, dated Sep. 14, 2010.

International Search Report and Written Opinion for International Application No. PCT/US2009/036826, mailed Oct. 15, 2009.

International Preliminary Report on Patentability for International Application No. PCT/US2009/048915, dated Jan. 5, 2011.

International Search Report and Written Opinion for International Application No. PCT/US2009/048915, mailed Nov. 2, 2009.

Office Action for U.S. Appl. No. 12/482,151, mailed Aug. 13, 2013.

Office Action for U.S. Appl. No. 12/482,151, mailed Oct. 11, 2011.

Office Action for U.S. Appl. No. 12/482,151, mailed Mar. 18, 2011.

International Preliminary Report on Patentability for International Application No. PCT/US2009/046910, dated Dec. 13, 2010.

International Search Report and Written Opinion for International Application No. PCT/US2009/046910, mailed Mar. 4, 2010.

Supplementary European Search Report for European Application No. 06838844.6, mailed Apr. 9, 2009.

Office Action for European Patent Application No. 06838844.6, mailed Apr. 9, 2009.

Office Action for U.S. Appl. No. 12/085,884, mailed Jan. 20, 2011.

Response to Office Action dated Apr. 18, 2011, for U.S. Appl. No. 12/085,884.

International Preliminary Report on Patentability for International Application No. PCT/US2006/046106, dated Jun. 4, 2008.

International Search Report and Written Opinion for International Application No. PCT/US2006/046106, mailed Aug. 9, 2007.

International Preliminary Report on Patentability for International Application No. PCT/US2010/025642, dated Aug. 30, 2011.

International Search Report and Written Opinion for International Application No. PCT/US2010/025642, mailed Oct. 29, 2010.

Office Action for U.S. Appl. No. 12/751,358, mailed Oct. 3, 2011.

Office Action for U.S. Appl. No. 12/751,358, mailed Mar. 3, 2011.

International Preliminary Report on Patentability for International Application No. PCT/US2010/029377, dated Oct. 4, 2011.

International Search Report and Written Opinion for International Application No. PCT/US2010/029377, mailed Jan. 26, 2011.

International Preliminary Report on Patentability for International Application No. PCT/US2010/027525, dated Sep. 20, 2011.

International Search Report and Written Opinion for International Application No. PCT/US2010/027525, mailed Jan. 10, 2011.

International Search Report and Written Opinion for International Application No. PCT/US2010/059964, mailed Aug. 25, 2011.

International Search Report and Written Opinion for International Application No. PCT/US2010/059963, mailed May 12, 2011.

International Search Report and Written Opinion for International Application No. PCT/US2011/000210, mailed Aug. 12, 2011.

Adams, M. D. et al., "The genome sequence of *Drosophila melanogaster*," Science, 287(5961):2185-2195 (2000).

Amaar, Y. G. et al., "Cloning and characterization of the C.elegans histidyl-tRNA synthetase gene," Nucleic Acids Research, 21(18):4344-4347 (1993).

Antonellis, A. et al., "Functional Analyses of Glycyl-tRNA Synthetase Mutations Suggest a Key Role for tRNA-Charging Enzymes in Peripheral Axons," The Journal of Neuroscience, 26(41):10397-10406 (2006).

BIOSIS (Biological Abstracts) Accession No. PREV200300183746, 2003.

BIOSIS (Biological Abstracts) Accession No. PREV200300256685, 2003.

BIOSIS (Biological Abstracts) Accession No. PREV200400442099, 2004.

BIOSIS (Biological Abstracts) Accession No. PREV200700042366, 2007.

BIOSIS (Biological Abstracts) Accession No. PREV200800526912, 2008.

Brown, M. V. et al., "Mammalian aminoacyl-tRNA synthetases: Cell signaling functions of the protein translation machinery," Vascular Pharmacology, 52(1-2):21-26 (2010).

(56) References Cited

OTHER PUBLICATIONS

Cheng, G. et al., "Effect of mini-tyrosyl-tRNA synthetase on ischemic angiogenesis, leukocyte recruitment, and vascular permeability," American Journal Physiol. Regul. Integr. Comp. Physiol., 295:R1138-R1146 (2008).
Copley, "Enzymes with extra talents: moonlighting functions and catalytic promiscuity," Current Opinion in Chemical Biology, 7:265-272 (2003).
DeBruyn et al., "Ex vivo Expansion of Megakaryocyte Progenitor Cells: Cord Blood Versus Mobilized Peripheral Blood," Stem Cells Development, 14:415-424 (2005).
Delgado, C. et al., "The uses and properties of PEG-linked proteins," Critical Reviews in Therapeutic Drug Carrier Systems, 9(3,4):249-304 (1992).
De Pouplana, L. R. et al., "Evidence that two present-day components needed for the genetic code appeared after nucleated cells separated from eubacteria," Proc. Natl. Acad. Sci. USA, 93:166-170 (1996).
Dessypris et al., "Thrombopoiesis-stimulating Factor: Its Effects on Megakaryocyte Colony Formation in vitro and Its Relation to Human Granulocyte-Macrophage Colony-stimulating Factor," Exp. Hematol. 18:754-757, 1990.
Ewalt, K. L. et al., "Activation of Angiogenic Signaling Pathways by Two Human tRNA Synthetases," Biochemistry, 41(45):13344-13349 (2002).
Froelich et al., "Dominant Intermediate Charcot-Marie-Tooth disorder is not due to a catalytic defect in tyrosyl-tRNA synthetase," Biochemistry, 59 pages (2011).
Frommhold, D. et al., "Sialyltransferase ST3Gal-IV controls CXCR2-mediated firm leukocyte arrest during inflammation," Journal of Experimental Medicine, 205(6):1435-1446 (2008).
GenBank Accession No. AI352487, Dec. 30, 1998.
GenBank Accession No. AI821854, Jul. 9, 1999.
GenBank Accession No. AJ706186, Jun. 30, 2004.
GenBank Accession No. AK125213, Jul. 3, 2008.
GenBank Accession No. AK126444, Jan. 9, 2008.
GenBank Accession No. AK127182, Jan. 9, 2008.
GenBank Accession No. AL043328, Jul. 8, 1999.
GenBank Accession No. BC001933, Jul. 15, 2006.
GenBank Accession No. BE561651, Aug. 10, 2000.
GenBank Accession No. BF205419, Nov. 3, 2000.
GenBank Accession No. BF308942, Nov. 20, 2000.
GenBank Accession No. BF876481, Jan. 17, 2001.
GenBank Accession No. BG165437, Feb. 5, 2001.
GenBank Accession No. BM917050, Mar. 11, 2002.
GenBank Accession No. BQ231273, May 1, 2002.
GenBank Accession No. BX440782, May 15, 2003.
GenBank Accession No. CX753411, Jan. 22, 2005.
GenBank Accession No. DA119890, Oct. 30, 2005.
GenBank Accession No. DA157534, Oct. 30, 2005.
GenBank Accession No. DA158736, Oct. 30, 2005.
GenBank Accession No. DA269700, Oct. 30, 2005.
GenBank Accession No. DA769799, Nov. 11, 2005.
GenBank Accession No. DA942238, Nov. 13, 2005.
GenBank Accession No. Q7QD89, Nov. 28, 2006.
GenBank Accession No. Q7QD89, Anopheles gambiae Sequence Committee, submitted Apr. 2002, [Retrieved from the Internet Apr. 24, 2007], <URL: http://www.ncbi.nlm.nih.gov/entrez/viewer.fcgi?db=protein&val=74803944>.
GenBank Accession No. Q9VV60, May 1, 2000.
GenBank Accession No. Q9VV60, Nov. 28, 2006.
GenBank Accession No. Z28811, Dec. 14, 1993.
Goldgur, Y. et al., "The crystal structure of phenylalanyl-tRNA synthetase from Thermus thermophilus complexed with cognate tRNA," Structure, 5:59-68 (1997).
Greenberg, Y. et al., "The novel fragment of tyrosyl tRNA synthetase, mini-TyrRS, is secreted to induce an angiogenic response in endothelial cells," FASEB Journal, 22(5):1597-1605 (2008).
Guijarro, J. I. et al., "Structure and Dynamics of the Anticodon Arm Binding Domain of Bacillus stearothermophilus Tyrosyl-tRNA Synthetase," Structure, 10:311-317 (2002).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Hausmann, C. D. et al., "Aminoacyl-tRNA synthetase complexes: molecular multitasking revealed," FEMS Microbiol. Rev., 32(4):705-721 (2008).
Hou, Y-M. et al., "Sequence determination and modeling of structural motifs for the smallest monomeric aminoacyl-tRNA synthetase," Proc. Nat. Acad. Sci., 88(3):976-980 (1991).
Hsu, H-C et al., "Circulating levels of thrombopoietic and inflammatory cytokines in patients with clonal and reactive thrombocytosis," J. Lab. Clin. Med., 134(4):392-397 (1999).
Ivakhno, S. S. et al., "Cytokine-Like Activities of Some Aminoacyl-tRNA Synthetases and Auxiliary p43 Cofactor of Aminoacyloacylation Reaction and Their Role in Oncogenesis," Exp. Oncol., 26(4):250-255 (2004).
Ivanov, K. A. et al., "Non-canonical Functions of Aminoacyl-tRNA Synthetases," Biochemistry (Moscow), 65(8):888-897 (2000).
Jacobo-Molina, A. et al., "cDNA Sequence, Predicted Primary Structure, and Evolving Amphiphilic Helix of Human Aspartyl-tRNA Synthetase," Journal of Biological Chemistry, 264(28):16608-16612 (1989).
Jordanova, A. et al., "Disrupted function and axonal distribution of mutant tyrosyl-tRNA synthetase in dominant intermediate Charcot-Marie-Tooth neuropathy," Nature Genetics, 38(2):197-202 (2006).
Jura, M. et al., "Comprehensive Insight into Human Aminoacyl-tRNA Synthetases as Autoantigens in Idiopathic Inflammatory Myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).
Kimchi-Sarfaty, C. et al., "A 'Silent' polymorphism in the MDR1 gene changes substrate specificty," Science, 315:525-528 (2007).
Kise, Y. et al., "A short peptide insertion crucial for angiostatic activity of human tryptophanyl-tRNA synthetase," Nature Structural & Molecular Biology, 11(2):149-156 (2004).
Kleeman, T. A. et al., "Human Tyrosyl-tRNA Synthetase Shares Amino Acid Sequence Homology with a Putative Cytokine," The Journal of Biological Chemistry, 272(22):14420-14425 (1997).
Kobos, R. et al., "Overview of thrombopoietic agents in the treatment of thrombocytopenia," Clinical Lymphoma & Myeloma, 2008, 8(1):33-43.
Kochendoerfer, G. G., "Site-specific polymer modification of therapeutic proteins," Current Opinion in Chemical Biology, 9:555-560 (2005).
Kordysh, M. et al., "Conformational Flexibility of Cytokine-Like C-Module of Tyrosyl-tRNA Synthetase Monitored by Trp 144 Intrinsic Fluorescence," J. Fluoresc., 16:705-711 (2006).
Kovaleski, B. J. et al.,"In vitro characterization of the interaction between HIV-1 Gag and human lysyl-tRNA synthetase," J. Bio. Chem., 281(28):19449-19456 (2006).
Lee, J. W. et al., "Editing-defective tRNA synthetase causes protein misfolding and neurodegeneration," Nature, 443(7107):50-55 (2006).
Leitao-Goncalves, R. et al., "*Drosophila* as a platform to predict the pathogenicity of novel aminoacyl-tRNA synthetase mutations in CMT," Amino Acids (2011).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Link, A. J. et al., "Discovery of aminoacyl-tRNA synthetase activity through cell-surface display of noncanonical amino acids," Proc. Nat. Acad. Sci., 103(27):10180-10185 (2006).

(56) References Cited

OTHER PUBLICATIONS

Liu, J. et al., "Mutational Switching of a Yeast tRNA Synthetase into a Mammalian-like Synthetase Cytokine," Biochemistry, 41(48):14232-14237 (2002).
Nackley, A. G. et al., "Human Caechol-O-Methytransferase haplotypes modulate protein expression by altering mRNA secondary structure," Science, 314:1930-1933 (2006).
Nangle, L. A. et al., "Charcot-Marie-Tooth disease-associated mutant tRNA synthetases linked to altered dimer interface and neurite distribution defect," PNAS, 104(27):11239-11244 (2007).
Ngo, J. T. et al., "Computational complexity, protein structure prediction, and the Levinthal paradox," In The Protein Folding Problem and Tertiary Structure Prediction, Merz et al. (ed.), Birkhauser, Boston, MA, pp. 433 and 492-495 (1994).
Nichols, R. C. et al., "Human isoleucyl-tRNA synthetase: sequence of the cDNA, alternative mRNA splicing, and the characteristics of an unusually long C-terminal extension," Gene, 155(2):299-304 (1995).
Otani, a. et al., "A fragment of human TrpRS as a potent antagonist of ocular angiogenesis," PNAS, 99(1):178-183 (2002).
Park, S. G., et al., "Aminoacyl tRNA synthetases and their connections to disease," PNAS, 105(32):11043-11049 (2008).
Park, S. G. et al., "Dose-dependent biphasic activity of tRNA synthetase-associating factor, p43, in angiogenesis," The Journal of Biological Chemistry, 277(47):45243-45248 (2002).
Park, S. G. et al., "Is there an answer? Do aminoacyl-tRNA synthetases have biological functions other than in protein biosynthesis?" IUBMB Life, 58(9):556-558 (2006).
Paukstelis, P. J. et al., "NMR Structure of the C-Terminal Domain of a Tyrosyl-tRNA Synthetase That Functions in Group I Intron Splicing," Biochemistry, 50:3816-3826 (2011).
Paukstelis, P. J. et al., "A Tyrosyl-tRNA Synthetase Adapted to Function in Group I Intron Splicing by Acquiring a New RNA Binding Surface," Molecular Cell, 17:417-428 (2005).
Paukstelis, P. J. et al., "Structure of a tyrosyl-tRNA synthetase splicing factor bound to a group I intron RNA," Nature, 451:94-98 (2008).
Quesniaux, V. F.J. et al., "Hematopoiesis, including lymphocyte developmet and maturation," Principles of Immunopharmacology, pp. 3-17 (2005).
Reed, V. S. et al., "Characterization of a Novel N-terminal Peptide in Human Aspartyl-tRNA Synthetase," Journal of Biological Chemistry, 269(52):32937-32941 (1994).
Richardson, R. M. et al., "Role of the cytoplasmic tails of CXCR1 and CXCR2 in mediating leukocyte migration, activation, and regulation," Journal of Immunology, 170(6):2904-2911 (2003).
Riley, L. G. et al., "Mutation of the Mitochondrial Tyrosyl-tRNA Synthetase Gene, YARS2, Causes Myopathy, Lactic Acidosis, and Sideroblastic Anemia-MLASA Syndrome," The American Journal of Human Genetics, 87:52-59 (2010).
Rios-Santos, F. et al., "Down-regulation of CXCR2 on Neutrophilis in Severe Sepsis Is Mediated by Inducible Nitric Oxide Synthase-derived Nitric Oxide," Am. J. Respir. Crit. Care. Med., 175:490-497 (2007).
Sauna, Z. E. et al., "Silent polymorhisms speak: How they affect pharmacogenomics and the treatment of cancer," Cancer Res., 67(20):9609-9612 (2007).
Schluesener, H., "Tyrosyl-tRNA Synthetase: A Housekeeping Protein and an Attractive Harbinger of Cellular Death," Angew. Chem. Int. Ed., 38(24):3635-3637 (1999).
Seburn, K. L. et al., "An active dominant mutation of glycyl-tRNA synthetase causes neuropathy in a Charcot-Marie-Tooth 2D mouse model," Neuron, 51(6):715-726 (2006).
Shi, K-S, "Differential diagnosis for thrombocytopenia," 19(4):447-450 (2008).
Smith, D. F. et al., "Leukocyte phosphoinositide-3 kinase $\gamma$ is required for chemokine-induced, sustained adhesion under flow in vivo," Journal of Leukocyte Biology, 80(6):1491-1499 (2006).
Steer, B. A. et al., "Domain-domain communication in a miniature archaebacterial tRNA synthetase," PNAS, 96(24):13644-13649 (1999).
Steer, B. A. et al., "Major Anticodon-binding Region Missing from an Archaebacterial tRNA Synthetase," The Journal of Biological Chemistry, 274(50):35601-35606 (1999).
Storkebaum, E. et al., "Dominant mutations in the tyrosyl-tRNA synthetase gene recapitulate in *Drosophila* features of human Charcot-Marie-Tooth neuropathy," PNAS, 106(28):11782-11787 (2009).
Stum, M. et al., "An assessment of mechanisms underlying peripheral axonal degeneration caused by aminoacyl-tRNA synthetase mutations," Molecular and Cellular Neuroscience, 46:432-443 (2011).
Suzuki, K-I. et al., "Efficient assay for evaluating human thrombopoiesis using NOD/SCID mice transplanted with cord blood CD34 cells," Journal Compilation, 78:123-130 (2006).
Traves, S. L. et al., "Specific CXC but not CC chemokines cause elevated monocyte migration in COPD: a role for $CXCR_2$," Journal of Leukocyte Biology, 76(2):441-450 (2004).
Trischitta, V. et al., "Endocytosis, recycling, and degradation of the insulin receptor," The Journal of Biological Chemistry, 264(9):5041-5046 (1989).
Tzima, E. et al., "Inhibition of tumor angiogenesis by a natural fragment of a tRNA synthetase," TRENDS in Biochemical Sciences, 31(1):7-10 (2006).
Veronese, F. M. et al., "Preface: Introduction and overview of peptide and protein pegylation," Advanced Drug Delivery Reviews, 54:453-456 (2002).
Vo, M-N. et al., "Dissociating Quaternary Structure Regulates Cell-signaling Functions of a Secreted Human tRNA Synthetase," The Journal of Biological Chemistry, 286(13):11563-11568 (2011).
Wakasugi, K. et al., "Two distinct cytokines released from a human aminoacyl-tRNA synthetase," Science, 284:147-151 (1999).
Wakasugi, K. et al., "A human aminoacyl-tRNA synthetase as a regulator of angiogenesis," Proc. Natl. Acad. Sci., 99(1):173-177 (2002).
Wakasugi, K. et al., "Induction of angiogenesis by a frament of human tyrosyl-tRNA synthetase," The Journal of Biological Chemistry, 277(23):20124-20126 (2002).
Wakasugi et al., "Highly Differentiated Motifs Responsible for Two Cytokine Activities of a Split Human tRNA Synthetase," The Journal of Biological Chemistry, 274(33):23155-23159 (1999).
Wishart, M. J. et al., "A single mutation converts a novel phosphotyrosine binding domain into a dual-specificity phosphatase," J. Biol. Chem., 270(45):26782-26785 (1995).
Xie et al., "Crystallization and preliminary X-ray analysis of a native human tRNA synthetase whose allelic variants are associated with Charcot-Marie-Tooth disease," Acta. Cryst., F62:1243-1246 (2006).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X-L et al., "Relationship of two human tRNA synthetases used in cell signaling," Trends in Biochemical Sciences, 29(5):250-256 (2004).
Yang, X-L et al., "Crystal structures that suggest late development of genetic code components for differentiating aromatic side chains," PNAS, 100(26):15376-15380 (2003).
Yang, X-L et al., "Gain-of-Function Mutational Activation of Human tRNA Synthetase Procytokine," Chemistry & Biology, 14(12):1323-1333 (2007).
Yu, Y. et al., "Crystal structure of human tryptophanyl-tRNA synthetase catalytic fragment," The Journal of Biological Chemistry, 279(9):8378-8388 (2004).
Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).

(56) References Cited

OTHER PUBLICATIONS

Zeng, R. et al., "Different angiogenesis effect of mini-TyrRS/mini-TrpRS by systemic administration of modified siRNAs in rats with acute myocardial infarction," Heart Vessels, 25:324-332 (2010).
Zeng, R. et al., "Effect of mini-tyrosyl-tRNA synthetase/mini-tryptophanyl-tRNA synthetase on ischemic angiogenesis in rats: proliferation and migration of endothelial cells," Heart Vessels, 26:69-80 (2011).
Zwijnenburg, P. J. G. et al., B-1426, "Tyrosyl tRNA synthetase is a chemotactic factor in cerebrospinal fluid from patients with bacterial meningitis," Abstracts of the 42nd Interscience Conference on Antimicrobial Agents and Chemotherapy, San Diego, California, Sep. 27-30, 2002, Session 156(B), p. 55.

* cited by examiner

```
        10         20         30         40         50
MGDAPSPEEK LHLITRNLQE VLGEEKLKEI LKERELKIYW GTATTGKPHV

        60         70         80         90        100
AYFVPMSKIA DFLKAGCEVT ILFADLHAYL DNMKAPWELL ELRVSYYENV

       110        120        130        140        150
IKAMLESIGV PLEKLKFIKG TDYQLSKEYT LDVYRLSSVV TQHDSKKAGA

       160        170        180        190        200
EVVKQVEHPL LSGLLYPGLQ ALDEEYLKVD AQFGGIDQRK IFTFAEKYLP

       210        220        230        240        250
ALGYSKRVHL MNPMVPGLTG SKMSSSEEES KIDLLDRKED VKKKLKKAFC

       260        270        280        290        300
EPGNVENNGV LSFIKHVLFP LKSEFVILRD EKWGGNKTYT AYVDLEKDFA

       310        320        330        340        350
AEVVHPGDLK NSVEVALNKL LDPIREKFNT PALKKLASAA YPDPSKQKPM

       360        370        380        390        400
AKGPAKNSEP EEVIPSRLDI RVGKIITVEK HPDADSLYVE KIDVGEAEPR

       410        420        430        440        450
TVVSGLVQFV PKEELQDRLV VVLCNLKPQK MRGVESQGML LCASIEGINR

       460        470        480        490        500
QVEPLDPPAG SAPGEHVFVK GYEKGQPDEE LKPKKKVFEK LQADFKISEE

       510        520
CIAQWKQTNF MTKLGSISCK SLKGGNIS (SEQ ID NO:1)
```

FIG. 1

```
        10         20         30         40         50
MGDAPSPEEK LHLITRNLQE VLGEEKLKEI LKERELKIYW GTATTGKPHV

        60         70         80         90        100
AYFVPMSKIA DFLKAGCEVT ILFADLHAYL DNMKAPWELL ELRVSYYENV

       110        120        130        140        150
IKAMLESIGV PLEKLKFIKG TDYQLSKEYT LDVYRLSSVV TQHDSKKAGA

       160        170        180        190        200
EVVKQVEHPL LSGLLYPGLQ ALDEEYLKVD AQFGGIDQRK IFTFAEKYLP

       210        220        230        240        250
ALGYSKRVHL MNPMVPGLTG SKMSSSEEES KIDLLDRKED VKKKLKKAFC

       260        270        280        290        300
EPGNVENNGV LSFIKHVLFP LKSEFVILRD EKWGGNKTYT AYVDLEKDFA

       310        320        330        340        350
AEVVHPGDLK NSVEVALNKL LDPIREKFNT PALKKLASAA APDPSKQKPM

       360        370        380        390        400
AKGPAKNSEP EEVIPSRLDI RVGKIITVEK HPDADSLYVE KIDVGEAEPR

       410        420        430        440        450
TVVSGLVQFV PKEELQDRLV VVLCNLKPQK MRGVESQGML LCASIEGINR

       460        470        480        490        500
QVEPLDPPAG SAPGEHVFVK GYEKGQPDEE LKPKKKVFEK LQADFKISEE

       510        520
CIAQWKQTNF MTKLGSISCK SLKGGNIS (SEQ ID NO:2)
```

*FIG. 2*

```
        10         20         30         40         50
MGDAPSPEEK LHLITRNLQE VLGEEKLKEI LKERELKIYW GTATTGKPHV

        60         70         80         90        100
AYFVPMSKIA DFLKAGCEVT ILFADLHAYL DNMKAPWELL ELRVSYYENV

       110        120        130        140        150
IKAMLESIGV PLEKLKFIKG TDYQLSKEYT LDVYRLSSVV TQHDSKKAGA

       160        170        180        190        200
EVVKQVEHPL LSGLLYPGLQ ALDEEYLKVD AQFGGIDQRK IFTFAEKYLP

       210        220        230        240        250
ALGYSKRVHL MNPMVPGLTG SKMSSSEEES KIDLLDRKED VKKKLKKAFC

       260        270        280        290        300
EPGNVENNGV LSFIKHVLFP LKSEFVILRD EKWGGNKTYT AYVDLEKDFA

       310        320        330        340        350
AEVVHPGDLK NSVEVALNKL LDPIREKFNT PALKKLASAA YPDPSKQKPM

       360
AKGPAKNSEP EEVI  (SEQ ID NO:3)
```

*FIG. 3*

```
1     atgggggacg ctcccagccc tgaagagaaa ctgcacctta tcacccggaa cctgcaggag
61    gttctggggg aagagaagct gaaggagata ctgaaggagc gggaacttaa aatttactgg
121   ggaacggcaa ccacgggcaa accacatgtg gcttactttg tgcccatgtc aaagattgca
181   gacttcttaa aggcagggtg tgaggtaaca attctgtttg cggacctcca cgcatacctg
241   gataacatga aagccccatg ggaacttcta gaactccgag tcagttacta tgagaatgtg
301   atcaaagcaa tgctggagag cattggtgtg cccttggaga agctcaagtt catcaaaggc
361   actgattacc agctcagcaa agagtacaca ctagatgtgt acagactctc ctccgtggtc
421   acacagcacg attccaagaa ggctggagct gaggtggtaa agcaggtgga gcaccctttg
481   ctgagtggcc tcttataccc cggactgcag gctttggatg aagagtattt aaaagtagat
541   gcccaatttg gaggcattga tcagagaaag attttcacct ttgcagagaa gtacctccct
601   gcacttggct attcaaaacg ggtccatctg atgaatccta tggttccagg attaacaggc
661   agcaaaatga gctcttcaga agaggagtcc aagattgatc tccttgatcg gaaggaggat
721   gtgaagaaaa aactgaagaa ggccttctgt gagccaggaa atgtggagaa caatggggtt
781   ctgtccttca tcaagcatgt cctttttccc cttaagtccg agtttgtgat cctacgagat
841   gagaaatggg gtggaaacaa aacctacaca gcttacgtgg acctggaaaa ggactttgct
901   gctgaggttg tacatcctgg agacctgaag aattctgttg aagtcgcact gaacaagttg
961   ctggatccaa tccgggaaaa gtttaatacc cctgccctga aaaaactggc cagcgctgcc
1021  tacccagatc cctcaaagca gaagccaatg gccaaaggcc ctgccaagaa ttcagaacca
1081  gaggaggtca tcccatcccg gctggatatc cgtgtgggga aaatcatcac tgtggagaag
1141  cacccagatg cagacagcct gtatgtagag aagattgacg tgggggaagc tgaaccacgg
1201  actgtggtga gcggcctggt acagttcgtg cccaaggagg aactgcagga caggctggta
1261  gtggtgctgt gcaacctgaa accccagaag atgagaggag tcgagtccca aggcatgctt
1321  ctgtgtgctt ctatagaagg gataaaccgc caggttgaac ctctggaccc tccggcaggc
1381  tctgctcctg gtgagcacgt gtttgtgaag ggctatgaaa agggccaacc agatgaggag
1441  ctcaagccca agaagaaagt cttcgagaag ttgcaggctg acttcaaaat ttctgaggag
1501  tgcatcgcac agtggaagca aaccaacttc atgaccaagc tgggctccat ttcctgtaaa
1561  tcgctgaaag gggggaacat tagctagcca gcccagcatc ttcccccctt cttccaccac
1621  tgagtcatct gctgtctctt cagtctgctc catccatcac ccatttaccc atctctcagg
1681  aca (SEQ ID NO:4)
```

```
        10         20         30         40         50
XXXXXXXXXK IFTFAEKYLP ALGYSKRVHL MNPMVPGLTG SKMSSSEEES

        60         70         80         90        100
KIDLLDRKED VKKKLKKAFC EPGNVENNGV LSFIKHVLFP LKSEFVILRD

       110        120        130        140        150
EKWGGNKTYT AYVDLEKDFA AEVVHPGDLK NSVEVALNKL LDPIREKFNT

       160        170        180        190        200
PALKKLASAA YPDPSKQKPM AKGPAKNSEP EEVIPSRLDI RVGKIITVEK

       210        220        230        240        250
HPDADSLYVE KIDVGEAEPR TVVSGLVQFV PKEELQDRLV VVLCNLKPQK

       260        270        280        290        300
MRGVESQGML LCASIEGINR QVEPLDPPAG SAPGEHVFVK GYEKGQPDEE

       310        320        330        340
LKPKKKVFEK LQADFKISEE CIAQWKQTNF MTKLGSISCK SLKGGNIS
(SEQ ID NO:6)
```

*FIG. 7* cDNA encoding SP1

```
   1 ttcagaaagt ggtggaggga agacttcctt tttcccagag acagaaggtt atgcacccag
  61 tggcctggga ccattgttct gggctttttt tcccttcgac atggatttgc ttctcactgt
 121 gtacccccaac caccaaaacc accctgagat caatgctggt gctcctgcat cagatggctt
 181 agagatcctt ccacctctta acacaagcat ctaggtccac tttactcaaa tctggcctca
 241 gttgagagca gagtatacca tcagagccca ttctcctgtc tgctgtctgg gacgtggaaa
 301 gaaagttagc tctagggggt ctttccaggg gcctctgtaa ggactggatg ctcctttccg
 361 gaatccaaga gttcaccagg ctgcttctct aatggacgat gatcctcttc ctcctgacgt
 421 ctctccctgg cagcacccag atgcagacag cctgtatgta gagaagattg acgtggggga
 481 agctgaacca cggactgtgg tgagcggcct ggtacagttc gtgcccaagg aggaactgca
 541 ggacaggctg gtagtggtgc tgtgcaacct gaaaccccag aagatgagag gagtcgagtc
 601 ccaaggcatg cttctgtgtg cttctatgtg agtgaggact tggagtgggg cacaggacct
 661 ggggaggcca ggaagagtag ggaatcagcc catatgatgt ccttccacac accaggtgga
 721 agctctgaga acacgtgcct cttccttgct gatgccaaaa gttgatgcat gaaggactta
 781 tcgtacaagt actgttaatg aagcatttta cctacagtta attttgttaa aatagaaatg
 841 gagggctcaa accagtacat acccaagtct tactactagt aaggagtgga gcagggattc
 901 aaatcccagt tttgatgtct ataaagtcct cgctacgtta ttttatactt cctcccctag
 961 aaacacagat tttggtatct tgacacacaa ttttggtata gcctgggtta atgtaaccct
1021 ggtgatatgc agggatgtag caagataaga ggacctcctg gggctctggt actgaggatg
1081 ccctaaatcc catcagggcc cctgtgtaaa ggcccggatt gctttggcct ccacagtcac
1141 tggaacccat ccatagcctc actcttctct tgtcctgtgt cttcccagag aagggataaa
1201 ccgccaggtt gaacctctgg accctccggc aggctctgct cctggtgagc acgtgtttgt
1261 gaagggctat gaaaagggcc aaccagatga ggagctcaag cccaagagga aagtcttcga
1321 gaagttgcag gctgacttca aaatttctga ggagtgcatc gcacagtgga agcaaaccaa
1381 cttcatgacc aagctgggct ccatttcctg taaatcgctg aaaggggga acattagcta
1441 gccagcccag catcttcccc ccttcttcca ccactgagtc atctgctgtc tcttcagtct
1501 gctccaccca tcacccattt acccatctct caggacacgg aagcagcggg tttggactct
1561 ttattcggtg cagaactcgg caagggcag cttaccctcc ccagaaccca ggatcatcct
1621 gtctggctgc agtgagagac caacccctaa caagggctgg gccacagcag ggagtccagc
1681 cctaccttct tcccttggca gctggagaaa tctggtttca atataactca tttaaaaatt
1741 tatgccacag tccttataat tggaaaaata ctggtgccca ggtttttcttg gagttatcca
1801 agcagctgcg ccctagctg ggatctggta cctggactag gctaattaca gcttctcccc
1861 aacaggaaac tgtgggattt gaaaaggaaa gggaagggaa aacagagaac ctagtggtct
1921 accaagtggt tggcaacttt cccaatgtct gcttactctg aggcttggca ctgggggcca
1981 gggcctgccc cagggctcct ggaatttccc ttgatccagc taggctggga cactccctaa
2041 atcagctgcg tgttgttagc atcaggcaga atgaatggca gagagtgatt ctgtcttcat
2101 agagggtggg gtacttctcc ataaggcatc tcagtcaaat ccccatcact gtcataaatt
2161 caaataaaat gtctgaac (SEQ ID NO:7)
```

```
        10         20         30         40         50
MGDAPSPEEK LHLITRNLQE VLGEEKLKEI LKERELKTYW GTATTGKPHV

        60         70         80         90        100
AYFVPMSKIA DFLKAGCEVT ILFADLHAYL DNMKAPWELL ELRVSYYENV

       110        120        130        140        150
IKAMLESIGV PLEKLKFIKG TDYQLSKEYT LDVYRLSSVV TQHDSKKAGA

       160        170        180        190        200
EVVKQVEHPL LSGLLYPGLQ ALDEEYLKVD AQFGGIDQRK IFTFAEKYLP

       210        220        230        240        250
ALGYSKRVHL MNPMVPGLTG SKMSSSEEES KIDLLDRKED VKKKLKKAFC

       260        270        280        290        300
EPGNVENNGV LSFIKHVLFP LKSEFVILRD EKWGGNKTYT AYVDLEKDFA

       310        320        330        340        350
AEVVHPGDLK NSVEVALNKL LDPIREKFNT PALKKLASAA YPDPSKQKPM

       360        370        380
AKGXXXXXXX XXXXXXXXXX XXXXXXXXXX XXXXXXXX (SEQ ID NO:8)
```

FIG. 9 cDNA encoding SP2

```
   1 atgggggacg ctcccagccc tgaagagaaa ctgcacctta tcacccggaa cctgcaggag
  61 gttctggggg aagagaagct gaaggagata ctgaaggagc gggaacttaa aatttactgg
 121 ggaacggcaa ccacgggcaa accacatgtg gcttactttg tgcccatgtc aaagattgca
 181 gacttcttaa aggcagggtg tgaggtaaca attctgtttg cggacctcca cgcatacctg
 241 gataacatga aagccccatg ggaacttcta gaactccgag tcagttacta tgagaatgtg
 301 atcaaagcaa tgctggagag cattggtgtg cccttggaga agctcaagtt catcaaaggc
 361 actgattacc agctcagcaa agagtacaca ctagatgtgt acagactctc ctccgtggtc
 421 acacagcacg attccaagaa ggctggagct gaggtggtaa agcaggtgga gcaccctttg
 481 ctgagtggcc tcttataccc cggactgcag gctttggatg aagagtattt aaaagtagat
 541 gcccaatttg gaggcattga tcagagaaag attttcacct ttgcagagaa gtacctccct
 601 gcacttggct attcaaaacg ggtccatctg atgaatccta tggttccagg attaacaggc
 661 agcaaaatga gctcttcaga agaggagtcc aagattgatc tccttgatcg gaaggaggat
 721 gtgaagaaaa aactgaagaa ggccttctgt gagccaggaa atgtggagaa caatggggtt
 781 ctgtccttca tcaagcatgt cctttttccc cttaagtccg agtttgtgat cctacgagat
 841 gagaaatggg gtggaaacaa aacctacaca gcttacgtgg acctggaaaa ggactttgct
 901 gctgaggttg tacatcctgg agacctgaag aattctgttg aagtcgcact gaacaagttg
 961 ctggatccaa tccgggaaaa gtttaatacc cctgccctga aaaaactggc cagcgctgcc
1021 tacccagatc cctcaaagca gaagccaatg gccaaaggcc tgccaagaat tcagaaccag
1081 aggaggtcat cccatcccgg ctggatatcc gtgtggggaa aatcatcact gtggagaagc
1141 acccagatgc agacagcctg tatgtag (SEQ ID NO:9)
```

```
        10         20         30         40         50
MNPMVPGLTG SKMSSSEEES KIDLLDRKED VKKKLKKAFC EPGNVENNGV

        60         70         80         90        100
LSFIKHVLFP LKSEFVILRD EKWGGNKTYT AYVDLEKDFA AEVVHPGDLK

       110        120        130        140        150
NSVEVALNKL LDPIREKFNT PALKKLASAA YPDPSKQKPM AKGPAKNSEP

       160        170        180        190        200
EEVIPSRLDI RVGKIITVEK HPDADSLYVE KIDVGEAEPR TVVSGLVQFV

       210        220        230        240        250
PKEELQDRLV VVLCNLKPQK MRGVESQGML LCASIEGINR QVEPLDPPAG

       260        270        280        290        300
SAPGEHVFVK GYEKGQPDEE LKPKKKVFEK LQADFKISEE CIAQWKQTNF

       310
MTKLGSISCK SLKGGNIS (SEQ ID NO:10)
```

FIG. 11 cDNA encoding SP3

```
   1 gaaagatttt cacctttgca gagaagtacc tccctgcact tggctattca aaacgggtcc
  61 atctgatgaa tccratggtt ccaggattaa caggcagcaa aatgagctct tcagaagagg
 121 agtccaagat tgatctcctt gatcggaagg aggatgtgaa gaaaaaactg aagaaggcct
 181 tctgtgagcc aggaaatgtg gagaacaatg gggttctgtc cttcatcaag catgtccttt
 241 ttccccttaa gtccgagttt gtgatcctac gagatgagaa atggggtgga aacaaaacct
 301 acacagctta cgtggacctg gaaaaggact ttgctgctga ggttgtacat cctggagacc
 361 tgaagaattc tgttgaagtc gcactgaaca agttgctgga tccaatccgg gaaaagttta
 421 ataccccctgc cctgaaaaaa ctggccagcg ctgcctaccc agatccctca aagcagaagc
 481 caatggccaa aggccctgcc aagaattcag aaccagagga ggtcatccca tcccggctgg
 541 atatccgtgt ggggaaaatc atcactgtgg agaagcaccc agatgcagac agcctgtatg
 601 tagagaagat tgacgtgggg gaagctgaac cacggactgt ggtgagcggc ctggtacagt
 661 tcgtgcccaa ggaggaactg caggacaggc tggtagtggt gctgtgcaac ctgaaacccc
 721 agaagatgag aggagtcgag tcccaaggca tgcttctgtg tgcttctata gaagggataa
 781 accgccaggt tgaacctctg gaccctccgg caggctctgc tcctggtgag cacgtgtttg
 841 tgaagggcta tgaaaagggc caaccagatg aggagctcaa gcccaagaag aaagtcttcg
 901 agaagttgca ggctgacttc aaaatttctg aggagtgcat cgcacagtgg aagcaaacca
 961 acttcatgac caagctgggc tccatttcct gtaaatcgct gaaagggggg aacattagct
1021 agccagccca gcatcttccc cccttcttcc accactgagt catctgctgt ctcttcagtc
1081 tgctccatcc atcacccatt tacccatctc tcaggacacg gaagcagcgg gtttggactc
1141 tttattcggt gcagaactcg gcaaggggca gcttaccctc cccagaaccc aggatcatcc
1201 tgtctggctg cagtgagaga ccaaccccta acaagggctg ggccacagca gggagtccag
1261 ccctaccttc ttcccttggc agctggagaa atctggtttc aatataactc atttaaaat
1321 ttatgccaca gtccttataa ttggaaaaat actggtgccc aggtttttctt ggagttatcc
1381 aagcagctgc gcccctagct gggatctggt acctggacta ggctaattac agcttctccc
1441 caacaggaaa ctgtgggatt tgaaaaggaa agggaaggga aaacagagaa cctagtggtc
1501 taccaagtgg ttggcaactt tcccaatgtc tgcttactct gaggcttggc actgggggcc
1561 agggcctgcc ccagggctcc tggaatttcc cttgatccag ctaggctggg acactcccta
1621 aatcagctgc gtgttgttag catcaggcag aatgaatggc agagagtgat tctgtcttca
1681 tagagggtgg ggtacttctc cataaggcat ctcagtcaaa tccccatcac tgtcat
     (SEQ ID NO:11)
```

```
1          11         21         31         41         51
M AKGPAKNSEP EEVIPSRLDI RVGKIITVEK HPDADSLYVE KIDVGEAEPR

         61         71         81         91        101
  TVVSGLVQFV PKEELQDRLV VVLCNLKPQK MRGVESQGML LCASIEGINR

        111        121        131        141        151
  QVEPLDPPAG SAPGEHVFVK GYEKGQPDEE LKPKKKVFEK LQADFKISEE

        161        171
  CIAQWKQTNF MTKLGSISCK SLKGGNIS  (SEQ ID NO:12)
```

*FIG. 13* cDNA encoding SP4

```
   1 atgggggacg ctcccagccc tgaagagaaa ctgcacctta tcacccggaa cctgcaggag
  61 gttctggggg aagagaagct gaaggagata ctgaaggagc gggaacttaa aatttactgg
 121 ggaacggcaa ccacgggcaa accacatgtg gcttactttg tgcccatgtc aaagattgca
 181 gacttcttaa aggcagggtg tgaggtaaca attctgtttg cggacctcca cgcatacctg
 241 gataacatga aagccccatg ggaacttcta gaactccgag tcagttacta tgagaatgtg
 301 atcaaagcaa tgctggagag cattggtgtg cccttggaga agctcaagtt catcaaaggc
 361 actgattacc agctcagcaa agagtacaca ctagatgtgt acagactctc ctccgtggtc
 421 acacagcacg attccaagaa ggctggagct gaggtggtaa agcaggtgga gcaccctttg
 481 ctgagtggcc tcttataccc cggactgcag gctttggatg aagagtattt aaaagtagat
 541 gcccaatttg gaggcattga tcagagaaag attttcacct ttgcagagaa gtacctccct
 601 gcacttggct attcaaaacg ggtccatctg atgaatccta tggttccagg attaacaggc
 661 agcaaaatga gctcttcaga agaggagtcc aagattgatc tccttgatcg gaaggaggat
 721 gtgaagaaaa aactgaagaa ggccttctgt gagccaggaa atgtggagaa caatggggtt
 781 ctgtccttca tcaagcatgt cctttttccc cttaagtccg agtttgtgat cctacgagat
 841 gagaaatggg gtggaaacaa aacctacaca gcttacgtgg acctggaaaa ggactttgct
 901 gctgaggttg tacatcctgg agacctgaag aattctgttg aagtcgcact gaacaagttg
 961 ctggatccaa tccgggaaaa gtttaatacc cctgccctga aaaaactggc cagcgctgcc
1021 tacccagatc cctcaaagca gaagccaatg gccaaaggcc tgccaagaat tcagaaccag
1081 aggaggtcat cccatcccgg ctggatatcc gtgtggggaa aatcatcact gtggagaagc
1141 acccagatgc agacagcctg tatgtag (SEQ ID NO:13)
```

```
        10         20         30         40         50
XXXXXXXXPM AKGPAKNSEP EEVIPSRLDI RVGKIITVEK HPDADSLYVE

        60         70         80         90        100
KIDVGEAEPR TVVSGLVQFV PKEELQDRLV VVLCNLKPQK MRGVESQGML

       110        120        130        140        150
LCASIEGINR QVEPLDPPAG SAPGEHVFVK GYEKGQPDEE LKPKKKVFEK

       160        170        180
LQADFKISEE CIAQWKQTNF MTKLGSISCK SLKGGNIS  (SEQ ID NO:14)
```

FIG. 15 cDNA encoding SP5

```
   1 gccagacaca gtggctcaca cctgtaatct taacactttg gaaggctgag gcaggcggat
  61 cacttgagcc caaaagttag agaccaaaac ccagtctcta cccaaaaaaa aaaaaaaaaa
 121 aaaaattagc caggcatagt agcacatgcc tgtagtccca gctacttggg aggctgaggt
 181 gagaggatca cctgagcatg ggaagttga gactgcagtg agccatgatc gcaccactgc
 241 actccagcct gggcaacaga gtgagactct atgtctcaaa aaaagaaaaa tgatagaaat
 301 tagattagac ctattatacc caaccggtat atagggtatc gatagtttct tacacagctg
 361 ttgggcagag cctgcagagc ttagagaagc ttatctttag attctcccag tttccttcta
 421 tgtgcatggg cctggctctt agttggccat ccacttgtgc gtaatgctaa gatattggca
 481 ttgatagctt tgtgcgaccc ttccagaaaa aaactcagta actcagtaaa attttttttt
 541 tttttctaa aagagacaga gtctggctct gttgcccagc ctggtcttga agtcctgggc
 601 ttaagcaatc ctcccgtctc agcctcccaa agtgctagaa ttacaggtgt gagctaccac
 661 acctggccaa gactcagtaa attctatgtg gaatgcatga atggaaatac ctaaaggagg
 721 caaagctact actgctccct ccccgctagt ctaataattg agggagagaa cagatgaaaa
 781 tcaggtatgt catgtctgaa aggttgccaa cccagtatta aagaagttac aactcagtgt
 841 ttagactctg gggattctac actaaatctt acctaatctc agtgtcttaa cgtggtggga
 901 tcagcagctg acctgccaca gggaagaatt ctacctcatg ggttcttct cattcccaga
 961 gccaatggcc aaaggccctg ccaagaattc agaaccagag gaggtcatcc catcccggct
1021 ggatatccgt gtggggaaaa tcatcactgt ggagaagcac ccagatgcag acagcctgta
1081 tgtagagaag attgacgtgg gggaagctga accacggact gtggtgagcg gcctggtaca
1141 gttcgtgccc aaggaggaac tgcaggacag gctggtagtg gtgctgtgca acctgaaacc
1201 ccagaagatg agaggagtcg agtcccaagg catgcttctg tgtgcttcta tagaagggat
1261 aaaccgccag gttgaacctc tggaccctcc ggcaggctct gctcctggtg agcacgtgtt
1321 tgtgaagggc tatgaaaagg gccaaccaga tgaggagctc aagcccaaga agaaagtctt
1381 cgagaagttg caggctgact tcaaaatttc tgaggagtgc atcgcacagt ggaagcaaac
1441 caacttcatg accaagctgg gctccatttc ctgtaaatcg ctgaaagggg ggaacattag
1501 ctagccagcc cagcatcttc cccccttctt ccaccactga gtcatctgct gtctcttcag
1561 tctgctccat ccatcaccca tttacccatc tctcaggaca cggaagcagc gggtttggac
1621 tctttattcg gtgcagaact cggcaagggg cagcttaccc tccccagaac ccaggatcat
1681 cctgtctggc tgcagtgaga gaccaacccc taacaagggc tgggccacag cagggagtcc
1741 agccctacct tctttccttg gcagctggag aaatctggtt tcaatataac tcatttaaaa
1801 atttatgcca cagtccttat aattggaaaa atactggtgc ccaggttttc ttggagttat
1861 ccaagcagct gcgcccctag ctgggatctg gtacctggac taggctaatt acagcttctc
1921 cccaacagga aactgtggga tttgaaaagg aaagggaagg gaaaacagag aacctagtgg
1981 tctaccaagt ggttggcaac tttcccaatg tctgcttact ctgaggcttg gcactggggg
2041 ccagggcctg ccccagggct cctggaattt cccttgatcc agctaggctg ggacactccc
2101 taaatcagct gcgtgttgtt agcatcaggc agaatgaatg gcagagagtg attctgtctt
2161 catagagggt ggggtacttc tccataaggc atctcagtca aatccccatc actgtcataa
2221 attcaaataa aatgtctgaa caagggaaaa aaaaaaaaaa aa   (SEQ ID NO:15)
```

FIG. 16

| Variant | NCBI | Annotation | mRNA difference from Reference | NCBI ORF prediction |
|---|---|---|---|---|
| SP1 (SEQ ID NO:7) | AK026535 | Homo sapiens cDNA: FLJ22882 fis, clone KAT03587, highly similar to HSU89436 Human tyrosyl-tRNA synthetase Mrna, Signet-ring cell carcinoma | Skip part of Exon 1, 2 nt-gap in Exon 5 | 348aa |
| SP2 (SEQ ID NO:9) | HSU40714 | Human tyrosyl-tRNA synthetase mRNA, complete cds | Skip Exons 12&13 and part of Exons 1&11, 1 nt-gap in Exon 10 | 359aa (Reported) |
| SP3 (SEQ ID NO:11) | CR626320 | full-length cDNA clone CS0DI038YE17 of Placenta Cot 25-normalized | Skip Exons 1-4, no gap | 318aa |
| SP4 (SEQ ID NO:13) | AK127182 | Homo sapiens cDNA FLJ45047 fis, clone BRCOC2016881, highly similar to Tyrosyl-tRNA synthetase, Corpus callosum (Brain) | Skip Exons 1-8, 1214bp of Intron 8-9 extension before Exon 9, no gap | 179aa |
| SP5 (SEQ ID NO:15) | BC35242 | Homo sapiens tyrosyl-tRNA synthetase, Testis mRNA (cDNA clone IMAGE:4337840), with apparent retained intron | Skip Exons 1-9, 259bp of Intron 9-10 extension before Exon 10, no gap | 168aa |

*FIG. 18*

Tyrosyl-tRNA Synthetase Polypeptides Stimulate Polymorphonuclear (PMN) Cell Migration Tyrosyl-tRNA Synthetase Polypeptides Impact Megakaryocyte Progenitor Cells Tyrosyl-tRNA Synthetase Polypeptides Impact Megakaryocyte Progenitor Cells
LATE
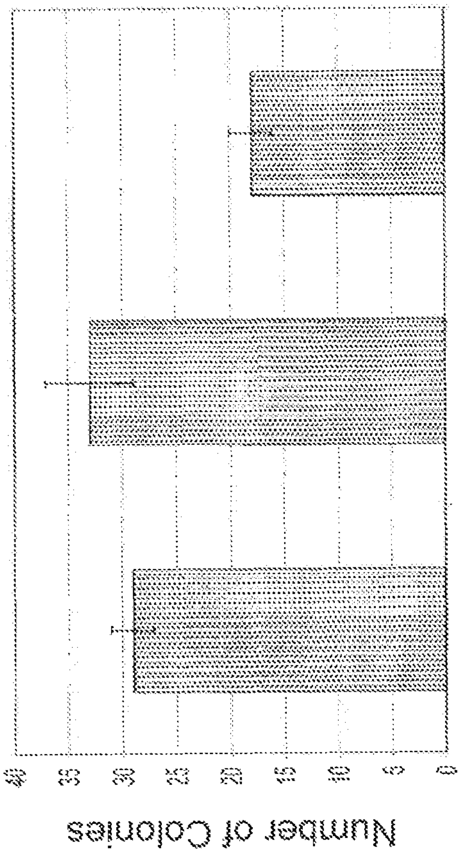
FIG. 26C

THROMBOPOIETIC ACTIVITY OF TYROSYL-TRNA SYNTHETASE POLYPEPTIDES

CROSS-REFERENCE TO RELATED APPLICATION

This application is a continuation of U.S. application Ser. No. 12/482,151, filed Jun. 10, 2009, now abandoned, which claims the benefit under 35 U.S.C. §119(e) of U.S. Provisional Patent Application No. 61/060,747, filed Jun. 11, 2008, each of which is incorporated herein by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_009_02US_ST25.txt. The text file is about 38 KB, was created on Feb. 13, 2014, and is being submitted electronically via EFS-Web.

BACKGROUND

1. Technical Field

The present invention relates generally to thrombopoietic compositions comprising tyrosyl-tRNA synthetase polypeptides, including truncations and/or variants thereof, and methods of using such compositions in the treatment of diseases or conditions that benefit from increased thrombopoiesis, such as diseases or conditions associated with thrombocytopenia.

2. Description of the Related Art

Thrombocytopenia relates generally to a condition in which the number of platelets per unit volume of peripheral blood in a subject is lower than normal. For example, normal platelet counts generally range from about 150,000 $mm^3$ to about 450,000 $mm^3$, and thrombocytopenia is typically characterized by a decrease in the platelet count to about 100,000/$mm^3$ or less.

Platelets, or thrombocytes, are colorless blood cells that play an important role in blood clotting by clumping together and forming plugs in blood vessel holes. Thrombopoiesis refers to the process by which platelets are formed from precursor hematopoietic cells, such as megakaryocytes. Thrombopoiesis is primarily regulated by thrombopoietin, which is in turn regulated by a variety of mechanisms, such as receptor-mediated uptake and destruction in response to increased platelet levels, among other factors.

Thrombocytopenia is associated with many underlying causes, such as increased destruction of platelets, decreased production of platelets, consumption of platelets, trapping of platelets, in addition to medication-induced thrombocytopenia. Given the central role of platelets in blood clotting, initial symptoms of thrombocytopenia normally involve various forms of bleeding and purpura. Since subjects are at increased risk for bleeding, early diagnosis and treatment are important, especially for the prevention of progress to more serious symptoms, such as cerebral bleeding.

Treatment for conditions of reduced platelet count is often guided by etiology and disease severity. Currently available treatments for thrombocytopenia and related conditions include, for example, corticosteroids, IVIG, splenectomy, and platelet transfusion, which methods are either palliative and non-specific, or drastic and expensive. In addition, previous efforts to utilize thrombopoietin, the primary biological mediator of thrombopoiesis, have failed in the clinic due to the serious effects observed in patients who developed an immune response to the drug and, consequently, to their own endogenous thrombopoietin. Thrombopoietin mimetics and small molecule activators of the thrombopoietin receptor are in development but have not been approved by the Food and Drug Administration (FDA).

Aminoacyl-tRNA synthetases, which catalyze the aminoacylation of tRNA molecules, are essential for decoding genetic information during the process of translation. In higher eukaryotes, aminoacyl-tRNA synthetases associate with other polypeptides to form supramolecular multienzyme complexes. Each of the eukaryotic tRNA synthetases consists of a core enzyme, which is closely related to the prokaryotic counterpart of the tRNA synthetase, and an additional domain that is appended to the amino-terminal or carboxyl-terminal end of the core enzyme. Human tyrosyl-tRNA synthetase (YRS), for example, has a carboxyl-terminal domain that is not part of prokaryotic and lower eukaryotic YRS molecules.

Aminoacyl tRNA synthetases, such as tyrosyl-tRNA synthetase, are currently associated with expanded functions in mammalian cells, including activities in signal transduction pathways, among others.

BRIEF SUMMARY

The present invention stems from the unexpected finding that compositions comprising tyrosyl-tRNA synthetase (YRS) polypeptides, including truncated and/or variant polypeptides thereof, stimulate thrombopoiesis in vivo (i.e., increased platelet formation). Accordingly, embodiments of the present invention may be utilized generally to treat and/or reduce the risk of developing diseases or conditions associated with thrombocytopenia, or reduced platelet levels.

Certain embodiments include methods of increasing the platelet count in a subject, comprising administering to the subject a composition comprising a thrombopoietically-effective concentration of a tyrosyl-tRNA synthetase polypeptide, thereby increasing the platelet count in the subject. Certain embodiments include methods of treating, or reducing the risk of developing, thrombocytopenia in subject, comprising administering to the subject a composition comprising a thrombopoietically-effective concentration of a tyrosyl-tRNA synthetase polypeptide, thereby treating or reducing the risk of developing thrombocytopenia in the subject. Certain embodiments contemplate methods of stimulating thrombopoiesis in a subject, comprising administering to the subject a composition comprising a thrombopoietically-effective concentration of a tyrosyl-tRNA synthetase polypeptide, thereby stimulating thrombopoiesis in the subject. Certain embodiments include methods of maintaining platelet count in a subject (e.g., a subject undergoing a therapy associated with reduced platelet count), comprising administering to the subject a thrombopoietically-effective concentration of a tyrosyl-tRNA synthetase polypeptide, thereby maintaining platelet count in the subject.

Certain embodiments encompass methods of stimulating megakaryocyte migration, proliferation and/or differentiation in a subject, comprising administering to the subject a thrombopoietically-effective concentration of a tyrosyl-tRNA synthetase polypeptide, thereby stimulating megakaryocyte proliferation and/or differentiation in the subject. Certain embodiments include methods of stimulating neutrophil migration or proliferation in a subject, comprising administering to the subject a thrombopoietically-effective concentration of a tyrosyl-tRNA synthetase polypeptide, thereby stimulating neutrophil proliferation in the subject.

In certain aspects, the subject has, or is at risk for having, a disease or condition associated with a decreased or reduced platelet count. In certain aspects, the subject has a platelet count of about 100,000/$mm^3$ or lower, about 110,000/$mm^3$ or lower, about 120,000/$mm^3$ or lower, about 130,000/$mm^3$ or lower, about 140,000/$mm^3$ or lower, or about 150,000/$mm^3$ or lower. In certain embodiments, the disease or condition associated with a decreased or reduced platelet count includes, but is not limited to, bleeding, bruising, epistaxis (nose bleeds), hypersplenism, hypothermia, Epstein-Barr virus infection, infectious mononucleosis, Wiskott-Aldrich syndrome, maternal ingestion of thiazides, congenital amegakaryocytic thrombocytopenia, thrombocytopenia absent radius syndrome, Fanconi anemia, Bemard-Soulier syndrome, May-Hegglin anomaly, Grey platelet syndrome, Alport syndrome, neonatal rubella, aplastic anemia, myeolodysplastic syndrome, leukemia, lymphoma, tumor, cancer of the bone marrow, nutritional deficiency, radiation exposure, liver failure, bacterial sepsis, measles, dengue fever, HIV infection or AIDS, prematurity, erythroblastosis fetalis, idiopathic thrombocytopenic purpura (ITP), maternal ITP, hemolytic-uremic syndrome, disseminated intravascular coagulation, thrombotic thrombocytopenic purpura (TTP), post-transfusion purpura, systemic lupus erythematosus, rheumatoid arthritis, neonatal alloimmune thrombocytopenia, and paroxysmal nocturnal hemoglobinuria, hepatitis C virus (HCV) infection, medication induced thrombocytopenia, and chemotherapy induced thrombocytosis (CIT), among others known in the art. In certain aspects, the subject is a platelet donor.

In certain embodiments, the condition associated with a decreased or reduced platelet count is induced by a medication or drug (e.g., medication induced thrombocytopenia, chemotherapy induced thrombocytosis). Examples of medications or drugs that reduce platelet count may be selected from chemotherapeutic agents, nonsteroidal anti-inflammatory agents, sulfonamides, vancomycin, clopidogrel, glycoprotein IIb/IIIa inhibitors, interferons, valproic acid, abciximab, linezolid, famotidine, mebeverine, histamine blockers, alkylating agents, heparin, alcohol, and antibiotics. In certain embodiments, the chemotherapeutic agents may be selected from cisplatin (CDDP), carboplatine, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein transferase inhibitors, transplatinum, 5-fluorouracil, vincristine, vinblastine and methotrexate, Temazolomide (an aqueous form of DTIC), or any analog or derivative variant of the foregoing.

In certain embodiments of the claimed methods, the tyrosyl-tRNA synthetase polypeptide comprises a mammalian tyrosyl-tRNA synthetase, including a mammalian tyrosyl-tRNA synthetase truncated at its C-terminus. In certain of the methods provided herein, the tyrosyl-tRNA synthetase polypeptide comprises the amino acid sequence of SEQ ID NO: 1, 2, 3, 6, 8, 10, 12, or 14, wherein about 1-50 amino acid residues are truncated from its C-terminus. In certain of the methods provided herein, the tyrosyl-tRNA synthetase polypeptide comprises the amino acid sequence of SEQ ID NO: 1, 2, 3, 6, 8, 10, 12, or 14, wherein about 50-100 amino acid residues are truncated from its C-terminus. In certain embodiments, the tyrosyl-tRNA synthetase polypeptide comprises the amino acid sequence of SEQ ID NO: 1, 2, 3, 6, 8, 10, 12, or 14, wherein about 100-150 amino acid residues are truncated from its C-terminus. In other embodiments, the tyrosyl-tRNA synthetase polypeptide comprises the amino acid sequence of SEQ ID NO: 1, 2, 3, 6, 8, or 10, wherein about 150-200 residues are truncated from its C-terminus. In other embodiments, the methods provided herein encompass wherein the tyrosyl-tRNA synthetase polypeptide comprises the amino acid sequence of SEQ ID NO: 1, 2, 3, 6, 8, or 10, wherein about 200-250 amino acid residues are truncated from its C-terminus. Particular examples of C-terminally truncated tyrosyl-tRNA synthetase polypeptides include polypeptides comprising or consisting of amino acids 1-343, amino acids 1-344, amino acids 1-350, amino acids 1-353, or amino acids 1-364 of the amino acid sequence set forth in SEQ ID NOS:1, 2, or 3. Additional examples of C-terminally truncated tyrosyl-tRNA synthetase polypeptides include the polypeptides of SEQ ID NOS:3 and 8.

In certain embodiments of the claimed methods, the tyrosyl-tRNA synthetase polypeptide comprises a mammalian tyrosyl-tRNA synthetase truncated at its N-terminus. In certain of the methods provided herein, the tyrosyl-tRNA synthetase polypeptide comprises the amino acid sequence of SEQ ID NO: 1, 2, 3, 6, 8, 10, 12, or 14, wherein about 1-50 amino acid residues are truncated from its N-terminus. In certain of the methods provided herein, the tyrosyl-tRNA synthetase polypeptide comprises the amino acid sequence of SEQ ID NO: 1, 2, 3, 6, 8, 10, 12, or 14, wherein about 50-100 amino acid residues are truncated from its N-terminus. In certain embodiments, the tyrosyl-tRNA synthetase polypeptide comprises the amino acid sequence of SEQ ID NO: 1, 2, 3, 6, 8, 10, 12, or 14, wherein about 100-150 amino acid residues are truncated from its N-terminus. In other embodiments, the tyrosyl-tRNA synthetase polypeptide comprises the amino acid sequence of SEQ ID NO: 1, 2, 3, 6, 8, or 10, wherein about 150-200 residues are truncated from its N-terminus. In other embodiments, the methods provided herein encompass wherein the tyrosyl-tRNA synthetase polypeptide comprises the amino acid sequence of SEQ ID NO: 1, 2, 3, 6, 8, or 10, wherein about 200-250 amino acid residues are truncated from its N-terminus. Particular examples of N-terminally truncated tyrosyl-tRNA synthetase polypeptides include the polypeptides of SEQ ID NOS:6, 10, 12, and 14.

In certain of the methods described herein, the tyrosyl-tRNA synthetase polypeptide is selected from: (a) a polypeptide comprising an amino acid sequence at least 80% identical to the amino acid sequence set forth in SEQ ID NO:2, wherein the alanine at position 341 is not substituted with a tyrosine; (b) a polypeptide comprising an amino acid sequence at least 90% identical to the amino acid sequence set forth in SEQ ID NO:2, wherein the alanine at position 341 is not substituted with a tyrosine; (c) a polypeptide comprising an amino acid sequence at least 95% identical to the amino acid sequence set forth in SEQ ID NO:2, wherein the alanine at position 341 is not substituted with a tyrosine; (d) a polypeptide comprising an amino acid sequence at least 98% identical to the amino acid sequence set forth in SEQ ID NO:2, wherein the alanine at position 341 is not substituted with a tyrosine; and (e) a polypeptide comprising the amino acid sequence set forth in SEQ ID NO:2.

In certain embodiments of the methods provided herein, the tyrosyl-tRNA synthetase polypeptide is selected from: (a) a polypeptide comprising an amino acid sequence at least 80% identical to the amino acid sequence set forth in SEQ ID NO: 1, 2, 3, 6, 8, 10, 12, or 14; (b) a polypeptide comprising an amino acid sequence at least 90% identical to the amino acid sequence set forth in SEQ ID NO: 1, 2, 3, 6, 8, 10, 12, or 14; (c) a polypeptide comprising an amino acid sequence at least 95% identical to the amino acid sequence set forth in SEQ ID NO: 1, 2, 3, 6, 8, 10, 12, or 14; (d) a polypeptide comprising an amino acid sequence at least 98% identical to the amino acid sequence set forth in SEQ ID NO: 1, 2, 3, 6, 8, 10, 12, or 14; and (e) a polypeptide comprising the amino acid sequence set forth in SEQ ID NO: 1, 2, 3, 6, 8, 10, 12, or 14.

In addition to the methods described herein, certain embodiments of the present invention encompass compositions adapted for administration comprising a physiologically acceptable excipient and/or carrier and a thrombopoietically-effective concentration of a tyrosyl-tRNA synthetase polypeptide, as described herein, wherein the composition is capable of stimulating thrombopoiesis (i.e., increasing or maintaining the platelet count in a subject), stimulating the proliferation and/or differentiation of megakaryocytes, and/or stimulating the proliferation of neutrophils in a subject. In certain compositions, the tyrosyl-tRNA synthetase polypeptide comprises a mammalian tyrosyl-tRNA synthetase truncated at its C-terminus, as described above and elsewhere herein. In certain compositions, the tyrosyl-tRNA synthetase polypeptide comprises a mammalian tyrosyl-tRNA synthetase truncated at its N-terminus, as described above and elsewhere herein.

In certain embodiments, the thrombopoietic compositions described herein comprise a tyrosyl-tRNA synthetase polypeptide selected from: (a) a polypeptide comprising an amino acid sequence at least 80% identical to the amino acid sequence set forth in SEQ ID NO:2, wherein the alanine at position 341 is not substituted with a tyrosine; (b) a polypeptide comprising an amino acid sequence at least 90% identical to the amino acid sequence set forth in SEQ ID NO:2, wherein the alanine at position 341 is not substituted with a tyrosine; (c) a polypeptide comprising an amino acid sequence at least 95% identical to the amino acid sequence set forth in SEQ ID NO:2, wherein the alanine at position 341 is not substituted with a tyrosine; (d) a polypeptide comprising an amino acid sequence at least 98% identical to the amino acid sequence set forth in SEQ ID NO:2, wherein the alanine at position 341 is not substituted with a tyrosine; and (e) a polypeptide comprising the amino acid sequence set forth in SEQ ID NO:2.

In certain embodiments, the thrombopoietic compositions described herein comprise a tyrosyl-tRNA synthetase polypeptide selected from: (a) a polypeptide comprising an amino acid sequence at least 80% identical to the amino acid sequence set forth in SEQ ID NO: 1, 2, 3, 6, 8, 10, 12, or 14; (b) a polypeptide comprising an amino acid sequence at least 90% identical to the amino acid sequence set forth in SEQ ID NO: 1, 2, 3, 6, 8, 10, 12, or 14; (c) a polypeptide comprising an amino acid sequence at least 95% identical to the amino acid sequence set forth in SEQ ID NO: 1, 2, 3, 6, 8, 10, 12, or 14; (d) a polypeptide comprising an amino acid sequence at least 98% identical to the amino acid sequence set forth in SEQ ID NO: 1, 2, 3, 6, 8, 10, 12, or 14; and (e) a polypeptide comprising the amino acid sequence set forth in SEQ ID NO: 1, 2, 3, 6, 8, 10, 12, or 14.

In certain embodiments, the compositions of the present invention further comprise a second tyrosyl-tRNA synthetase polypeptide, including wherein the two tyrosyl-tRNA synthetase polypeptides form a dimer. In certain aspects, the dimer is a homodimer. In other aspects, the dimer is a heterodimer, such as a heterodimer between a full-length tyrosyl-tRNA synthetase polypeptide and a truncated tyrosyl-tRNA synthetase polypeptide. In certain embodiments, the compositions of the present invention further comprise a heterologous polypeptide, wherein the tyrosyl-tRNA synthetase polypeptide and the heterologous polypeptide form a heterodimer, such as a bi-functional heterodimer.

In certain embodiments, the thrombopoietic compositions provided herein comprise a physiologically acceptable excipient and/or carrier and a thrombopoietically-effective concentration of a chimeric tyrosyl-tRNA synthetase polypeptide, wherein the chimeric polypeptide comprises two or more biologically active fragments of a tyrosyl-tRNA synthetase polypeptide, wherein the two or more fragments comprise at least 10 contiguous amino acids of a YRS polypeptide, wherein the two or more fragments are linked to form a chimeric polypeptide, and wherein the chimeric tyrosyl-tRNA synthetase polypeptide is capable of stimulating thrombopoiesis and/or increasing the platelet count in a subject.

In certain embodiments, the thrombopoietic compositions provided herein comprise a physiologically acceptable excipient and/or carrier and a thrombopoietically-effective concentration of a chimeric tyrosyl-tRNA synthetase polypeptide, wherein the chimeric polypeptide comprises (a) one or more biologically active fragments of a tyrosyl-tRNA synthetase polypeptide, wherein the one or more fragments comprise at least 10 contiguous amino acids of a YRS polypeptide; and (b) one or more heterologous polypeptides, wherein the one or more fragments of (a) and the one or more heterologous polypeptides of (b) are linked to form a chimeric polypeptide, and wherein the chimeric polypeptide is capable of stimulating thrombopoiesis (i.e., increasing or maintaining the platelet count in a subject), stimulating the proliferation and/or differentiation of megakaryocytes, and/or stimulating the proliferation of neutrophils in a subject.

Certain embodiments relate to methods of stimulating proliferation and/or differentiation of early megakaryocyte progenitor cells, comprising incubating a culture of hematopoietic stem cells with a tyrosyl-tRNA synthetase polypeptide for a time sufficient to allow proliferation of the early megakaryocyte progenitor cells, thereby stimulating proliferation and/or differentiation of early megakaryocyte progenitor cells. In certain embodiments, the method is performed ex vivo or in vitro. In certain embodiments, the culture is obtained from bone marrow. In certain embodiments, the culture is obtained from cord blood. In certain embodiments, such methods further comprise administering the cells to a subject in need thereof.

Certain embodiments relate to methods of stimulating migration of a CXCR-2 expressing cell, comprising contacting the cell with a tyrosyl-tRNA synthetase polypeptide, thereby stimulating migration of the CXCR-2 expressing cell. In certain embodiments, the step of contacting the cell occurs in vitro or ex vivo. In certain embodiments, the step of contacting comprises administering to a subject in need thereof a composition comprising an effective concentration of a tyrosyl-tRNA synthetase polypeptide.

Certain embodiments relate to methods of reducing pulmonary inflammation, and/or its symptoms, in a subject, comprising administering to the subject an effective concentration of a tyrosyl-tRNA synthetase polypeptide, thereby reducing pulmonary inflammation, and/or its symptoms, in the subject. In certain embodiments, the subject has a chronic obstructive pulmonary disease (COPD). In certain embodiments, the administration of the tyrosyl-tRNA synthetase polypeptide is effective to achieve desensitization of circulating neutrophils to an allergen.

BRIEF DESCRIPTION OF THE DRAWINGS

FIG. 1 shows the full-length amino acid sequence of human tyrosyl-tRNA synthetase (SEQ ID NO:1).

FIG. 2 shows the amino acid sequence of a Y341A variant of full-length human tyrosyl-tRNA synthetase (SEQ ID NO:2).

FIG. 3 shows the amino acid sequence of a C-terminally truncated (amino acids 1-364) human tyrosyl-tRNA synthetase having thrombopoietic activity (SEQ ID NO:3).

FIG. 4 shows a polynucleotide sequence that encodes the full-length amino acid sequence of human tyrosyl-tRNA synthetase (SEQ ID NO:4).

FIG. 7 shows the amino acid sequence of the SP1 human tyrosyl-tRNA synthetase splice variant (SEQ ID NO:6), which represents an N-terminally truncated variant of the full-length wild-type YRS polypeptide sequence. The SP1 splice variant has 8 or 9 N-terminal amino acids that show no sequence similarity to the wild-type sequence. “X” represents any amino acid.

FIG. 8 shows the nucleic acid sequence (SEQ ID NO:7) that encodes the SP1 human tyrosyl-tRNA synthetase polypeptide of SEQ ID NO:6.

FIG. 9 shows the amino acid sequence of the SP2 human tyrosyl-tRNA synthetase splice variant (SEQ ID NO:8), which represents a C-terminally truncated variant of the full-length wild-type YRS polypeptide sequence. The SP2 variant has about 35 C-terminal amino acids that show no sequence similarity to the wild-type sequence. “X” represents any amino acid.

FIG. 10 shows the nucleic acid sequence (SEQ ID NO:9) that encodes the SP2 human tyrosyl-tRNA synthetase polypeptide of SEQ ID NO:8.

FIG. 11 shows the amino acid sequence of the SP3 human tyrosyl-tRNA synthetase splice variant (SEQ ID NO:10), which represents an N-terminally truncated variant of the full-length wild-type YRS polypeptide sequence.

FIG. 12 shows the nucleic acid sequence (SEQ ID NO:11) that encodes the SP3 human tyrosyl-tRNA synthetase polypeptide of SEQ ID NO:10.

FIG. 13 shows the amino acid sequence of the SP4 human tyrosyl-tRNA synthetase splice variant (SEQ ID NO:12), which represents an N-terminally truncated variant of the full-length wild-type YRS polypeptide sequence.

FIG. 14 shows the nucleic acid sequence (SEQ ID NO:13) that encodes the SP4 human tyrosyl-tRNA synthetase polypeptide of SEQ ID NO:12.

FIG. 15 shows the amino acid sequence of the SP5 human tyrosyl-tRNA synthetase splice variant (SEQ ID NO:14), which represents an N-terminally truncated variant of the full-length wild-type YRS polypeptide sequence. The SP5 variant has about 8 N-terminal amino acids that show no similarity to the wild-type sequence. “X” represents any amino acid.

FIG. 16 shows the nucleic acid sequence (SEQ ID NO:15) that encodes the SP5 human tyrosyl-tRNA synthetase polypeptide of SEQ ID NO:14.

FIG. 18 provides the NCBI annotation of the cDNA sequences for human tyrosyl-tRNA synthetase splice variants SP1 to SP5.

FIGS. 26(A)-26(C) show the effects of tyrosyl-tRNA synthetase polypeptides on megakaryocyte progenitor cells in bone marrow cell cultures, as measured by the number of colonies (see Example 10). FIG. 26(A) shows the stimulatory effects of YRS polypeptides on colony formation of primitive lineage-restricted progenitors, or early progenitors, and FIGS. 26(B) and (C) show the inhibitory effects of YRS polypeptides on relatively mature intermediate progenitors (B) and late progenitors (C), respectively.

DETAILED DESCRIPTION

Figure 5A:
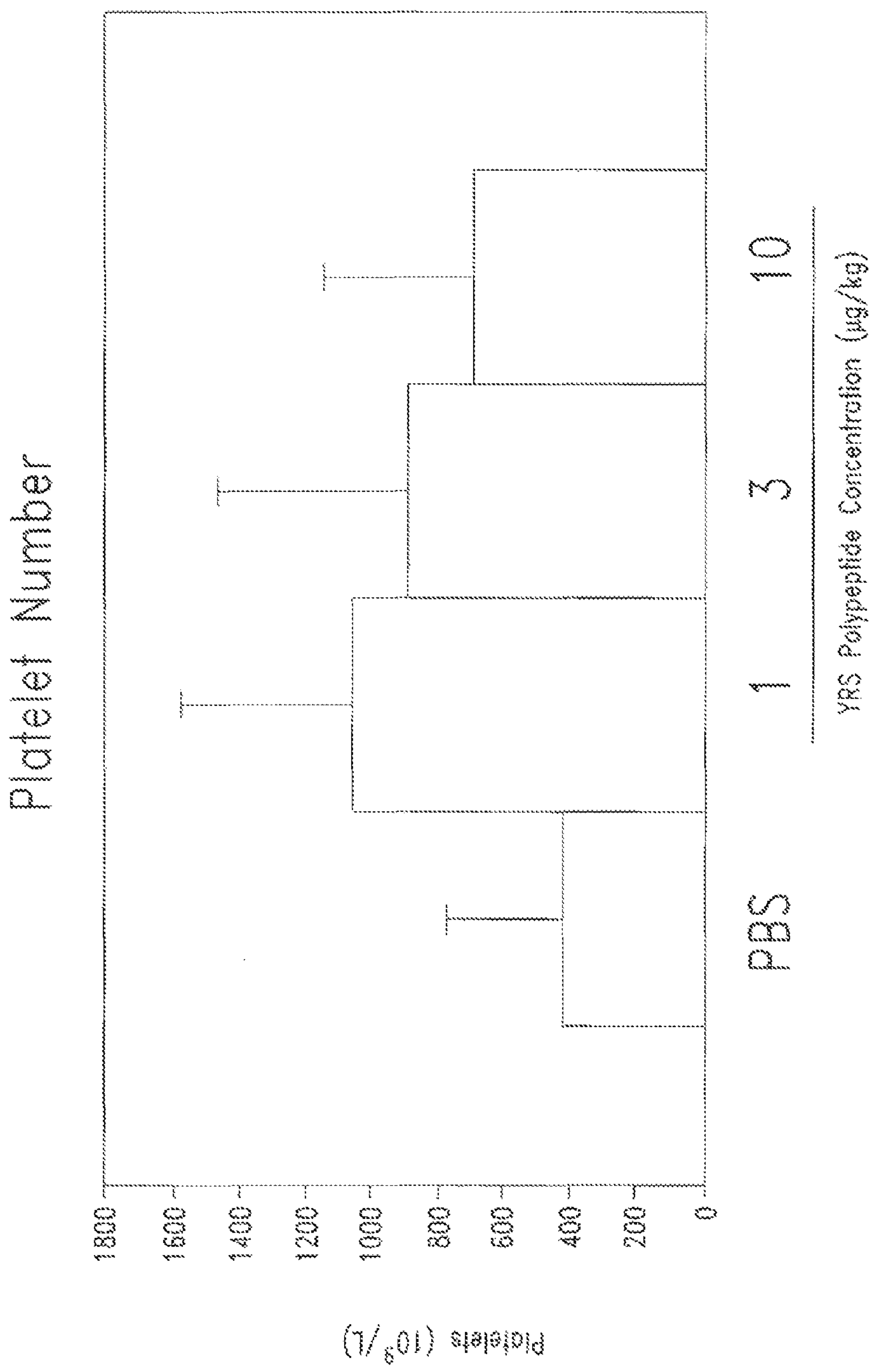
FIGS. 5(*a*) and 5(*b*) show the in vivo effects on platelet number following administration of a truncated human tyrosyl-tRNA synthetase. For FIG. 5(*a*), mice were injected subcutaneously twice daily for seven days with 1, 3 and 10 μg/kg a C-terminally truncated tyrosyl-tRNA synthetase polypeptide (SEQ ID NO:3) having an eight amino acid C-terminal tag, L-E-H-H-H-H-H-H (SEQ ID NO:5), and platelet count was determined at the end of the study. For FIG. 5(*b*), mice were injected subcutaneously twice daily for 7 days with 3 μg/kg of the same C-terminally truncated polypeptide as in FIG. 5(*a*), and platelet count was determined at the end of the study.

The present invention relates to the unexpected discovery that tyrosyl-tRNA synthetase (YRS) polypeptides, including truncations and variants thereof, are capable of mimicking and stimulating the normal thrombopoiesis process, and, thus, possess therapeutically beneficial thrombopoietic activity. Certain embodiments of the present invention, therefore, relate to the use of YRS polypeptides to stimulate the natural thrombopoiesis process, and thereby increase platelet production in subjects in need thereof, such as subjects suffering from a condition associated with thrombocytopenia (i.e., reduced platelet count). Advantages of the use of YRS polypeptides over other treatments include, for example, a different mechanism of action than traditional treatments, synergism with thrombopoietin signaling, higher potency, and the benefits associated with using a de-immunized molecule (e.g., no impact of potential adverse immune response against thrombopoietin). Other advantages will be apparent to a person skilled in the art.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); Oligonucleotide Synthesis (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); *A Practical Guide to Molecular Cloning* (B. Perbal, ed., 1984).

All publications, patents and patent applications cited herein are hereby incorporated by reference in their entirety.

DEFINITIONS

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

The term "biologically active fragment", as applied to fragments of a reference polynucleotide or polypeptide sequence, refers to a fragment that has at least about 0.1, 0.5, 1, 2, 5, 10, 12, 14, 16, 18, 20, 22, 24, 26, 28, 30, 35, 40, 45, 50, 55, 60, 65, 70, 75, 80, 85, 90, 95, 96, 97, 98, 99, 100, 110, 120, 150, 200, 300, 400, 500, 600, 700, 800, 900, 1000% or more of the activity of a reference sequence. Included within the scope of the present invention are biologically active fragments of at least about 18, 19, 20, 21, 22, 23, 24, 25, 26, 27, 28, 29, 30, 40, 50, 60, 70, 80, 90, 100, 120, 140, 160, 180, 200, 220, 240, 260, 280, 300, 320, 340, 360, 380, 400, or more contiguous nucleotides or amino acid residues in length, including all integers in between, which comprise or encode a thrombopoietic activity of a reference polynucleotide or polypeptide, such as the reference polypeptide sequences of SEQ ID NOS: 1, 2, 3, 6, 8, 10, 12 and 14, or the reference nucleotide sequences of SEQ ID NOS: 4, 7, 9, 11, 13, and 15. Particular examples of biologically active fragments include, but are not limited to, C-terminally truncated tyrosyl-tRNA synthetase polypeptides comprising or consisting of amino acids 1-343, amino acids 1-344, amino acids 1-350, amino acids 1-353, or amino acids 1-364 of the amino acid sequence set forth in SEQ ID NO:1, in addition to the polypeptides of SEQ ID NOS:3 and 6. Additional examples of biologically active fragments include, but are not limited to, N-terminally truncated tyrosyl-tRNA synthetase polypeptides comprising or consisting of the amino acid sequences set forth in SEQ ID NOS: 6, 10, 12, and 14. Representative biologically active fragments generally participate in an interaction, e.g., an intramolecular or an inter-molecular interaction. An inter-molecular interaction can be a specific binding interaction or an enzymatic interaction. An inter-molecular interaction can be between a YRS polypeptide and target molecule, such as a target molecule involved in regulating the process of thrombopoiesis. Biologically active fragments of a YRS polypeptide include polypeptide fragments comprising amino acid sequences with sufficient similarity or identity to, or which are derived from, the amino acid sequences of any of SEQ ID NOS: 1, 2, 3, 6, 8, 10, 12 or 14, including thrombopoietically effective portions thereof, or are encoded by a nucleotide sequences of SEQ ID NOS: 4, 7, 9, 11, 13, and 15.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties (e.g., pegylation) or by post-translational modification techniques as would be understood in the art. The term "derivative" also includes within its scope alterations that have been made to a parent sequence including additions or deletions that provide for functionally equivalent molecules.

As used herein, the terms "function" and "functional" and the like refer to a biological, enzymatic, or therapeutic function.

By "gene" is meant a unit of inheritance that occupies a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide", as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell; i.e., it is not associated with in vivo substances.

By "obtained from" is meant that a sample such as, for example, a polynucleotide extract or polypeptide extract is isolated from, or derived from, a particular source of the subject. For example, the extract can be obtained from a tissue or a biological fluid isolated directly from the subject.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

The term "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e., the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e., the genes from which it is derived.

The recitation "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Polynucleotide variants include, for example, polynucleotides having at least 50% (and at least 51% to at least 99% and all integer percentages in between) sequence identity with the sequence set forth in SEQ ID NO:4, or portions thereof that encode a biologically active fragment of a thrombopoietic tyrosyl-tRNA synthetase polypeptide. The terms "polynucleotide variant" and "variant" also include naturally occurring allelic variants.

"Polypeptide," "polypeptide fragment," "peptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers.

The terms "tyrosine RNA synthetase" and "tyrosyl-tRNA synthetase" are used interchangeably herein, and refer to a "YRS" polypeptide of the invention.

The recitations "YRS polypeptides" "YRS polypeptide fragments," "truncated YRS polypeptides" or "variants thereof" encompass, without limitation, polypeptides having the amino acid sequence that shares at least 50% (and at least 51% to at least 99% and all integer percentages in between) sequence identity with a reference sequence set forth in any one of SEQ ID NOS: 1, 2, 3, 6, 8, 10, 12, or 14, including biologically active fragments thereof, such as fragments having at least 10, 20, 30, 40, 50, 60, 70, 80, 90, 100, 120, 140, 160, 180, 200, or more contiguous amino acids of the reference sequences, including all integers in between. These recitations further encompass natural allelic variation of YRS polypeptides that may exist and occur from one genus or species to another.

YRS polypeptides, including truncations and/or variants thereof, encompass polypeptides that exhibit at least about 10%, 20%, 30%, 40%, 50%, 60%, 70%, 80%, 90%, 100%, 110%, 120%, 130%, 140%, 150%, 200%, 300%, 400%, 500%, 600%, 700%, 800%, 900%, 1000% or more of the specific biological activity of a reference YRS polypeptide (i.e., such as having a thrombopoietic activity in a subject or in vitro). For purposes of the present application, YRS-related biological activity may be quantified, for example, by measuring the ability of a YRS polypeptide to either increase the platelet count in a subject, or to increase the megakaryocyte number in a subject (see, e.g., Example 1). In addition, suitable animal models for measuring human platelet production are described in Suzuki et al., *European Journal of Haemotology* 78:123-130, 2007, herein incorporated by reference. Suitable in vitro models for measuring thrombopoietic activity are described in Example 2, and further include assaying megakaryocyte colony formation, as exemplified in Dessypris et al., *Exp Hematol.* 18:754-7, 1990. YRS polypeptides, including truncations and/or variants thereof, having substantially reduced biological activity relative to a wild-type reference YRS polypeptide are those that exhibit less than about 25%, 10%, 5% or 1% of the specific activity of wild-type YRS.

The recitation polypeptide "variant" refers to polypeptides that are distinguished from a reference polypeptide by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The present invention contemplates the use in the methods described herein of variants of full-length YRS polypeptides (e.g., a full-length polypeptide having a Y341A substitution), truncated fragments of full-length YRS polypeptides, variants of truncated fragments, as well as their related biologically active fragments. Typically, biologically active fragments of a YRS polypeptide may participate in an interaction, for example, an intra-molecular or an inter-molecular interaction. An inter-molecular interaction can be a specific binding interaction or an enzymatic interaction (e.g., the interaction can be transient and a covalent bond is formed or broken). Biologically active fragments of a YRS polypeptide include peptides comprising amino acid sequences sufficiently similar to, or derived from, the amino acid sequences of a (putative) full-length YRS polypeptide sequence, such as SEQ ID NO:1, or portions thereof, such as the polypeptides of SEQ ID NOS: 3, 6, 8, 10, 12, and 14. Typically, biologically active fragments comprise a domain or motif with at least one activity of a YRS polypeptide and may include one or more (and in some cases all) of the various active domains, and include fragments having a thrombopoietic activity. In some cases, biologically active fragments of a YRS polypeptide have a biological activity (e.g., thrombopoietic activity) that is unique to the particular, truncated fragment, such that the full-length YRS polypeptide may not have that activity. In certain cases, the biological activity may be revealed by separating the biologically active YRS polypeptide fragment from the other full-length YRS polypeptide sequences, or by altering certain residues (e.g., Y341A) of the full-length YRS wild-type polypeptide sequence to unmask the thrombopoietically active domains. A biologically active fragment of a truncated YRS polypeptide can be a polypeptide fragment which is, for example, 10, 11, 12, 13, 14, 15, 16, 17, 18, 19, 20, 21, 22, 23, 24, 25, 26, 27, 28, 29, 30, 40, 50, 60, 70, 80, 90, 100, 110, 120, 130, 140, 150, 160, 170, 180, 190, 200, 220, 240, 260, 280, 300, 320, 340, 360, 380, 400 or more contiguous amino acids, including all integers in between, of the amino acid sequences set forth in any one of SEQ ID NOS: 1, 2, 3, 6, 8, 10, 12, or 14. In certain embodiments, a biologically active fragment comprises a thrombopoiesis stimulating sequence, domain, or motif. Suitably, the biologically-active fragment has no less than about 1%, 10%, 25%, 50% of an activity of the wild-type polypeptide from which it is derived.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gin, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence", "comparison window", "sequence identity", "percentage of sequence identity" and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997*, Nucl. Acids Res.* 25:3389. A detailed discussion of sequence analysis can be found in Unit 19.3 of Ausubel et al., "Current Protocols in Molecular Biology", John Wiley & Sons Inc, 1994-1998, Chapter 15.

A "subject," as used herein, includes any animal that exhibits a symptom, or is at risk for exhibiting a symptom, that can be treated with a thrombopoietic YRS polypeptide of the invention. Suitable subjects (patients) include laboratory animals (such as mouse, rat, rabbit, or guinea pig), farm animals, and domestic animals or pets (such as a cat or dog). Non-human primates and, preferably, human patients, are included. Typical subjects include animals that exhibit, or are at risk for exhibiting, aberrant amounts of one or more physiological activities that can be modulated by a thrombopoietic polypeptide, such as decreased or reduced platelet counts (i.e., thrombocytopenia). Typically, a subject having thrombocytopenia, or a "reduced" platelet count, as used herein, refers to a subject having a decrease in the platelet count to about 100,000/$mm^3$ or lower, about 110,000/$mm^3$ or lower, about 120,000/$mm^3$ or lower, about 130,000/$mm^3$ or lower, about 140,000/$mm^3$ or lower, or about 150,000/$mm^3$ or lower, as compared to a normal platelet count. As used herein, a "normal" platelet count generally ranges from about 150,000/$mm^3$ to about 450,000/$mm^3$ in a subject. As one example, a "subject" may also be about to undergo, is undergoing, or has undergone, a transplant procedure, such as a stem cell or bone marrow transplant. A subject may also have a pulmonary disorder or disease, such as chronic obstructive pulmonary disease (COPD), and/or be suffering from pulmonary inflammation.

"Thrombopoiesis," as used herein, refers to the formation of blood platelets, or thrombocytes.

A "thrombopoietically-effective concentration" of a tyrosyl-tRNA synthetase polypeptide, as described herein, refers to an amount that is capable of "treating" a subject, such as by being "effective" to stimulate or enhance thrombopoiesis, as typically measured by increased platelet levels, maintained platelet levels, increased megakaryocyte numbers, and/or increased neutrophil production.

A "megakaryocyte" refers generally to a bone marrow cell that is responsible for the production of blood thrombocytes (i.e., platelets), which are necessary for normal blood clotting. Megakaryocytes typically account for 1 out of 10,000 bone marrow cells. Megakaryocytes are derived from pluripotent hematopoietic stem cell precursor cells in the bone marrow. Thrombopoietin (TPO) is the primary signal for megakaryocyte production, i.e., TPO is sufficient but not absolutely necessary for inducing differentiation of progenitor cells in the bone marrow towards a final megakaryocyte phenotype. Other molecular signals for megakaryocyte differentiation include GM-CSF, IL-3, IL-6, IL-11, chemokines (SDF-1; FGF-4), and erythropoietin.

Megakaryocytes are believed to develop through the following lineage: CFU-Me (pluripotential hemopoietic stem cell or hemocytoblast)→megakaryoblast→promegakaryocyte→megakaryocyte. At the megakaryoblast stage, the cell loses its ability to divide, but is still able to replicate its DNA and continue development, becoming polyploid. Upon maturation, megakaryocytes begin the process of producing platelets. Thrombopoietin plays a role in inducing the megakaryocyte to form small proto-platelet processes, or cytoplasmic internal membranes for storing platelets prior to release. Upon release, each of these proto-platelet processes can give rise to 2000-5000 new platelets. Overall, about ⅔ of the newly-released platelets will remain in circulation and about ⅓ will be sequestered by the spleen. After releasing the platelets, the remaining cell nucleus typically crosses the bone marrow barrier to the blood and is consumed in the lung by alveolar macrophages.

A "neutrophil," or neutrophil granulocyte, refers generally to an abundant type of white blood cells in humans, which, together with basophils and eosinophils, form part of the polymorphonuclear cell family (PMNs). Neutrophils can be readily identified according to their unique staining characteristics on hematoxylin and eosin (H&E) histological or cytological preparations. Neutrophils are normally found in the blood stream, but are one of the first group of inflammatory cells to migrate toward inflammation sites during the beginning (i.e., acute) phase of inflammation, mainly as a result of infection or cancer. Typically, neutrophils first migrate through the blood vessels, and then through interstitial tissues, following chemical signals (e.g., interleukin-8 (IL-8), interferon-gamma (IFN-gamma), and C5a) that originate at the site of inflammation. "Neutropenia" refers to the presence of low neutrophil counts, which can result from a congenital (genetic) disorder, it can develop due to other conditions, as in the case of aplastic anemia or some kinds of leukemia. Certain medications, such as chemotherapeutics, may also cause neutropenia. Neutropenia predisposes heavily for infection. Neutropenia can also result from the colonization of intracellular neutrophilic parasites.

By "enhance" or "enhancing," or "increase" or "increasing," or "stimulate" or "stimulating," refers generally to the ability of one or agents or compositions to produce or cause a greater physiological response (i.e., downstream effects) in a cell, as compared to the response caused by either no YRS polypeptide or a control molecule/composition. A measurable physiological response may include greater cell growth, expansion, or migration, among others apparent from the understanding in the art and the description herein. Among other methods known in the art, in vitro colony formation assays represent one way to measure cellular responses to agents provided herein. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1), e.g., 1.5, 1.6, 1.7. 1.8, etc.) the amount produced by no YRS polypeptide (the absence of an agent) or a control composition.

The term "reduce" may relate generally to the ability of one or more YRS polypeptides of the invention to "decrease" a relevant physiological or cellular response, such as a symptom of a disease or condition (e.g., pulmonary inflammation, etc.), as measured according to routine techniques in the diagnostic art. One specific example of a relevant response includes the migration of immune cells (e.g., neutrophils) to certain tissues, such as the lung. Other relevant physiological or cellular responses (in vivo or in vitro) will be apparent to persons skilled in the art. A "decrease" in a response may be statistically significant as compared to the response produced by no YRS polypeptide or a control composition.

"Migration" refers to cellular migration, a process that can be measured according to routine in vitro assays, as described herein and known in the art (see, e.g., Example 8). Migration also refers to in vivo migration, such as the migration of cells from one tissue to another tissue (e.g., from bone marrow to peripheral blood, or from peripheral blood to lung tissue), or from a site within one tissue to another site within the same tissue. Migration in vivo (e.g., chemotaxis) often occurs in a response to infection or damaged/irritated tissue.

"Differentiation" refers to the process by which a less specialized (e.g., pluripotent, totipotent, multipotent, etc.) cell becomes a more specialized cell type.

"Desensitization" refers generally to the reduction or elimination of an organism's negative (pathological) immune reaction to a substance or stimulus, such as an allergen or irritant, including foreign antigens as well as "self-antigens." For instance, certain pulmonary diseases or conditions are associated with a negative reaction to foreign irritants such as smoke, such that desensitizing neutrophils to these irritants may prevent (i.e., reduce the risk of developing) or reduce such diseases or conditions, and/or their symptoms.

"Treatment" or "treating," as used herein, includes any desirable effect on the symptoms or pathology of a disease or condition associated with thrombocytopenia (i.e., reduced platelet levels), or a risk of developing thrombocytopenia, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any animal in need, including primates, in particular humans, and other mammals such as equines, cattle, swine and sheep; and poultry and pets in general. Exemplary markers of clinical improvement include either increased platelet counts, maintenance of normal platelet counts, and/or increased megakaryocyte numbers, following administration of a thrombopoietic YRS polypeptide, as described herein.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extra-chromosomal entity, the replication of which is independent of chromosomal replication, e.g., a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably one which is operably functional in a bacterial cell. The vector can also include a selection marker such as an antibiotic resistance gene that can be used for selection of suitable transformants.

The terms "wild-type" and "naturally occurring" are used interchangeably to refer to a gene or gene product that has the characteristics of that gene or gene product when isolated from a naturally occurring source. A wild-type gene or gene product (e.g., a polypeptide) is that which is most frequently observed in a population and is thus arbitrarily designed the "normal" or "wild-type" form of the gene.

Thrombopoietic Tyrosyl-tRNA Polypeptides and Variants Thereof

The present invention relates in part to the unexpected observation that certain tyrosyl-tRNA synthetase polypeptides, including truncations and/or variants thereof, mimic and stimulate the natural thrombopoietic process in vivo. Accordingly, thrombopoietic polypeptides of the present invention include a full-length tyrosyl-tRNA synthetase polypeptide, in addition to any biologically active fragment, or variant or modification thereof, of a tyrosyl-tRNA synthetase polypeptide, wherein the polypeptide is capable of stimulating thrombopoiesis (i.e., platelet formation), megakaryocyte proliferation and/or differentiation, and/or neutrophil proliferation in a subject or in vitro.

Aminoacyl-tRNA synthetases, such as tyrosyl-tRNA synthetase, typically catalyze the aminoacylation of tRNA by their cognate amino acid. Because of their central role in linking amino acids with nucleotide triplets contained in tRNAs, aminoacyl-tRNA synthetases are thought to be among the first proteins that appeared in evolution. Tyrosyl-tRNA synthetases in particular belong to the class I tRNA synthetase family, which has two highly conserved sequence motifs at the active site, HIGH and KMSKS. Class I tRNA synthetases aminoacylate at the 2'-OH of an adenosine nucleotide, and are usually monomeric or dimeric (one or two subunits, respectively).

The human tyrosyl-tRNA synthetase is composed of three domains: 1) an amino-terminal Rossmann fold domain that is responsible for formation of the activated E•Tyr-AMP intermediate and is conserved among bacteria, archeae, and eukaryotes; 2) a tRNA anticodon recognition domain that has not been conserved between bacteria and eukaryotes; and 3) a carboxyl-terminal domain that is unique to the human tyrosyl-tRNA synthetase, and whose primary structure is 49% identical to the putative human cytokine endothelial monocyte-activating protein II, 50% identical to the carboxyl-terminal domain of methionyl-tRNA synthetase from *Caenorhabditis elegans*, and 43% identical to the carboxyl-terminal domain of Arc1p from *Saccharomyces cerevisiae.*

The first two domains of the human tyrosyl-tRNA synthetase are 52, 36, and 16% identical to tyrosyl-tRNA synthetases from *S. cerevisiae, Methanococcus jannaschii*, and *Bacillus stearothermophilus*, respectively. Nine of fifteen amino acids known to be involved in the formation of the tyrosyl-adenylate complex in *B. stearothermophilus* are conserved across all of the organisms, whereas amino acids involved in the recognition of $tRNA^{Tyr}$ are not conserved. Kinetic analyses of recombinant human and *B. stearothermophilus* tyrosyl-tRNA synthetases expressed in *Escherichia coli* indicate that human tyrosyl-tRNA synthetase aminoacylates human but not *B. stearothermophilus* $tRNA^{Tyr}$, and vice versa. It is believed that the carboxyl-terminal domain of human tyrosyl-tRNA synthetase evolved from gene duplication of the carboxyl-terminal domain of methionyl-tRNA synthetase and may direct tRNA to the active site of the enzyme.

Figure 17:
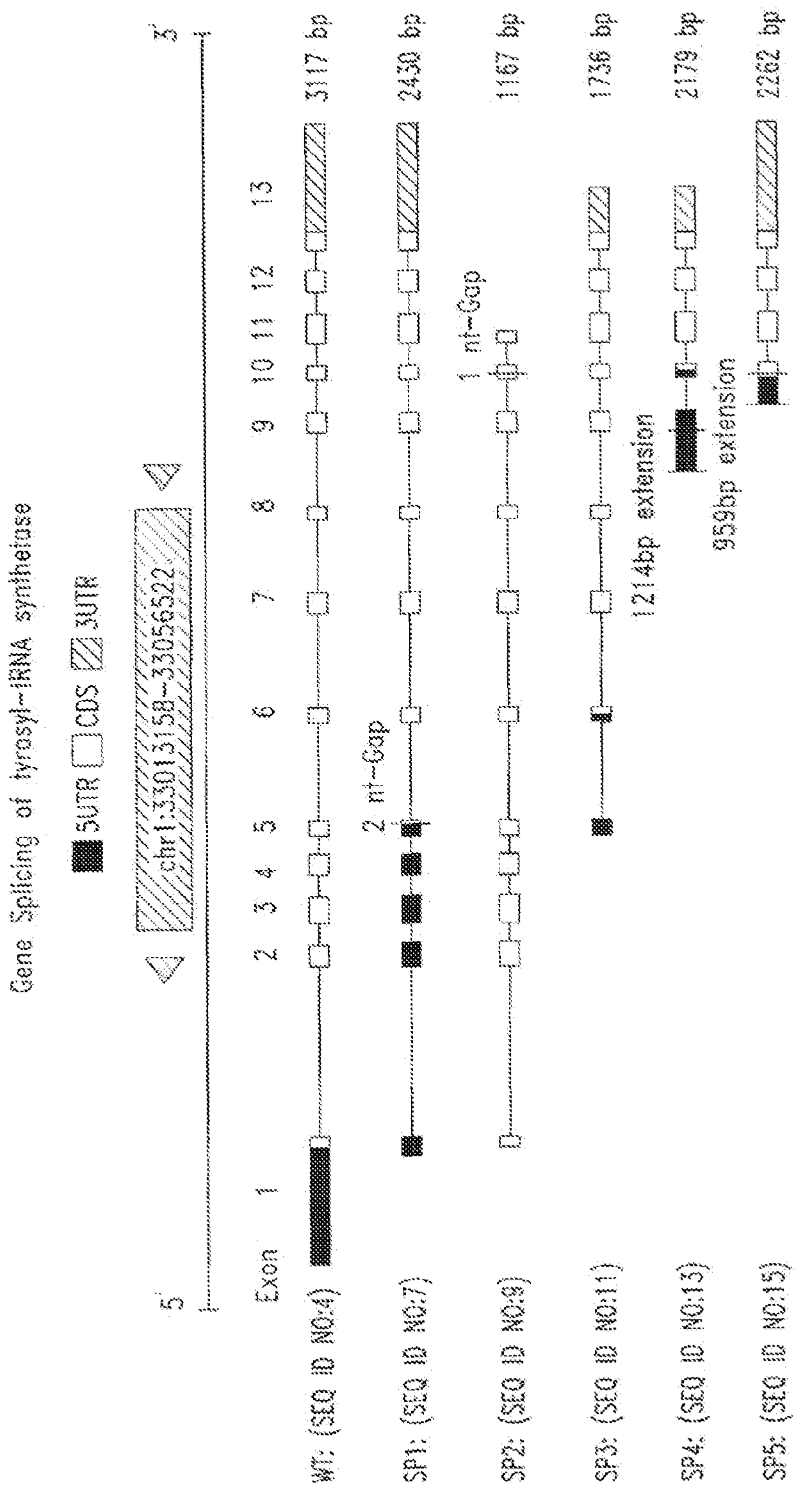
FIG. 17 illustrates the alternate gene splicing of wild-type (WT) human tyrosyl-tRNA synthetase, as represented by the cDNA sequence of alternate splice variants SP1 to SP5.
Figure 19:
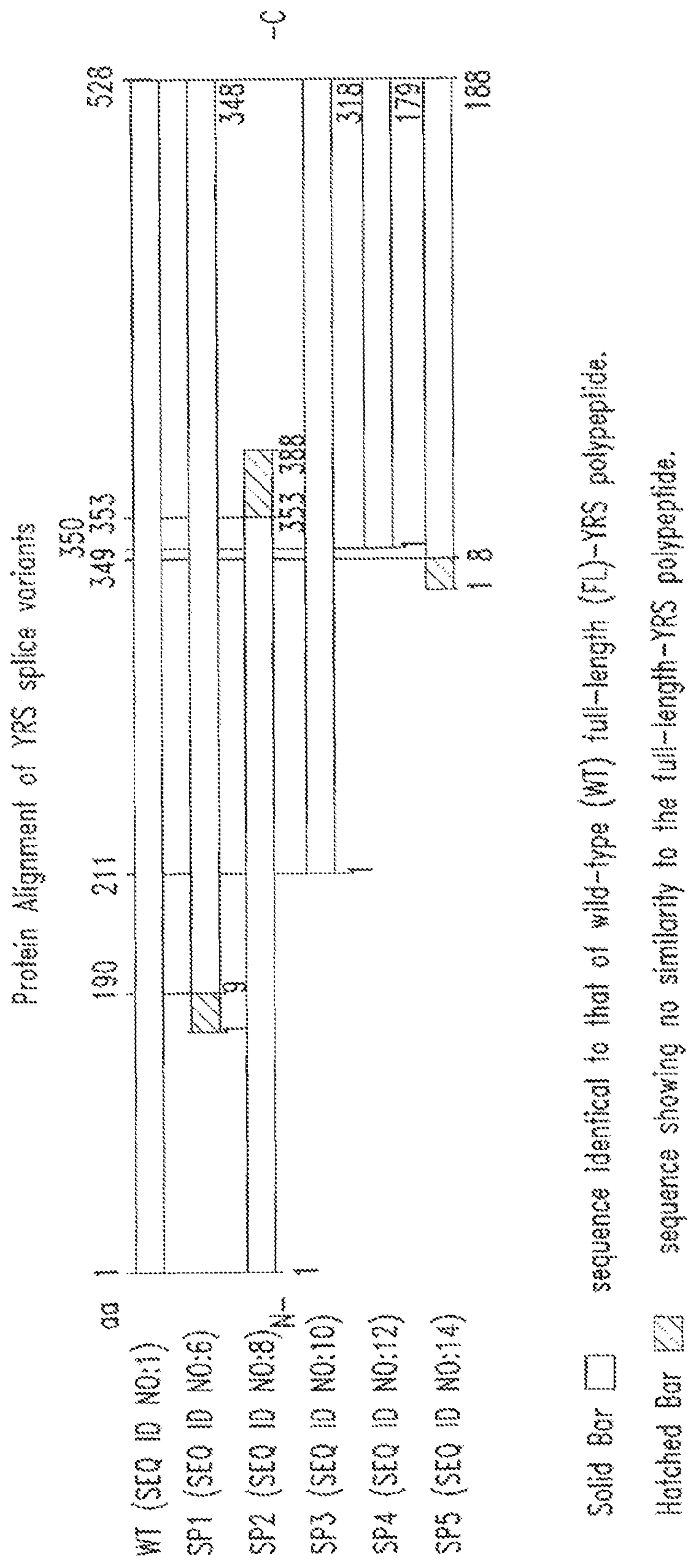
FIG. 19 depicts the protein sequence alignment of the predicted and reported open reading frames for the SP1 to SP5 YRS polypeptides as compared to the full-length human YRS polypeptide.

Biological fragments of eukaryotic tyrosyl-tRNA synthetases connect protein synthesis to cell-signaling pathways, such as thrombopoiesis. These fragments may be produced naturally by either alternative splicing or proteolysis. For example, as provided in the present invention, the pro-thrombopoietic N-terminal fragment mini-YRS is capable of stimulating thrombopoiesis in vivo. In addition, certain mutations in the full-length YRS polypeptide sequence confer increased thrombopoietic activity on the wild-type reference sequence (e.g., Y341A). Examples of truncated splice variants of the full-length YRS polypeptide sequence include the SP1-SP5 polypeptides described in FIGS. 17-19.

The structure of human mini-YRS (i.e., SEQ ID NO:3; or mini-Tyr), which contains both the catalytic and the anticodon recognition domain, has been reported to a resolution of 1.18 Å. Whereas the catalytic domains of the human and bacterial enzymes superimpose, the spatial disposition of the anticodon recognition domain relative to the catalytic domain is unique in mini-YRS relative to the bacterial orthologs. Without wishing to be bound by any one theory, the unique orientation of the anticodon-recognition domain may explain why the fragment mini-YRS is more active in various cell-signaling pathways.

Accordingly, embodiments of the present invention contemplate the use of compositions comprising thrombopoietic YRS polypeptides, including truncated, variant and/or modified polypeptides thereof, for stimulating thrombopoiesis in a subject. Variant proteins encompassed by the present application are biologically active, that is, they continue to possess the thrombopoietic activity of a reference YRS polypeptide sequence (e.g., SEQ ID NOS: 1, 2, 3, 6, 8, 10, 12, and 14). Such variants may result from, for example, genetic polymorphism or from human manipulation. Biologically active variants of a reference YRS polypeptide fragment will have at least 40%, 50%, 60%, 70%, generally at least 75%, 80%, 85%, usually about 90% to 95% or more, and typically about 98% or more sequence similarity or identity with the amino acid sequence for a reference protein as determined by sequence alignment programs described elsewhere herein using default parameters. A biologically active variant of a reference YRS polypeptide may differ from that protein generally by as much 200, 100, 50 or 20 amino acid residues or suitably by as few as 1-15 amino acid residues, as few as 1-10, such as 6-10, as few as 5, as few as 4, 3, 2, or even 1 amino acid residue. In some embodiments, a YRS polypeptide differs from the reference sequences in SEQ ID NOS: 1, 2, 3, 6, 8, 10, 12, and 14 by at least one but by less than 15, 10 or 5 amino acid residues. In other embodiments, it differs from the reference sequences in SEQ ID NOS: 1, 2, 3, 6, 8, 10, 12, and 14 by at least one residue but less than 20%, 15%, 10% or 5% of the residues.

A YRS polypeptide may be altered in various ways including amino acid substitutions, deletions, truncations, and insertions. Methods for such manipulations are generally known in the art. For example, amino acid sequence variants of a truncated and/or variant YRS polypeptide can be prepared by mutations in the DNA. Methods for mutagenesis and nucleotide sequence alterations are well known in the art. See, for example, Kunkel (1985*, Proc. Natl. Acad. Sci. USA*. 82: 488-492), Kunkel et al., (1987*, Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.). Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of YRS polypeptides. Recursive ensemble mutagenesis (REM), a technique which enhances the frequency of functional mutants in the libraries, can be used in combination with the screening assays to identify YRS polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Thrombopoietically active truncated and/or variant YRS polypeptides may contain conservative amino acid substitutions at various locations along their sequence, as compared to a reference YRS amino acid sequence (e.g., SEQ ID NOS: 1, 2, 3, 6, 8, 10, 12, or 14). A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices (e.g., PAM120 matrix and PAM250 matrix as disclosed for example by Dayhoff et al., (1978), A model of evolutionary change in proteins. Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (*Science,* 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behaviour.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table A.

TABLE A

Amino acid sub-classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant YRS polypeptide can readily be determined by assaying its activity, as described herein (see, e.g., Examples 1 and 2). Conservative substitutions are shown in Table B under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity.

TABLE B

Exemplary Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

Thus, a predicted non-essential amino acid residue in a truncated and/or variant YRS polypeptide is typically replaced with another amino acid residue from the same side chain family. Alternatively, mutations can be introduced randomly along all or part of a YRS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the wild-type sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of wild-type. An "essential" amino acid residue is a residue that, when altered from the wild-type sequence of a reference truncated YRS polypeptide, results in abolition of an activity of the parent molecule such that less than 20% of the wild-type activity is present. For example, such essential amino acid residues include those that are conserved in YRS polypeptides across different species, including those sequences that are conserved in the thrombopoiesis stimulating-binding site(s) or motif(s) of YRS polypeptides from various sources.

Accordingly, the present invention also contemplates variants of the naturally-occurring YRS polypeptide sequences or their biologically-active fragments, wherein the variants are distinguished from the naturally-occurring sequence by the addition, deletion, or substitution of one or more amino acid residues. In general, variants will display at least about 30, 40, 50, 55, 60, 65, 70, 75, 80, 85, 90, 91, 92, 93, 94, 95, 96, 97, 98, 99% similarity or sequence identity to a reference YRS polypeptide sequences, for example, as set forth in SEQ ID NOS: 1, 2, 3, 6, 8, 10, 12, and 14. Moreover, sequences differing from the native or parent sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100 or more amino acids but which retain the properties of a parent or reference YRS polypeptide sequence are contemplated. In certain embodiments, the C-terminal or N-terminal region of any of SEQ ID NOS: 1, 2, 3, 6, 8, 10, 12, or 14 may be truncated by 1, 2, 3, 4, 5, 6, 7, 8, 9, 10, 15, 20, 25, 30, 35, 40, 45, 50, 60, 70, 80, 90, 100, 150, 200, 250, or more amino acids, including all integers in between (e.g., 101, 102, 103, 104, 105), so long as the truncated YRS polypeptide is capable of stimulating thrombopoiesis (i.e., platelet formation), megakaryocyte proliferation and/or differentiation, and/or neutrophil proliferation in a subject or in vitro.

In some embodiments, variant polypeptides differ from a reference YRS sequence by at least one but by less than 50, 40, 30, 20, 15, 10, 8, 6, 5, 4, 3 or 2 amino acid residue(s). In other embodiments, variant polypeptides differ from the corresponding sequences of SEQ ID NOS: 1, 2, 3, 6, 8, 10, 12, or 14 by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution.

In certain embodiments, a variant polypeptide includes an amino acid sequence having at least about 50%, 55%, 60%, 65%, 70%, 75%, 80%, 85%, 90%, 91%, 92%, 93%, 94% 95%, 96%, 97%, 98% or more sequence identity or similarity to a corresponding sequence of a YRS polypeptide as, for example, set forth in SEQ ID NOS: 1, 2, 3, 6, 8, 10, 12, or 14, and has the ability to stimulate thrombopoiesis in a subject, stimulate the proliferation and/or differentiation of megakaryocytes in a subject, and/or stimulate the proliferation of neutrophils in a subject. Examples of YRS polypeptide variants include, but are not limited to, a full-length YRS polypeptide, or a truncation or splice variant thereof, having one or more amino acid substitutions selected from an R93Q substitution, an I14L substitution, an N17G substitution, an L271 substitution, an A85S substitution, and a V156L substitution, in addition to combinations thereof. Particular examples of YRS polypeptide variants include, but are not limited to, a YRS polypeptide having amino acids 1-364 of SEQ ID NO:1 with an R93Q substitution, a YRS polypeptide having amino acids 1-353 of SEQ ID NO:1 with an I14L substitution, a YRS polypeptide having amino acids 1-353 of SEQ ID NO:1 with an N17G substitution, a YRS polypeptide having amino acids 1-353 of SEQ ID NO:1 with an L27I substitution, a YRS polypeptide having amino acids 1-353 of SEQ ID NO:1 with an A85S substitution, and a YRS polypeptide having amino acids 1-353 of SEQ ID NO:1 with a V156L substitution.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, *Cabios*, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215:

403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res,* 25: 3389-3402). When utilizing BLAST and Gapped BLAST programs, the default parameters of the respective programs (e.g., XBLAST and NBLAST) can be used.

Variants of a YRS polypeptide can be identified by screening combinatorial libraries of mutants of a YRS polypeptide. Libraries or fragments e.g., N terminal, C terminal, or internal fragments, of YRS protein coding sequence can be used to generate a variegated population of fragments for screening and subsequent selection of variants of a YRS polypeptide.

Methods for screening gene products of combinatorial libraries made by point mutation or truncation, and for screening cDNA libraries for gene products having a selected property are known in the art. Such methods are adaptable for rapid screening of the gene libraries generated by combinatorial mutagenesis of YRS polypeptides.

The present invention also contemplates the use of YRS chimeric or fusion proteins for stimulating thrombopoiesis. As used herein, a YRS "chimeric protein" or "fusion protein" includes a YRS polypeptide or polypeptide fragment linked to either another YRS-polypeptide (e.g., to create multiple fragments), to a non-YRS polypeptide, or to both. A "non-YRS polypeptide" refers to a "heterologous polypeptide" having an amino acid sequence corresponding to a protein which is different from the YRS protein, and which is derived from the same or a different organism. The YRS polypeptide of the fusion protein can correspond to all or a portion of a biologically active YRS amino acid sequence. In certain embodiments, a YRS fusion protein includes at least one (or two) biologically active portion of an YRS protein. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order.

The fusion partner may be designed and included for essentially any desired purpose provided they do not adversely affect the thrombopoietic activity of the polypeptide. For example, in one embodiment, a fusion partner may comprise a sequence that assists in expressing the protein (an expression enhancer) at higher yields than the native recombinant protein. Other fusion partners may be selected so as to increase the solubility of the protein or to enable the protein to be targeted to desired intracellular compartments.

The fusion protein can include a moiety which has a high affinity for a ligand. For example, the fusion protein can be a GST-YRS fusion protein in which the YRS sequences are fused to the C-terminus of the GST sequences. As another example, a YRS polypeptide may be fused to an eight amino acid tag at the C-terminus, such as an L-E-H-H-H-H-H-H (SEQ ID NO:5) tag. In certain embodiments, amino acids 1-364 of a YRS polypeptide are fused to a 365-L-E-H-H-H-H-H-H-372 (SEQ ID NO:5) tag at the C-terminus. Such fusion proteins can facilitate the purification and/or identification of a YRS polypeptide. Alternatively, the fusion protein can be a YRS protein containing a heterologous signal sequence at its N-terminus. In certain host cells, expression and/or secretion of YRS proteins can be increased through use of a heterologous signal sequence.

More generally, fusion to heterologous sequences, such as an Fc fragment, may be utilized to remove unwanted characteristics or to improve the desired characteristics (e.g., pharmacokinetic properties) of a thrombopoietic YRS polypeptide. For example, fusion to a heterologous sequence may increase chemical stability, decrease immunogenicity, improve in vivo targeting, and/or increase half-life in circulation of a thrombopoietic YRS polypeptide.

Fusion to heterologous sequences may also be used to create bi-functional fusion proteins, such as bi-functional proteins that are not only capable of stimulating thrombopoiesis, megakaryocyte proliferation and/or differentiation, and/or neutrophil proliferation through the YRS polypeptide, but are also capable of modifying (i.e., stimulating or inhibiting) other pathways through the heterologous polypeptide. Examples of such pathways include, but are not limited to, various immune system-related pathways, such as innate or adaptive immune activation pathways, or cell-growth regulatory pathways, such as hematopoiesis and angiogenesis. In certain aspects, the heterologous polypeptide may act synergistically with the YRS polypeptide to stimulate thrombopoietic-related and/or hematopoietic-related pathways in a subject. Examples of heterologous polypeptides that may be utilized to create a bi-functional fusion protein include, but are not limited to, thrombopoietin, cytokines (e.g., IL-11), chemokines, and various hematopoietic growth factors, in addition to biologically active fragments and/or variants thereof.

Fusion proteins may generally be prepared using standard techniques. For example, DNA sequences encoding the polypeptide components of a desired fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures, if desired. Such a peptide linker sequence is incorporated into the fusion protein using standard techniques well known in the art. Certain peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39 46 (1985); Murphy et al., *Proc. Natl. Acad. Sci. USA* 83:8258 8262 (1986); U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences may be operably linked to suitable transcriptional or translational regulatory elements. The regulatory elements responsible for expression of DNA are located 5' to the DNA sequence encoding the first polypeptides. Similarly, stop codons required to end translation and transcription termination signals are present 3' to the DNA sequence encoding the second polypeptide.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Certain embodiments also encompass dimers of YRS polypeptides. Dimers may include, for example, homodimers between two identical YRS polypeptides, heterodimers between two different YRS polypeptides (e.g., a full-length YRS polypeptide and a truncated YRS polypeptide), and/or heterodimers between a YRS polypeptide and a heterologous polypeptide. Certain heterodimers, such as those between a YRS polypeptide and a heterologous polypeptide, may be bi-functional, as described herein.

Certain embodiments of the present invention also contemplate the use of modified YRS polypeptides, including modifications that improved desired characteristics of a YRS polypeptide, as described herein. Modifications of YRS polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Exemplary modifications also include pegylation of a YRS-polypeptide (see, e.g., Veronese and Harris, *Advanced Drug Delivery Reviews* 54: 453-456, 2002, herein incorporated by reference).

In certain aspects, chemoselective ligation technology may be utilized to modify truncated YRS polypeptides of the invention, such as by attaching polymers in a site-specific and controlled manner. Such technology typically relies on the incorporation of chemoselective anchors into the protein backbone by either chemical or recombinant means, and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

The truncated and/or variant YRS polypeptides of the invention may be prepared by any suitable procedure known to those of skill in the art, such as by recombinant techniques. For example, YRS polypeptides may be prepared by a procedure including the steps of: (a) preparing a construct comprising a polynucleotide sequence that encodes a truncated YRS polypeptide and that is operably linked to a regulatory element; (b) introducing the construct into a host cell; (c) culturing the host cell to express the truncated YRS polypeptide; and (d) isolating the truncated and/or variant YRS polypeptide from the host cell. In illustrative examples, the nucleotide sequence encodes at least a biologically active portion of a polypeptide sequence set forth in, or derived from, SEQ ID NOS:1, 2, 3, 6, 8, 10, 12, or 14, or a biologically active variant or fragment thereof. Recombinant YRS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6.

In addition to recombinant production methods, polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

Polynucleotide Compositions

The present invention also provides isolated polynucleotides that encode the tyrosyl-tRNA synthetase polypeptides of the invention, including truncations and/or variants thereof, as well as compositions comprising such polynucleotides.

As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a tyrosyl-tRNA synthetase or a portion thereof) or may comprise a variant, or a biological functional equivalent of such a sequence. Polynucleotide variants may contain one or more substitutions, additions, deletions and/or insertions, as further described below, preferably such that the thrombopoietic activity of the encoded polypeptide is not substantially diminished relative to the unmodified polypeptide. The effect on the thrombopoietic activity of the encoded polypeptide may generally be assessed as described herein.

In additional embodiments, the present invention provides isolated polynucleotides comprising various lengths of contiguous stretches of sequence identical to or complementary to a tyrosyl-tRNA synthetase, wherein the isolated polynucleotides encode a truncated tyrosyl tRNA synthetase as described herein.

Exemplary nucleotide sequences that encode the YRS polypeptides of the application encompass full-length YRS genes, such as the polynucleotide sequences of SEQ ID NOS:4, 7, 9, 11, 13, and 15, as well as portions of the full-length or substantially full-length nucleotide sequences of the YRS genes or their transcripts or DNA copies of these transcripts. Portions of a YRS nucleotide sequence may encode polypeptide portions or segments that retain the biological activity of the reference polypeptide. A portion of a YRS nucleotide sequence that encodes a biologically active fragment of a YRS polypeptide may encode at least about 20, 21, 22, 23, 24, 25, 30, 40, 50, 60, 70, 80, 90, 100, 120, 150, 300 or 400 contiguous amino acid residues, or almost up to the total number of amino acids present in a full-length YRS polypeptide. It will be readily understood that "intermediate lengths," in this context and in all other contexts used herein, means any length between the quoted values, such as 101, 102, 103, etc.; 151, 152, 153, etc.; 201, 202, 203, etc.

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed, with the total length preferably being limited by the ease of preparation and use in the intended recombinant DNA protocol.

The invention also contemplates variants of the YRS nucleotide sequences. Nucleic acid variants can be naturally-occurring, such as allelic variants (same locus), homologs (different locus), and orthologs (different organism) or can be non naturally-occurring. Naturally occurring variants such as these can be identified with the use of well-known molecular biology techniques, as, for example, with polymerase chain reaction (PCR) and hybridization techniques as known in the art. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product). For nucleotide sequences, conservative variants include those sequences that, because of the degeneracy of the genetic code, encode the amino acid sequence of a reference YRS polypeptide, such as the sequences set forth in SEQ ID NOS: 1, 2, 3, 6, 8, 10, 12, and 14. Variant nucleotide sequences also include synthetically derived nucleotide sequences, such as those generated, for example, by using site-directed mutagenesis but which still encode a YRS polypeptide. Generally, variants of a particular YRS nucleotide sequence will have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters.

YRS nucleotide sequences can be used to isolate corresponding sequences and alleles from other organisms, particularly other organisms or microorganisms. Methods are readily available in the art for the hybridization of nucleic acid sequences. Coding sequences from other organisms may be isolated according to well known techniques based on their sequence identity with the coding sequences set forth herein. In these techniques all or part of the known coding sequence is used as a probe which selectively hybridizes to other YRS-coding sequences present in a population of cloned genomic DNA fragments or cDNA fragments (i.e., genomic or cDNA libraries) from a chosen organism.

Accordingly, the present invention also contemplates polynucleotides that hybridize to reference YRS nucleotide sequences, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used. Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions). Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M $NaHPO_4$ (pH 7.2), 7% SDS for hybridization at 65° C., and (i) 2×SSC, 0.1% SDS; or (ii) 0.5% BSA, 1 mM EDTA, 40 mM $NaHPO_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C. High stringency conditions also may include 1% BSA, 1 mM EDTA, 0.5 M $NaHPO_4$ (pH 7.2), 7% SDS for hybridization at 65° C., and (i) 0.2×SSC, 0.1% SDS; or (ii) 0.5% BSA, 1 mM EDTA, 40 mM $NaHPO_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C.

In certain embodiments, a YRS polypeptide is encoded by a polynucleotide that hybridizes to a disclosed nucleotide sequence under very high stringency conditions. One embodiment of very high stringency conditions includes hybridizing in 0.5 M sodium phosphate, 7% SDS at 65° C., followed by one or more washes in 0.2×SSC, 1% SDS at 65° C.

Other stringency conditions are well known in the art and a skilled addressee will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m$=81.5+16.6 ($\log_{10}$ M)+0.41 (% G+C)−0.63 (% formamide)−(600/length) wherein: M is the concentration of $Na^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The Tm of a duplex DNA decreases by approximately 1° C. with every increase of 1% in the number of randomly mismatched base pairs. Washing is generally carried out at $T_m$−15° C. for high stringency, or $T_m$−30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a truncated and/or variant tyrosyl-tRNA synthetase polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer or immediate/early cytomegalovirus (CMV) enhancer/promoter region, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins.

Antibody Compositions, Fragments Thereof and Other Binding Agents

According to another aspect, the present invention further provides binding agents, such as antibodies and antigen-binding fragments thereof, that exhibit immunological binding to a polypeptide disclosed herein, or to a portion, variant or derivative thereof, and methods of using same. Preferably, such binding agents are effective for modulating one or more of the non-canonical activities mediated by a YRS polypeptide of the invention, or for detecting the presence or absence of selected YRS polypeptides (e.g., truncations, alternate splice variants, mutants) in a sample, such as a biological sample obtained from a subject.

For example, certain embodiments contemplate a method of identifying or characterizing a YRS polypeptide in a subject, comprising obtaining a biological sample from the subject, contacting the biological sample with an antibody, or antigen-binding fragment thereof, wherein the antibody or antigen-fragment specifically binds to a YRS polypeptide of the invention, and detecting the presence or absence of the bound antibody, or antigen-binding fragment thereof, thereby identifying or characterizing the YRS polypeptide in the subject. In certain aspects, the antibody, or antigen-binding fragment thereof, specifically binds to a certain variant or truncated YRS polypeptide, such as a selected YRS mutant or alternate splice variant, but does not specifically bind to other YRS polypeptides, such as a full-length, wild type YRS polypeptide.

An antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs." Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

A binding agent may be, for example, a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, Antibodies: A Laboratory Manual, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "$F(ab')_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci.* USA 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures-regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349:293-299; Lobuglio et al. (1989) *Proc. Nat. Acad. Sci. USA* 86:4220-4224; Shaw et al. (1987) *J Immunol.* 138:4534-4538; and Brown et al. (1987) *Cancer Res.* 47:3577-3583), rodent CDRs grafted into a human supporting FR prior to fusion with an appropriate human antibody constant domain (Riechmann et al. (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) *Ann. Rev. Biochem.* 59:439-473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

In another embodiment of the invention, monoclonal antibodies of the present invention may be coupled to one or more agents of interest. For example, a therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used.

Thrombocytopenia and Methods of Use

As noted above, the present invention generally relates to methods of treating, and/or reducing the risks of developing, thrombocytopenia or other conditions associated with decreased platelet count. Thrombocytopenia is generally characterized by reduced platelet counts, as compared to a normal range of platelet counts for a typical subject. For example, thrombocytopenia refers generally to a decrease in the platelet count to about 100,000/$mm^3$ or lower compared to a normal platelet count. A normal platelet count generally ranges from about 150,000 $mm^3$ to about 450,000 $mm^3$ in a subject.

Thrombocytopenia often causes no signs or symptoms, but may be identified by routine blood tests. If present, possible signs and symptoms of thrombocytopenia include easy bruising and/or excessive bleeding. For example, bleeding in the skin may be the first sign of a low platelet count. Many tiny red dots (petechiae) often appear in the skin on the lower legs, and minor injuries may cause small scattered bruises. In addition, the gums may bleed, and blood may appear in the stool or urine. Menstrual periods may be unusually heavy. Bleeding may be hard to stop.

Bleeding typically worsens as the number of platelets decreases. People who have very few platelets may lose large amounts of blood into the digestive tract or may develop life-threatening bleeding in the brain even though they have not been injured. The rate at which symptoms develop can vary depending on the cause of thrombocytopenia.

Thrombocytopenia may be congenital, acquired, and/or iatrogenic, and may stem from a variety of underlying physiological causes or conditions. For example, thrombocytopenia may result generally from decreased production of platelets, increased destruction of platelets, consumption of platelets, entrapment/sequestration of platelets due to hypersplenism (i.e., enlarged spleen) or hypothermia, and/or from the side-effects of certain medications (i.e., medication induced thrombocytopenia). In addition, idiopathic forms of thrombocytopenia occur, especially in children, transient forms may follow viral infections (e.g., Epstein-Barr or infectious mononucleosis), and pregnant women may develop mild thrombocytopenia, often when close to delivery.

Examples of congenital conditions associated with the decreased production (i.e., diminished or defective production) of platelets include Wiskott-Aldrich syndrome, maternal ingestion of thiazides, congenital amegakaryocytic thrombocytopenia, thrombocytopenia absent radius syndrome, Fanconi anemia, Bemard-Soulier syndrome, May-Hegglin anomaly, Grey platelet syndrome, Alport syndrome, and neonatal rubella. Examples of acquired conditions associated with the decreased production of platelets include aplastic anemia, myeolodysplastic syndrome, marrow infiltration (e.g., acute and chronic leukemias, tumors, cancer of the bone marrow), lymphomas, nutritional deficiencies (e.g., $B_{12}$, folic acid), the use of myelosuppressive agents, the use of drugs that directly influence platelet production (e.g., thiazides, alcohol, hormones), radiation exposure (e.g., radiation therapy), exposure to toxic chemicals (e.g., pesticides, arsenic, benzene), decreased production of thrombopoietin by the liver in liver failure, bacterial sepsis, and certain viral infections (e.g., chickenpox, mumps, parvovirus, measles, dengue, HIV, HCV).

Examples of congenital conditions associated with increased peripheral platelet destruction include nonimmune conditions, such as prematurity, erythroblastosis fetalis, infection; and immune conditions, such as drug sensitivity, idiopathic thrombocytopenic purpura (ITP), and maternal ITP. Examples of acquired conditions associated with increased peripheral platelet destruction include nonimmune conditions, such as hemolytic-uremic syndrome, disseminated intravascular coagulation, thrombotic thrombocytopenic purpura (TTP); immune conditions, such as drug-induced thrompocytopenia (e.g., especially with quinine and quinidine), post-transfusion purpura, systemic lupus erythematosus, rheumatoid arthritis, neonatal alloimmune thrombocytopenia, paroxysmal nocturnal hemoglobinuria, acute and chronic ITP, sepsis, and alcohol; in addition to the use of invasive lines and devices (e.g., arterial or central venous catheters), intra-aortic balloon pumps, prosthetic heart valves, as well as the use of heparin-related therapies.

Medication-induced thrombocytopenia may result in particular from certain drugs, such as chemotherapeutic agents, nonsteroidal anti-inflammatory agents, sulfonamides, vancomycin, clopidogrel, glycoprotein IIb/IIIa inhibitors, interferons, valproic acid, abciximab, linezolid, famotidine, mebeverine, histamine blockers, alkylating agents, heparin, alcohol, antibiotic chemotherapeutic agents, carbapenems, ureido-penicillins, cefazolin, among others known in the art. Particular examples of chemotherapeutic agents include, but are not limited to, cisplatin (CDDP), carboplatine, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, famesyl-protein transferase inhibitors, transplatinum, 5-fluorouracil, vincristine, vinblastine and methotrexate, Temazolomide (an aqueous form of DTIC), or any analog or derivative variant of the foregoing.

The present invention relates generally to methods of treating, or reducing the risks of developing, thrombocytopenia (i.e., decreased platelet count) in a subject, such as in a subject having one or more of the exemplary diseases or conditions provided herein, among others known in the art, by administering to the subject a composition comprising a thrombopoietically-effective concentration of a truncated and/or variant tyrosyl-tRNA synthetase polypeptide, or a modified polypeptide thereof. Embodiments of the present invention encompass methods of treatment intended not only to increase or improving the platelet count in a subject having a reduced, decreased, abnormal, or low platelet count, but to maintain a normal platelet count in a subject at risk for developing a low platelet count. Certain embodiments also contemplate the use of YRS polypeptides to increase the platelet count in a platelet donor, including an otherwise healthy donor (i.e., a donor with a normal platelet count), such as administering a YRS polypeptide to the donor prior to, during, and/or after the platelet donation or apheresis process.

Accordingly, certain embodiments include methods for increasing the platelet count in a subject, comprising administering to the subject a composition comprising a thrombopoietically-effective concentration of a truncated and/or tyrosyl-tRNA synthetase polypeptide, or a modified polypeptide thereof, thereby increasing the platelet count in the subject. Other embodiments include methods of maintaining a normal platelet count in subject, comprising administering to the subject a composition comprising a thrombopoietically-effective concentration of a truncated and/or variant tyrosyl-tRNA synthetase polypeptide, such as wherein the subject is at risk for developing a low platelet count. Certain embodiments may include methods of stimulating thrombopoiesis in a subject, such as by administering to the subject a composition comprising a thrombopoietically-effective concentration of a truncated and/or variant tyrosyl-tRNA synthetase polypeptide. In certain aspects, the subject has a reduced, lowered, or abnormal platelet count, such as a platelet count of about $100,000/mm^3$ or less. In certain aspects, the YRS polypeptides provided herein may be utilized to stimulate the proliferation and/or differentiation of megakaryocytes and/or neutrophils in a subject.

A subject having a reduced platelet count may also be at risk for developing other problems associated with thrombocytopenia, such as bleeding or bruising, hemorrhage, gastrointestinal bleeding, eptistaxis (i.e., nose bleeds), or intracranial hemorrhage (i.e., bleeding in the brain). As one particular example, septic patients with thrombocytopenia have increased bleeding. Accordingly, certain aspects of the invention may utilize the thrombopoietic compositions provided herein to reduce the risk of developing these types of thrombocytopenia associated problems, among others. In other aspects, the subject may be at risk for developing a reduced, lowered, or otherwise abnormal platelet count, such as from an acquired condition associated with lowered platelet levels (e.g., certain medical therapies, leukemias, among others).

In certain aspects, the methods of treatments described herein may be employed independently of other therapeutic modalities, and may be the only or primary therapeutic modality relied upon to manage a thrombocytopenic condition and/or otherwise reduce the risk not only of developing thrombocytopenia, but of developing other medical problems associated therewith, such as bleeding. For example, a subject having thrombocytopenia for which there is no known, underlying cause (e.g., idiopathic thrombocytopenic purpura), may benefit from the methods of treatment provided herein to increase and/or manage platelet levels.

In certain aspects, the methods and compositions of the present invention may be employed as part of a combination therapy, such as by administration with other agents that may stimulate thrombopoetic and/or hematopoietic pathways in a subject. Examples of other agents that may be used as part of a combination therapy include thrombopoetin, cytokines (e.g., IL-11), chemokines, and/or growth factors involved in thrombopoiesis or hematopoiesis, including biologically active fragments or variants thereof.

In certain aspects, the methods of the present invention may be employed in conjunction with other therapeutic modalities, such as those involved in treating the underlying condition that causes the condition associated with thrombocytopenia. For example, a subject having congenital amegakaryocytic thrombocytopenia (CAMT) may ultimately undergo a bone marrow transplantation procedure, but may also benefit from a separate treatment, as provided herein, to either enhance platelet levels and/or to maintain platelet levels within a normal range. The thrombopoietic polypeptides of the present invention may be employed in this and similar regards.

In certain aspects, the methods provided herein may be employed in combination with a subject undergoing other medical treatments, such as treatments that either cause thrombocytopenia or increase the risk of developing thrombocytopenia. For example, the methods provided herein may be employed with a subject undergoing, a subject about to undergo, and/or a subject who as undergone, radiation therapy, chemotherapy, or other type of treatment, including various types of pharmaceutical treatments, as described herein and known in the art, since such treatments are known to reduce the platelet count in a subject. Accordingly, the methods provided herein may be utilized before, during, and/or after other medical treatments to reduce the risk of developing thrombocytopenia resulting from such treatments, and/or to manage or improve thrombocytopenia resulting from such treatments.

In certain embodiments, the methods provided herein may be utilized to prophylactically treat or manage thrompocytopenic symptoms associated with such particular conditions as described herein and known in the art.

Stimulation of Megakaryocyte Progenitor Cells and Methods of Use

The YRS polypeptides of the present invention may also be used to stimulate the growth of megakaryocyte progenitor cells, including early progenitor cells, i.e., the most primitive lineage-restricted progenitors of the megakaryocyte lineage. Included are methods of stimulating proliferation of early megakaryocyte progenitor cells, comprising incubating a culture of hematopoietic stem cells with a tyrosyl-tRNA synthetase polypeptide for a time sufficient to allow proliferation of the early megakaryocyte progenitor cells, thereby stimulating proliferation of early megakaryocyte progenitor cells. In these and related embodiments, the YRS polypeptides of the invention may be incubated with purified HSCs, partially purified HSCs, whole bone marrow cultures (e.g., for bone marrow transplants), cord blood, or other types of cultures used in hematopoietic graft therapies. Such methods may result in a culture that is enriched for early megakaryocyte progenitor cells. YRS polypeptides of the invention may also be administered directly to a subject (in vivo) to stimulate proliferation of early megakaryocyte progenitors in that subject.

"Hematopoietic stem cells (HSCs)" relate generally to either pluripotent or multipotent "stem cells" that give rise to the blood cell types, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art. "Stem cells" are typically defined by their ability to form multiple cell types (i.e., multipotency) and their ability to self-renew. In certain embodiments, however, oligopotent and unipotent progenitors may be included. "Hematopoiesis" refers generally to the process of cellular differentiation or formation of particular, specialized blood cells from an HSC.

HSCs may be obtained according to known techniques in the art. For instance, HSCs may be found in the bone marrow of adults, which includes femurs, hip, ribs, sternum, and other bones. HSCs may be obtained directly by removal from the hip using a needle and syringe, or from the blood, often following pre-treatment with cytokines, such as G-CSF (granulocyte colony-stimulating factors), that induce cells to be released from the bone marrow compartment. Other sources for clinical and scientific use include umbilical cord blood, placenta, and mobilized peripheral blood. For experimental purposes, fetal liver, fetal spleen, and AGM (Aorta-gonad-mesonephros) of animals are also useful sources of HSCs.

HSCs may be identified according to certain phenotypic or genotypic markers. For example, HSCs may be identified by their small size, lack of lineage (lin) markers, low staining (side population) with vital dyes such as rhodamine 123 (rhodamine$^{DULL}$, also called rho$^{lo}$) or Hoechst 33342, and presence of various antigenic markers on their surface, many of which belong to the cluster of differentiation series (e.g., CD34, CD38, CD90, CD133, CD105, CD45, and c-kit, the receptor for stem cell factor). HSCs are mainly negative for the markers that are typically used to detect lineage commitment, and, thus, are often referred to as lin(−) cells. Most human HSCs may be characterized as CD34+, CD59+, Thy1/CD90$^+$, CD38$^{lo/-}$, C-kit/CD117$^+$, and lin(−). However, not all stem cells are covered by these combinations, as certain HSCs are CD34$^-$-CD38$^-$. Also some studies suggest that earliest stem cells may lack c-kit on the cell surface. For human HSCs, CD133 may represent an early marker, as both CD34$^+$ and CD34$^-$ HSCs have been shown to be CD133$^+$.

For purification of lin(−) HSCs by flow cytometry, or FACS, an array of mature blood-lineage marker antibodies may be used to deplete the lin(+) cells or late multipotent progenitors (MPP), including, for example, antibodies to CD13 and CD33 for human myeloid cells, CD71 for human erythroid cells, CD19 for human B cells, CD61 for human megakaryocytic cells, Mac-1 (CD11b/CD18) for monocytes, Gr-1 for Granulocytes, Il7Ra, CD3, CD4, CD5, and CD8 for T cells, among others known in the art. Other purification methods are known in the art, such as those methods that use the particular signature of the 'signaling lymphocyte activation molecules' (SLAM) family of cell surface molecules.

HSCs, whether obtained from, or present in, cord blood, bone marrow, peripheral blood, or other source, may be grown or expanded in any suitable, commercially available or custom defined medium, with or without serum, as desired (see, e.g., Hartshorn et al., *Cell Technology for Cell Products, pages* 221-224, R. Smith, Editor; Springer Netherlands, 2007, herein incorporated by reference in its entirety). For instance, in certain embodiments, serum free medium may utilize albumin and/or transferrin, which have been shown to be useful for the growth and expansion of CD34+ cells in serum free medium. Also, cytokines may be included, such as Flt-3 ligand, stem cell factor (SCF), and thrombopoietin (TPO), among others. HSCs may also be grown in vessels such as bioreactors (see, e.g., Liu et al., *Journal of Biotechnology* 124:592-601, 2006, herein incorporated by reference in its entirety). A suitable medium for ex vivo expansion of HSCs may also comprise HSC supporting cells, such as stromal cells (e.g., lymphoreticular stromal cells), which can be derived, for instance, from the disaggregation of lymphoid tissue, and which have been show to support the in vitro, ex vivo, and in vivo maintenance, growth, and differentiation of HSCs, as well as their progeny.

HSC growth or expansion can be measured in vitro or in vivo according to routine techniques known in the art. For example, WO 2008/073748, herein incorporated by references for these methods, describes methods for measuring in vivo and in vitro expansion of HSCs, and for distinguishing between the growth/expansion of HSCs and the growth/expansion of other cells in a potentially heterogeneous population (e.g., bone marrow), such as intermediate progenitor cells. The administering or incubation step that results in the growth or expansion can occur in vivo, ex vivo, or in vitro, though in certain embodiments, the administration or incubation occurs during ex vivo treatment of HSCs.

Growth or proliferation of megakaryocyte progenitor cells (e.g., early, intermediate, late, etc.) can also be measured according to routine techniques known in the art and described herein (see, e.g., Example 10). For instance, among other characteristics, early megakaryocyte progenitors may be identified by immuno-staining as Lin$^-$c-Kit$^+$ CD41$^+$, and later stage megakaryocyte progenitors may be identified as Lin$^-$c-Kit$^-$ CD41$^+$ (see, e.g., Perez et al., *PLoS ONE.* 3:e3565, 2008; and Lefebvre et al., *Journal of Hematotherapy & Stem Cell Research.* 9:913-921, 2000, each of which is incorporated by reference in its entirety).

"Cord blood" or "umbilical cord blood" relates generally to the relatively small amount of blood (up to about 180 mL) from a newborn baby that returns to the neonatal circulation if the umbilical cord is not prematurely clamped. Cord blood is rich in HSCs, and may be harvested and stored for later use according to techniques known in the art (see, e.g., U.S. Pat. Nos. 7,147,626 and 7,131,958, herein incorporated by reference for such methodologies). Also, if the umbilical cord is ultimately not clamped, a physiological clamping occurs upon interaction with cold air, wherein the internal gelatinous substance, called Wharton's jelly, swells around the umbilical artery and veins. Nonetheless, Wharton's jelly can still serve as a source of HSCs.

As noted above, "ex vivo" refers to generally to activities that take place outside an organism, such as experimentation or measurements done in or on living tissue in an artificial environment outside the organism, preferably with minimum alteration of the natural conditions. Most commonly, "ex vivo" procedures involve living cells or tissues taken from an organism and cultured in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The terms "ex vivo administration," "ex vivo treatment," or "ex vivo therapeutic use," relate generally to medical procedures in which one or more organs, cells, or tissues are obtained from a living or recently deceased subject, optionally purified/enriched, exposed to a treatment or procedure to expand the stem cells (e.g., an ex vivo administration step that involves incubating the cells with a composition of the present invention to enhance expansion of desirable cells, such as HSCs or megakaryocyte progenitors), and then administered to the same or different living subject after that optional treatment or procedure. As one example, thrombocytopenia may be alleviated by infusion of megakaryocyte progenitor cells (see, e.g., De Bruyn et al., *Stem Cells Dev.* 14:415-24, 2005, herein incorporated by reference).

Such ex vivo therapeutic applications may also include an optional in vivo treatment or procedural step, such as by administering a YRS polypeptide of the invention one or more times to the living subject prior to, during, or after administration of the organ, cells, or tissue. Both local and systemic administration are contemplated for these embodiments, according to well-known techniques in the art. The amount of YRS polypeptide administered to a subject will depend on the characteristics of that subject, such as general health, age, sex, body weight, and tolerance to drugs, as well as the degree, severity, and type of reaction to the polypeptide and/or cell transplant.

Stimulation of CXCR-2 Expressing Cells

Certain embodiments relate to the discovery that YRS polypeptides are capable of stimulating the migration of CXCR-2 expressing cells. CXCR-2 is a member of the CXC chemokine receptor family, expressed on a wide variety of cell types, including neutrophils and other immune cells. CXC chemokine receptors are integral membrane proteins that specifically bind and respond to cytokines of the CXC chemokine family. These CXC-based receptors represent one subfamily of chemokine receptors, a large family of G protein-linked receptors, also referred to as seven transmembrane receptors. There are currently seven known CXC chemokine receptors in mammals, named CXCR1 through CXCR7. CXCR-2 (and highly related CXCR-1) is a well-known receptor that recognizes C-X-C chemokines which possess an E-L-R amino acid motif immediately adjacent to their C-X-C motif. CXCL8 (i.e., interleukin-8) and CXCL6 can both bind CXCR1 in humans, while all other ELR-motif-positive chemokines, such as CXCL1 to CXCL7, bind only CXCR2 (see, e.g., Tsai et al., *Cell* 110:373-383, 2002; and Pelus et al., *Exp Hematol.* 34:1010-20, 2006, each of which is incorporated by reference in its entirety). As noted above, CXCR-2 is expressed on the surface of neutrophils, and can play a role in neutrophil migration (see, e.g., Rios-Santos et al., *American Journal of Respiratory and Critical Care Medicine* 175:490-497, 2007, incorporated by reference in its entirety).

Accordingly, given the role of CXCR-2 in cell signaling and cell migration (e.g., neutrophil signaling/migration), among other biologically relevant pathways, certain embodiments include methods of stimulating migration of a CXCR-2 expressing cell, comprising contacting the cell with a tyrosyl-tRNA synthetase polypeptide, thereby stimulating migration of the CXCR-2 expressing cell.

Pulmonary Diseases and Methods of Use

Embodiments of the present invention also relate to the unexpected discovery that YRS polypeptides may provide benefits in the treatment of pulmonary diseases, such as chronic obstructive pulmonary disease (COPD). In this regard, neutrophil migration from the circulatory system to the lungs is implicated in chronic pulmonary obstructive disease (COPD) (see, e.g., R. A. Stockley, *Chest* 121:151S-155S, 2002, incorporated by reference in its entirety). As noted above, CXCR-2 is expressed on the surface of neutrophils, and can play a role in neutrophil migration (see, e.g., Rios-Santos et al., *American Journal of Respiratory and Critical Care Medicine* 175:490-497, 2007, incorporated by reference in its entirety). Since CXCR-2 signaling in neutrophils is implicated in their migration to certain tissues, such as the lungs, especially in response to foreign matter, such as irritants, bacteria, lipopolysaccharide (LPS) etc., it may thus be implicated in various pathological conditions, such as COPD.

Given the observations that YRS polypeptides of the invention affect CXCR-2 signaling and polymorphonuclear (PMN) cell migration (see, e.g., Examples 7 and 8), it is believed that these polypeptides may be useful in the treatment or management of pulmonary diseases, such as COPD. For instance, without wishing to be bound by any one theory, YRS polypeptides may be used to desensitize circulatory neutrophils to various irritants or allergens, thereby reducing the migration of these immune cells into the lungs (see, e.g., Example 9). Hence, certain embodiments relate to methods of treating or managing (e.g., reducing the complications of) pulmonary inflammation and/or pulmonary diseases, such as COPD, comprising administering to a subject with pulmonary inflammation or COPD an effective concentration of a tyrosyl-tRNA synthetase polypeptide, thereby reducing COPD, and/or its symptoms, in the subject. Often, in desensitizing immune cells, multiple administrations are required (1, 2, 3, 4, 5, 6, 7, 8, 9, 10, etc), typically at a defined frequency (number of administrations per day, per week, per month, etc).

COPD refers generally to a group of lung diseases that block airflow and make it increasingly difficult for affected individuals to breathe normally. Emphysema and chronic bronchitis are the two main conditions within the group of COPD diseases, but COPD can also refer to damage caused by chronic asthmatic bronchitis, among other conditions known in the art. In all cases, damage to the airways eventually interferes with the exchange of oxygen and carbon dioxide in the lungs. Treatment focuses mainly on controlling symptoms and minimizing further damage.

Emphysema represents one aspect of COPD. Emphysema leads to inflammation within the fragile walls of the alveoli, which may destroy some of the walls and elastic fibers, allowing small airways to collapse upon exhaling, and impairing airflow out of the lungs. Signs and symptoms of emphysema include, for instance, shortness of breath, especially during physical activities, wheezing, and chest tightness.

Chronic bronchitis represents another aspect of COPD. Chronic bronchitis is characterized by an ongoing cough, and leads to inflammation and narrowing of the bronchial tubes. This condition also causes increased mucus production, which can further block the narrowed tubes. Chronic bronchitis occurs mainly in smokers, and is typically defined as a cough that lasts for at least three months a year for two consecutive years. Signs and symptoms of chronic bronchitis include, for example, having to clear the throat first thing in the morning, especially for smokers, a chronic cough that produces yellowish sputum, shortness of breath in the later stages, and frequent respiratory infections.

As noted above, COPD refers primarily to obstruction in the lungs resulting from the two above-noted chronic lung conditions. However, many individuals with COPD have both of these conditions.

Chronic asthmatic bronchitis represents another aspect of COPD. Chronic asthmatic bronchitis is usually characterized as chronic bronchitis combined with asthma (bronchospasm). Asthma may occur when inflamed and infected secretions irritate the smooth muscles in the airways. Symptoms are similar to those of chronic bronchitis, but also include intermittent, or even daily, episodes of wheezing.

Mainly, COPD is ultimately caused by cigarette smoke and other irritants. In the vast majority of cases, the lung damage that leads to COPD is caused by long-term cigarette smoking. However, other irritants may cause COPD, including cigar smoke, secondhand smoke, pipe smoke, air pollution and certain occupational fumes. Gastroesophageal reflux disease (GERD), which occurs when stomach acids wash back up into your esophagus, can not only aggravate COPD, but may even cause it in some individuals. In rare cases, COPD results from a genetic disorder that causes low levels of a protein called alpha-1-antitrypsin. Hence, risk factors for COPD include exposure to tobacco smoke, occupational exposure to dusts and chemicals (long-term exposure to chemical fumes, vapors and dusts irritates and inflames the lungs), gastroesophageal reflux disease (a severe form of acid reflux—the backflow of acid and other stomach contents into the esophagus), age (COPD develops slowly over years, so most people are at least 40 years old when symptoms begin), and genetics (a rare genetic disorder known as alpha-1-antitrypsin deficiency is the source of a few cases of COPD).

Complications of COPD may include respiratory infections, high blood pressure, heart problems (e.g., heart attacks), lung cancer (smokers with chronic bronchitis are at a higher risk of developing lung cancer than are smokers who don't have chronic bronchitis), and depression, among others known in the art.

Subjects with COPD may be identified according to routine diagnostic techniques known in the art. For instance, pulmonary function tests, such as spirometry, measure how much air the lungs can hold and how fast an individual can blow the air out of their lungs. Spirometry can detect COPD before the appearance of symptoms, and can also be used to track disease progression and monitor treatment. In addition, chest X-rays show emphysema, one of the main causes of COPD, and may also rule out other lung problems or heart failure. In addition, arterial blood gas analysis measures how effectively the lungs bring oxygen into the blood and remove carbon dioxide, providing an indication of COPD. Sputum examination, i.e., the analysis of the cells in the sputum, can identify the cause of certain lung problems and help rule out certain lung cancers. Also, computerized tomography (CT) scan produces highly-detailed images of the internal organs, which can help detect emphysema, and, thus, COPD.

As elsewhere herein, the amount of YRS polypeptide administered to a subject with COPD (or at risk for COPD) will depend on the characteristics of that subject, such as general health, age, sex, body weight, and tolerance to drugs, as well as the degree, severity, and type of reaction to the polypeptide.

Formulations and Pharmaceutical Compositions

The compositions of the invention comprise tyrosyl-tRNA synthetase polypeptides, including truncations and/or variants thereof, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the thrombopoietic or other effects desired to be achieved.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Stimulation of Thrombopoiesis In Vivo

The effects of a tyrosyl-tRNA synthetase polypeptide on thrombopoiesis were measured in vivo. The tyrosyl-tRNA synthetase polypeptide utilized in the experiments described below is a C-terminal truncation that comprises amino acids 1-364 of the full-length human tyrosyl-tRNA. This C-terminally truncated polypeptide was fused to an eight amino acid C-terminal tag (365-L-E-H-H-H-H-H-H-372) (SEQ ID NO:5). The amino acid sequence of the full-length human tyrosyl-tRNA synthetase is set forth in SEQ ID NO:1.

To measure the effects of tyrosyl-tRNA synthetase polypeptides on thrombopoiesis, in a first set of experiments, mice were injected subcutaneously twice daily for seven days with 3 μg/kg of the C-terminally truncated tyrosyl-tRNA synthetase polypeptide. In a second set of experiments, mice were injected twice daily for seven days with 1, 3, and 10 μg/kg of the C-terminally truncated tyrosyl-tRNA synthetase polypeptide. In a third set of experiments, mice were injected subcutaneously twice daily for six days with (i) 3 and 300 μg/kg of the C-terminally truncated tyrosyl-tRNA synthetase polypeptide, and one single daily injection of (ii) 90 μg/kg thrombopoietin (TPO), and (iii) 250 μg/kg G-CSF.

For the first and second set of experiments described above, the platelet count for each animal was determined upon completion of the administration protocol. For the third set of experiments, bone marrow and spleen histology were examined at the end of the administration protocol.

Figure 5B:
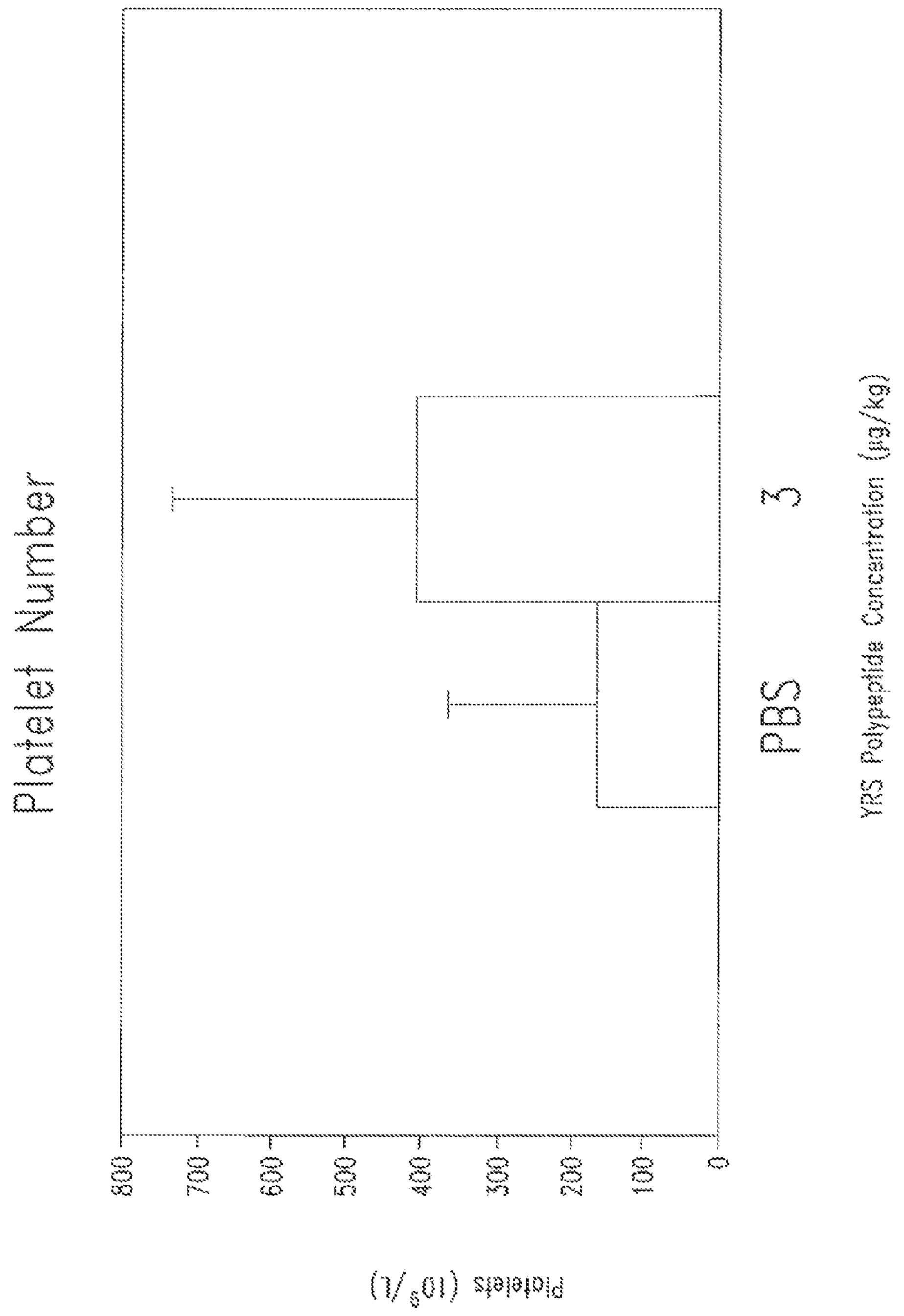
Figure 6:
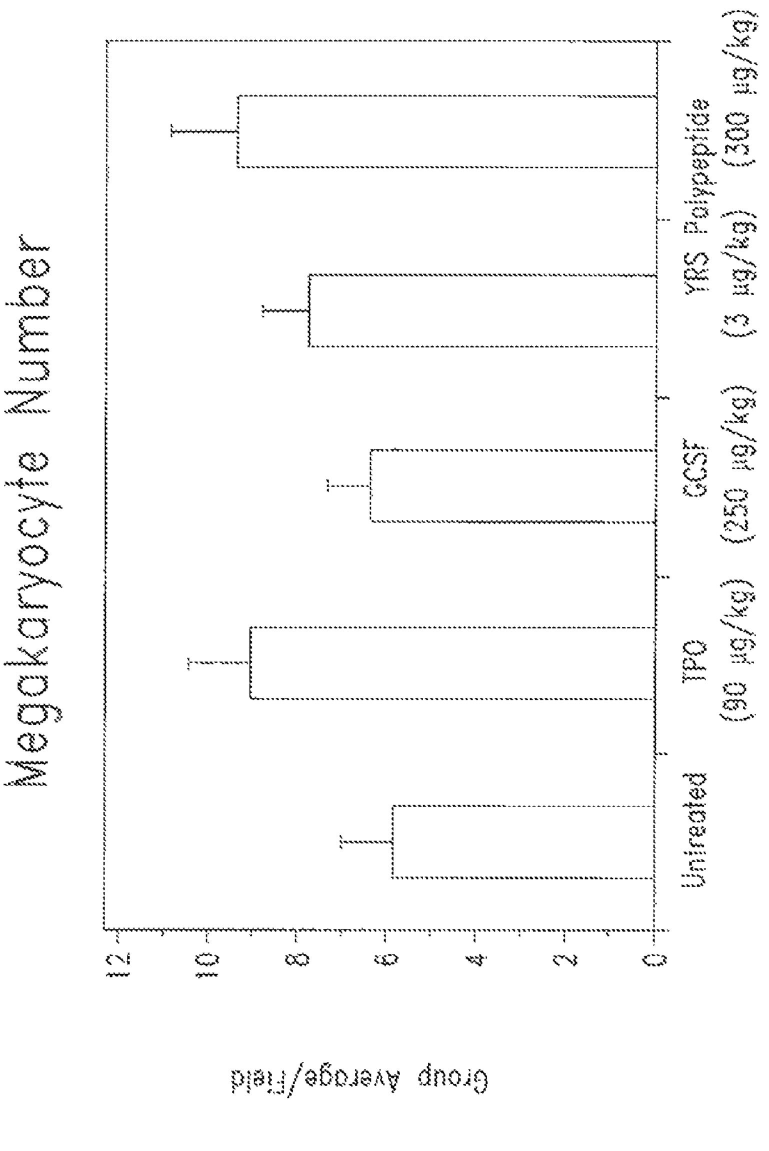
FIG. 6 shows the in vivo effects on megakaryocyte number following administration of a C-terminally truncated human-tyrosyl-tRNA synthetase polypeptide (SEQ ID NO:3) having an eight amino acid C-terminal tag, L-E-H-H-H-H-H-H (SEQ ID NO:5). Animals were injected subcutaneously twice daily with 3 and 300 μg/kg a tyrosyl-tRNA synthetase polypeptide of SEQ ID NO:3 having an eight amino acid C-terminal tag (SEQ ID NO:5) for 6 days and bone marrow and spleen histology were examined at the end of the study.

Administration of a truncated tyrosyl-tRNA synthetase for about one week showed a reproducible, in vivo increase in thrombopoietic activity, as measured by either increased platelet count or increased megakaryocyte numbers. FIG. 5(*a*) shows the platelet count for the experiment in which mice were injected with 1, 3, and 10 μg/kg of the truncated tyrosyl-tRNA synthetase polypeptide, as compared to a phosphate-buffer saline (PBS) control. FIG. 5(*b*) shows the platelet count for the experiment in which mice were injected with 3 μg/kg of the truncated tyrosyl-tRNA synthetase polypeptide, as compared to a PBS control. In both experiments, mice showed an increase in platelet counts over control in response to treatment with a tyrosyl-tRNA polypeptide of the invention. FIG. 6 shows an increase in megakaryocyte numbers in response to administration of the truncated tyrosyl-tRNA synthetase polypeptide, as compared to untreated animals, which is comparable to the increased numbers observed after administration with TPO. These results show that tyrosyl-tRNA synthetase polypeptide fragments, and in particular C-terminally truncated fragments, are capable of stimulating thrombopoiesis in vivo.

Example 2

In Vitro Measurements of Thrombopoiesis

Effects on thrombopoiesis may also be measured in vitro. Stem cells are treated in vitro with a tyrosyl-tRNA synthetase polypeptide of the invention to determine its effect on hematopoietic progenitors of the erythroid, myeloid and megakaryocte lineages using colony-forming cell (CFC) assays (e.g., inhibition, stimulation, toxicity, synergism with other cytokines, hematopoietic defects). In addition, CD34+ megakaryocyte progenitor cells are treated in vitro with a tyrosyl-tRNA synthetase polypeptide of the invention to monitor megakaryocyte expansion and differentiation (e.g., increase in number of progenitor cells, stimulation of differentiation, increase in polyploidy). Similar experiments are performed using bone marrow and spleen cells derived from mice treated with a tyrosyl-tRNA synthetase polypeptide.

Example 3

Combination Therapy Stimulates Thrombopoiesis

To assess whether a tyrosyl-tRNA synthetase polypeptide of the present invention has a synergestic and/or additive effect on the proliferation and differentiation of megakaryocytes in vitro, CD34+ cord blood cells are grown in liquid culture medium in the presence of optimal or sub-optimal formulations of cytokines (StemCell Technologies, Vancouver), such as IL-11, and treated with increasing concentrations of a tyrosyl-tRNA synthetase polypeptide. Additivity or synergism can be determined by monitoring the growth and differentiation of the progenitor cells in the two formulation conditions.

Similarly, in a protocol comparable to that described in Example 1, mice are injected with a limiting amount of thrombopoietin and with increasing amounts of a tyrosyl-tRNA synthetase polypeptide and the effects of the combination therapy on thrombopoiesis in vivo can be determined by platelet and megakaryocyte counts. In addition, combination therapy with limited amounts of other cytokines, chemokines and/or growth factors involved in hematopoiesis can be evaluated using the same type of regimen.

Example 4

Thrombopoietic Activity of Tyrosyl-tRNA Synthetase Polypeptides in Rats

The effects of two tyrosyl-tRNA synthetase polypeptides on thrombopoiesis were measured in rats. The tyrosyl-tRNA synthetase polypeptides utilized in the experiments described below are: i) a C-terminal truncation that comprises amino acids 1-364 of the full-length human tyrosyl-tRNA (SEQ ID NO:3) fused to an eight amino acid C-terminal histidine tag (SEQ ID NO:5) and; ii) a mutant of the full length human tyrosyl-tRNA synthetase with a single, tyrosine to alanine, amino acid substitution at position 341, referred to as “Y341A” (SEQ ID NO: 2).

To measure the effects of tyrosyl-tRNA synthetase polypeptides on thrombopoiesis, platelet count for each rat was determined one day before the first scheduled injection and animals were grouped in seven cohorts according to their initial platelet counts. Three groups of rats were injected intravenously once daily for seven days with 0.1, 10, and 1000 μg/kg of the C-terminally truncated tyrosyl-tRNA synthetase polypeptide, respectively. Three additional groups were administered with the same dosages of Y341A. One control group received a daily injection of buffer only (0.5×PBS, 2 mM DTT) and an additional control group was injected daily with 90 μg/kg of thrombopoietin (R&D Systems, Minneapolis, Minn.).

Figure 20:
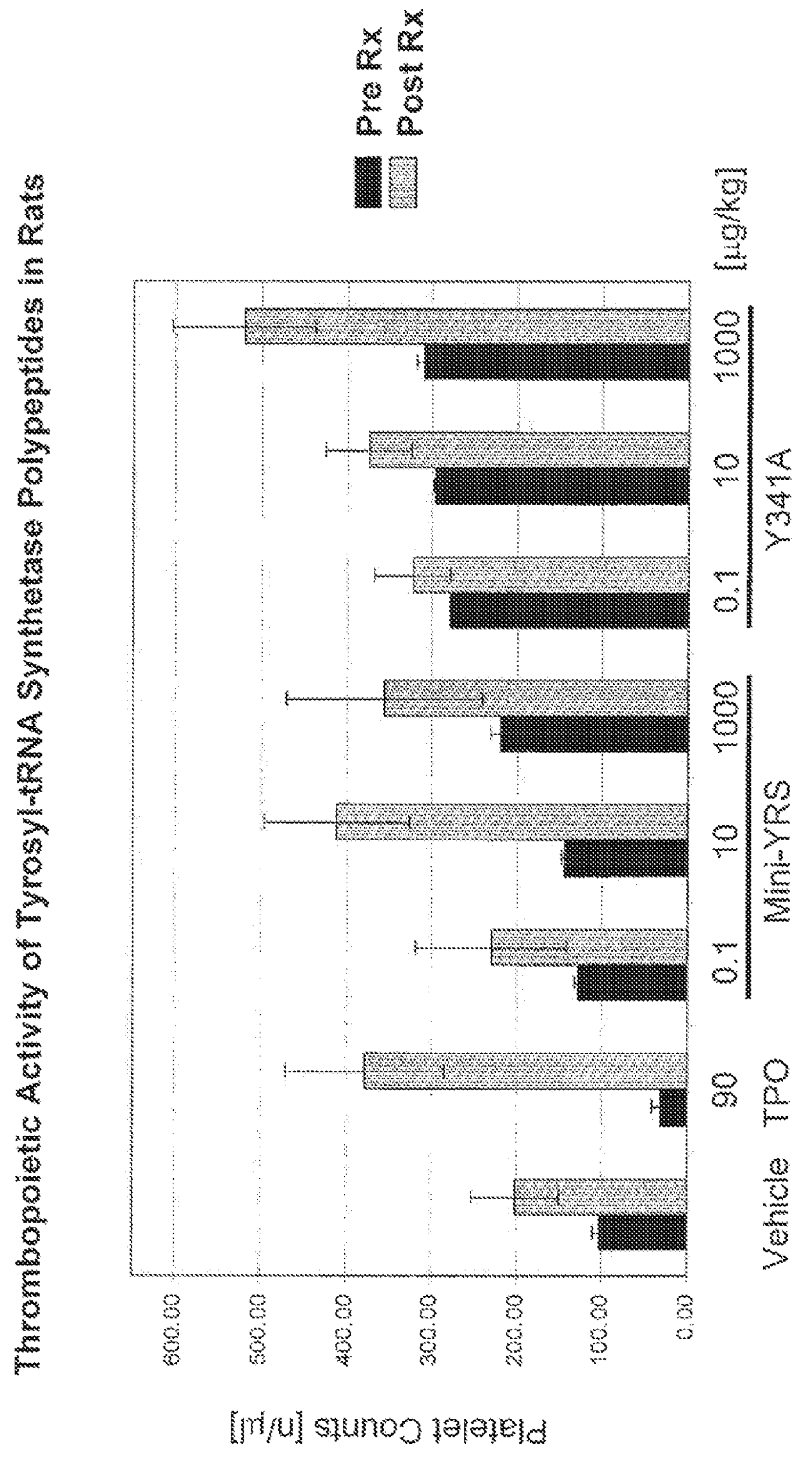
FIG. 20 shows the thrombopoietic activity of YRS polypeptides in rats (see Example 4).

Administration of the two tyrosyl-tRNA synthetase polypeptides resulted in a marked elevation in platelet counts, comparable or superior to that observed in the thrombopoietin group (See FIG. 20). These results show that tyrosyl-tRNA synthetase polypeptides are capable of stimulating thrombopoiesis in vivo.

Example 5

Tyrosyl-tRNA Synthetase Polypeptides are Chemoattractants for Megakaryocytes

Figure 21:
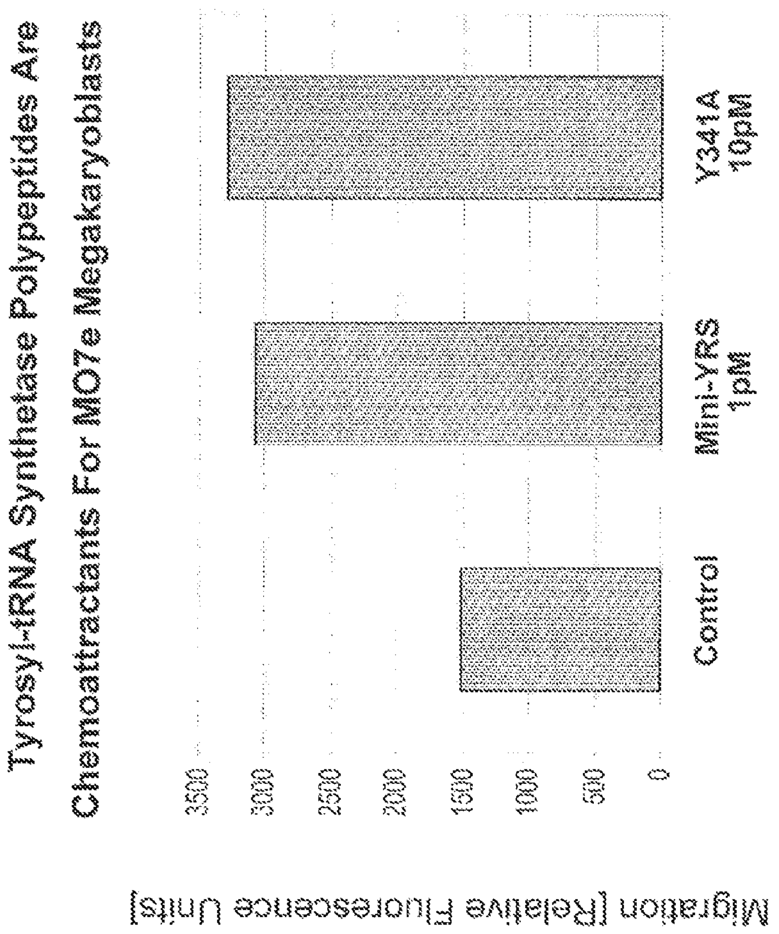
FIG. 21 shows the migration of MO7e megakaryoblasts in response to stimulation by YRS polypeptides (see Example 5).

MO7e cells (DSMZ, Braunschweig, Germany) were cultured in RPMI-1640 medium supplemented with 20% heat-inactivated FBS and 10 ng/ml IL-3 (R&D Systems, Minneapolis, Minn.). Cells were maintained at a density of $2\times10^5$ to $1\times10^6$/ml and RPMI-1640 medium with 0.1% BSA was used as migration buffer. Before the migration assay, cells were serum-starved for 30 minutes in migration buffer and loaded with 8 μg/ml calcein AM (Invitrogen, Carlsbad, Calif.). Cells were spun down at 200 g for 5 minutes without brake and washed once with migration buffer to remove free calcein AM. Cell density was adjusted to $1\times10^7$/ml and 100 μl were added to 6.5 mm transwell 8.0 μm pore filter inserts (Costar, Cambridge, Mass.). 600 μl migration buffer containing either PBS, a control chemokine, or the tyrosyl-tRNA synthetase polypeptides were added to the lower chamber and cells were allowed to migrate for 4 to 16 hours (for the 16-hour migration time, cells were stained after migration). Cells that migrated to the lower chamber were collected and resuspended in 100 μl PBS, transferred into 384-well opaque Greiner plate and counted by fluorescence in a plate reader. FIG. 21 shows that the tyrosyl-tRNA synthetase polypeptides are to stimulate migration of the MO7e megakaryoblasts.

Example 6

Tyrosyl-tRNA Synthetase Polypeptides Promote Cell Adhesion to Endothelial Monolayers by Stimulating Expression of VCAM-1

The ability of YRS polypeptides to stimulate adhesion of THP-1 cells to endothelial monolayers of HUVEC-2 cells was tested. HUVEC-2 cells (BD Biosciences, San Jose, Calif.) were cultured in EGM-2 medium (Lonza, Allendale, N.J.) and used before they reached 10 passages. THP-1 cells (ATCC, Manassas, Va.) were cultured in RPMI-1640 medium supplemented with 10% heat-inactivated FBS and maintained at a density of $2\text{-}4\times10^5$/ml. Cells were seeded at approximately $1\times10^4$ cells/well into fibronectin-coated (10 μg/ml, 2 hours at 37° C.), opaque 96-well plates.

HUVEC-2 cells were grown until a monolayer was formed and then stimulated overnight in EGM-2 medium with either PBS, IL-13 or the tyrosyl-tRNA synthetase polypeptides. THP-1 cells were collected and incubated for 30 minutes in RPMI-1640 serum-free medium containing 0.1% BSA and calcein AM (6 μl/ml). The cells were then washed in RPMI-1640 serum-free medium containing 0.1% BSA and resuspended at a density of $1.5\times10^5$ cells/ml in RPMI medium containing 10% FBS. 100 μl THP-cells were added to the HUVEC monolayer and incubated for 15 minutes. Unbound THP-1 cells were washed with PBS twice and the remaining cells were fixed with 2% formaldehyde and counted by fluorescence in a plate reader.

Figure 22:
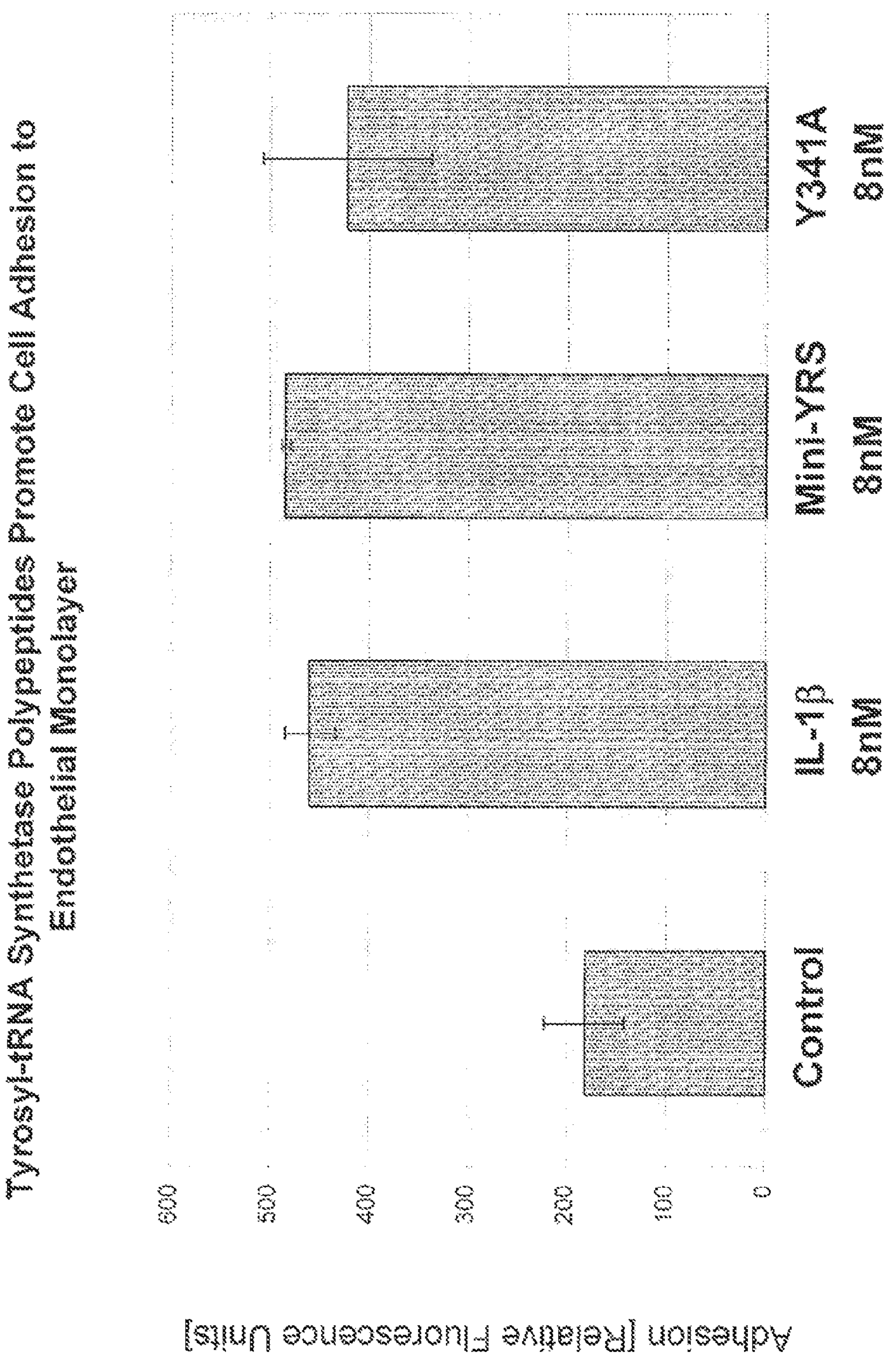
FIG. 22 shows that tyrosyl-tRNA synthetase polypeptides promote cell adhesion of THP-1 cells to endothelial monolayers of HUVEC-2 cells (see Example 6).

FIG. 22 shows adhesion of THP-1 fluorescent cells to an endothelial monolayer that has been treated with the tyrosyl-tRNA synthetase polypeptides Adhesion molecule expression in endothelial monolayers was measured following exposure to tyrosyl-tRNA synthetase polypeptides. $1\times10^4$ HUVEC-2 cells were seeded into a 96-well plate and grown for 48 hours as described in the previous paragraph. Tyrosyl-tRNA synthetase polypeptides, diluted in growth media, were added to the wells and incubated for 16 hours. The culture medium was removed and cells were fixed with 50 μl of Z fix (Anatech Ltd, Battle Creek, Mich.) for 15 minutes at room temperature. Wells were subsequently blocked with 50 μl of casein for 1 hour followed by multiple 200 μl washes with PBS. All subsequent reagents were diluted in casein and all steps were performed at room temperature. Antibodies directed against VCAM-1 and E-selectin (Santa Cruz Biotech, Santa Cruz, Calif.) were added for 1 hour. Wells were then washed as above and an HRP-labeled secondary antibody (Jackson Immunoresearch, West Grove, Pa.) was added for 1 hour. Wells were washed and the substrate for HRP was added. 15 minutes later, an equal volume of 2 M sulfuric acid was added and absorbance determined at 450 nm.

Figure 23:
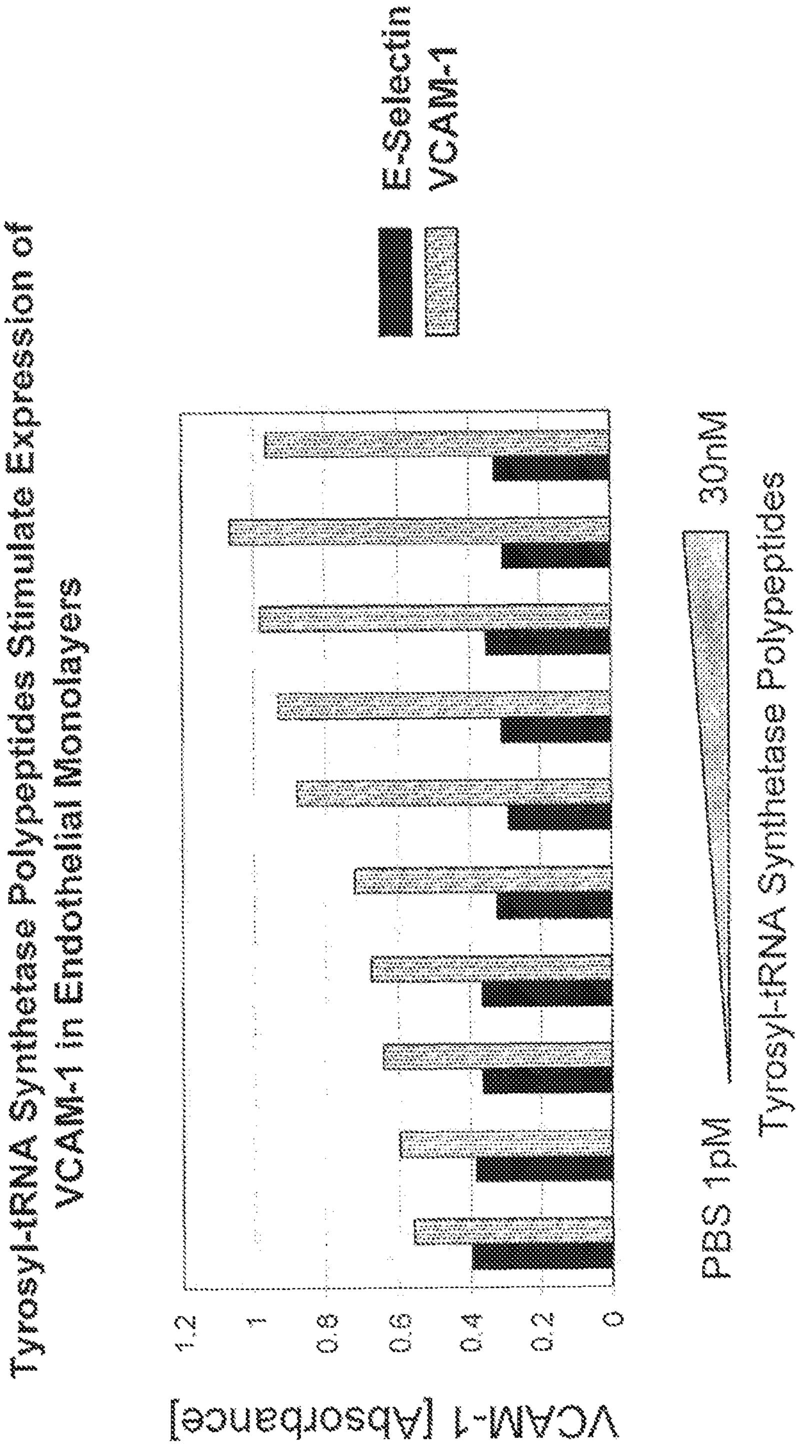
FIG. 23 shows that tyrosyl-tRNA synthetase polypeptides increase expression of adhesion molecule VCAM-1 in endothelial monolayers of HUVEC-2 cells (see Example 6).

FIG. 23 shows an increase in VCAM-1 expression following stimulation of the endothelial cells with the tyrosyl-tRNA synthetase polypeptides.

Example 7

Tyrosyl-tRNA Synthetase Polypeptides Stimulate Migration of 293 and CHO Cell Lines Transfected with the CXCR-2 Receptor The effects of tyrosyl-tRNA synthetase polypeptides on CXCR-2 signaling was tested by measuring the migration of CXCR-2 expressing cells in response to said polypeptides. 293/CXCR-2 cells were maintained in DMEM medium supplemented with 10% heat-inactivated FBS, 1% Penicillin-Streptomycin and 800 μg/ml Geneticin, all purchased from Invitrogen, Carlsbad, Calif. DMEM medium with 0.1% BSA was used as migration buffer. Prior to migration assay, cells were serum-starved for 30 minutes in migration buffer, centrifuged at 200 g for 5 minutes and resuspended in migration buffer at a final density of $1\times10^6$ cells/ml. 100 μl were added to 6.5 mm transwell filter inserts (Costar, Cambridge, Mass.) and 600 μl migration buffer containing a control chemokine, the tyrosyl-tRNA synthetase polypeptides or buffer only were added to the plate lower chambers. Cells were allowed to migrate for 4 hours and the remaining cells in the upper chamber (transwell filter inserts) were removed with a cotton swap. The filter inserts were then transferred to a new 24-well plate containing 500 μl cell dissociation buffer (Invitrogen, Carlsbad, Calif.) and 12 μg/ml Calcein AM (Invitrogen, Carlsbad, Calif.). After 1 hour incubation at 37° C., cells were collected and resuspended in 100 μl PBS, transferred into a 384-well opaque Greiner plate, and counted by fluorescence in a plate reader.

CHO-K1/CXCR-2 cells were maintained in F12 medium supplemented with 10% heat-inactivated FBS, 1% Penicillin-Streptomycin-Glutamine and 800 μg/ml Geneticin. F12 medium with 0.5% BSA was used as migration buffer. Prior to migration, cells were serum-starved for 30 minutes in migration buffer, collected by using cell dissociation buffer, spun down at 200 g for 5 minutes and resuspended in migration buffer at the final density of $1\times10^6$ cells/ml. 100 μl were added to 6.5 mm transwell filter inserts and 600 μl migration buffer containing a control chemokine, the tyrosyl-tRNA synthetase polypeptides or buffer only were added to the plate lower chambers. Cells were allowed to migrate for 3 hours and the remaining cells in the upper chamber (transwell filter inserts) were removed with a cotton swap. The filter inserts were then transferred to a new 24-well plate containing 500 μl PBS and 12 μg/ml Calcein AM. After 30 minutes incubation at 37° C., filters were transferred again into a new 24-well plate containing 500 μl phenol/red-free trypsin. After 2 to 5 minutes incubation, detached cells were collected and resuspended in 100 μl PBS, transferred into a 384 well opaque Greiner plate and counted by fluorescence in a plate reader.

Figure 24:
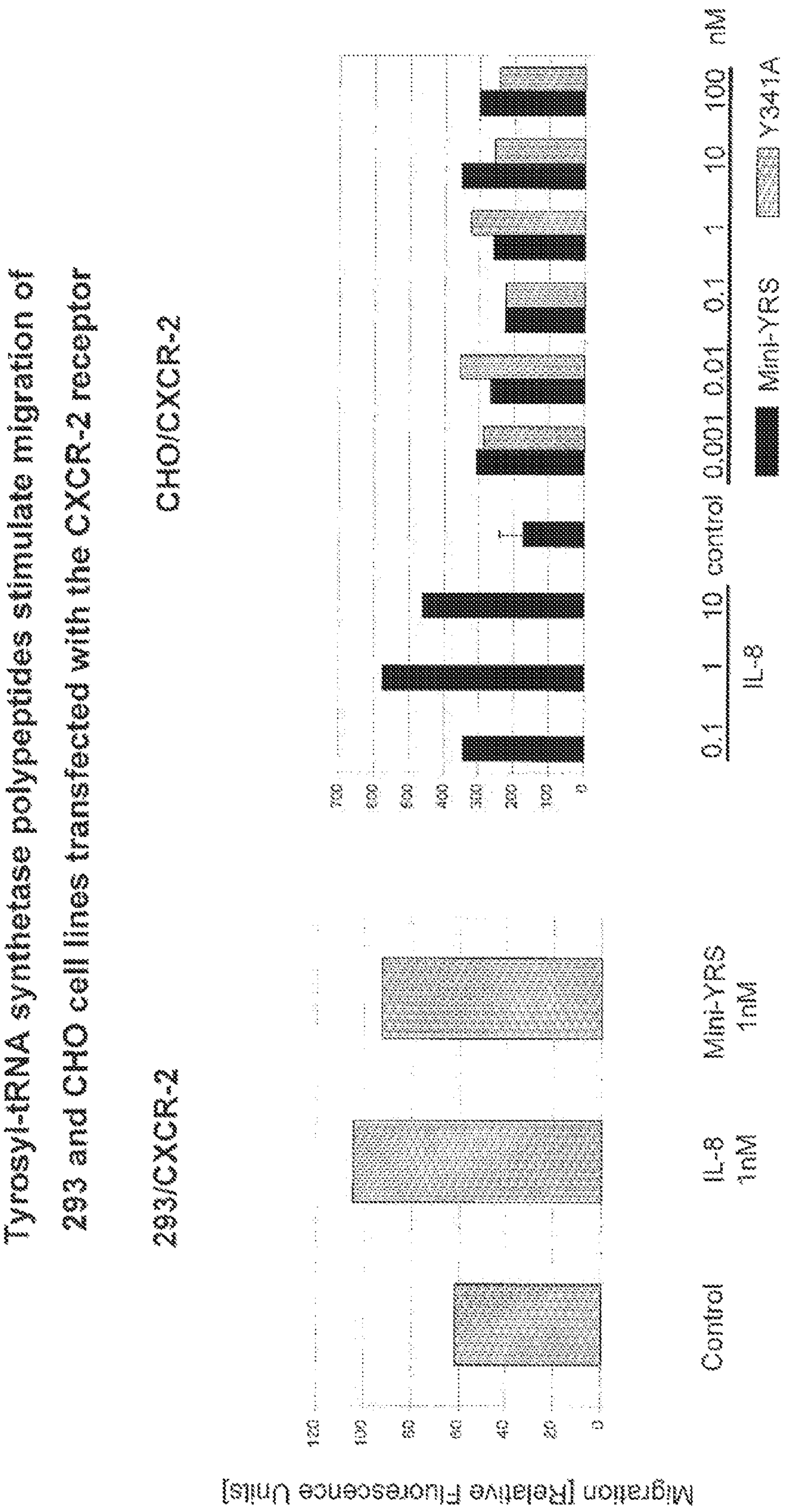
FIG. 24 shows that tyrosyl-tRNA synthetase polypeptides stimulate migration of 293 and CHO cell lines transfected with the CXCR-2 receptor (see Example 7). The left graph in FIG. 24 shows the results for 293/CXCR-2 cells, and the right graph in FIG. 24 shows the results for CHO/CXCR-2 cells.

FIG. 24 demonstrates the ability of the tyrosyl-tRNA synthetase polypeptides to induce migration of CXCR-2 transfected cells.

Example 8

Tyrosyl-tRNA Synthetase Polypeptides Stimulate Polymorphonuclear (PMN) Cell Migration To test the effects of YRS polypeptides on PMN cell migration, human granulocyte cells were purified from fresh human peripheral blood using RosetteSep® Human Granulocyte Enrichment Kit (StemCell Technologies, Vancouver, BC) according to the manufacturer's instructions. Serum-free RPMI medium supplemented with 0.5% FBS was used as migration buffer. $4\times10^7$ cells were resuspended in 1 ml migration buffer and incubated for 30 minutes with 80 μl of a 1 mg/ml Calcein AM solution (Invitrogen, Carlsbad, Calif.). Cells were collected, spun down at 200 g for 5 minutes without brake, washed once with migration buffer and resuspended in the same buffer at a final density of $1\times10^7$/ml.

100 μl were added to 6.5 mm transwell filter inserts (Costar, Cambridge, Mass.) and 600 μl migration buffer containing a control chemokine, the tyrosyl-tRNA synthetase polypeptides or buffer only were added to the plate lower chambers. Cells were allowed to migrate for 45 minutes in the incubator and cells that migrated to the lower chamber were collected, resuspended in 100 μl PBS, transferred into a 384-well opaque Greiner plate and counted by fluorescence in a plate reader.

Figure 25:
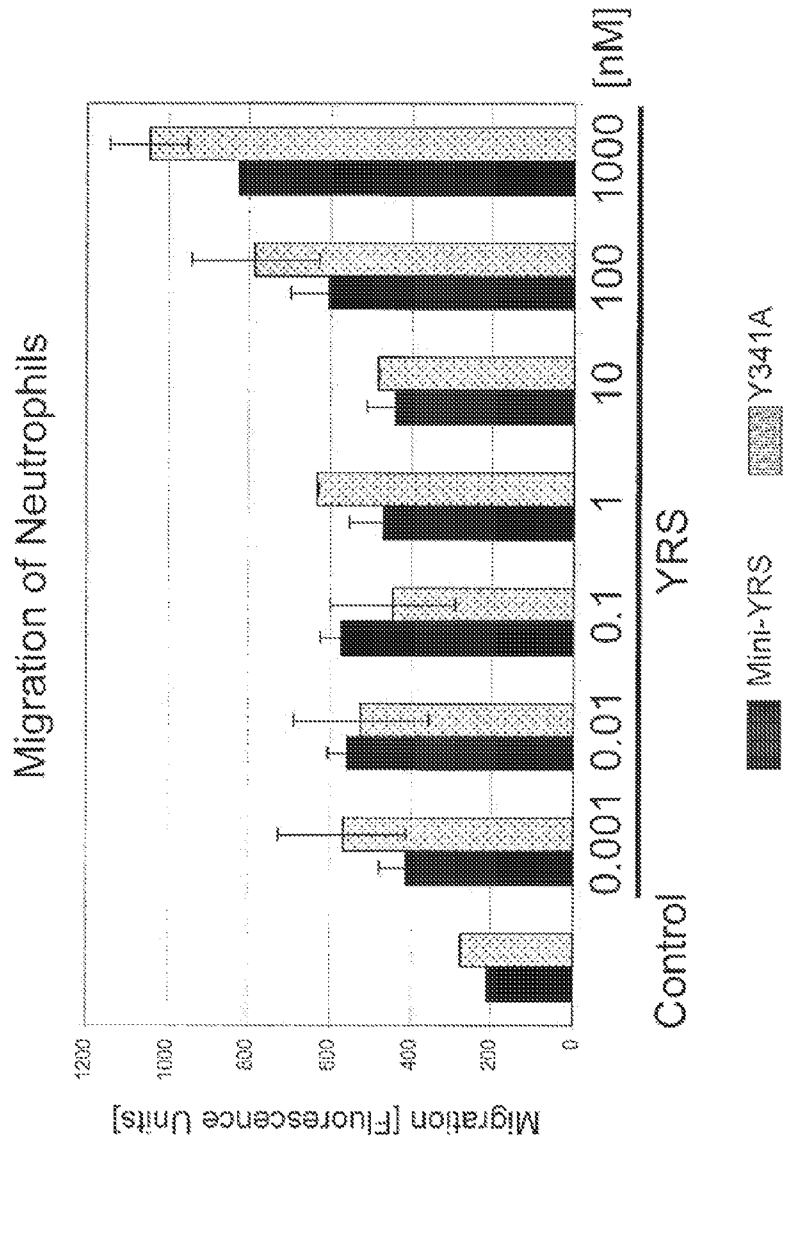
FIG. 25 shows the stimulatory effects of YRS polypeptides on polymorphonuclear (PMN) cell migration (see Example 8).

FIG. 25 shows the bell-shaped migration curve typically observed with chemokines. The tyrosyl-tRNA synthetase polypeptides induced a biphasic migration of PMN both at low pM and at higher μM concentrations.

Example 9

Tyrosyl-tRNA Synthetase Polypeptides Prevent Neutrophil Infiltration into the Lungs after Lipopolysaccharide (LPS) Challenge (Prophetic Example)

Neutrophil migration from the circulatory system to the lungs is implicated in chronic pulmonary obstructive disease (COPD) (see, e.g., R. A. Stockley, *Chest* 121:151S-155S, 2002). CXCR-2 expression can play a role in neutrophil migration (see, e.g., Rios-Santos et al., *American Journal of Respiratory and Critical Care Medicine* 175:490-497, 2007). An animal model is developed to test the role of tyrosyl-tRNA synthetase polypeptides in COPD. The tyrosyl-tRNA synthetase polypeptides are administered to animals intravenously at a concentration and at a frequency necessary to achieve desensitization of circulating neutrophils prior to, and during allergen challenge (e.g., between 100 ng/kg and 5 mg/kg and, e.g., at 12 hours, 1 hour pre-LPS administration and 4 hours post-LPS administration). The animals are then subjected to allergen challenge (e.g., LPS instillation into the lungs via the intranasal route of administration). After 4-8 hours, the animals are euthanized and a tracheal catheter is inserted to collect bronchoalveolar lavage (BAL) samples by flushing the lungs with isotonic saline solution. BAL fluid is analyzed for total cell counts and differential cell enumeration.

In this example, the tyrosyl-tRNA synthetase polypeptides are capable of preventing neutrophil migration to the lung in response to LPS challenge.

Example 10

Tyrosyl-tRNA Synthetase Polypeptides Impact Megakaryocyte Progenitor Cells in Bone Marrow Cell Cultures To test the effects of YRS polypeptides on megakaryocyte progenitor cells in bone marrow cell cultures, clonogenic progenitors of the megakaryocyte (CFU-Mk; Colony Forming Unit—Megakaryocyte) lineage were assessed in serum-free, collagen-based media MegaCult-C® 4950 supplemented with proprietary concentrations of cytokines (StemCell Technologies, Vancouver, BC). Normal human bone marrow light density cells (Lonza, Allendale, N.J.) were stored at −152° C. until required for the assay. On the day of the experiment, cells were thawed rapidly at 37° C., the contents of the vial were diluted in 10 mL of Iscove's modified Dulbecco's medium (IMDM) containing 2% fetal bovine serum (FBS) and washed by centrifugation (1200 rpm for 10 minutes, room temperature). The supernatant was discarded and the cell pellet resuspended in a known volume of IMDM containing 2% FBS. A cell count (3% glacial acetic acid) and viability assessment (trypan blue exclusion test) were performed.

The tyrosyl-tRNA synthetase polypeptides (stored in 50% glycerol/0.5×PBS/2 mM DTT) were dialyzed in 0.5×PBS/2 mM DTT for a total of 5 hours, with one change of buffer after 3 hours in order to remove glycerol. After dialysis, proteins and buffer sample were sterile filtered and concentration was adjusted to compensate for the increase in volume.

Test proteins (YRS polypeptides) were added to tubes of serum-free, collagen-based media MegaCult-C® 4950 supplemented with cytokines (rhTpo, rhIL-3, and rhIL-6). Standard control cultures (containing no test protein) and solvent control cultures (containing no test protein but equivalent concentrations of buffer) were also initiated. Bone marrow cells were then added to each tube of media to give a final concentration of $1\times10^5$ cells per slide. Bovine collagen was then added, tubes were vortexed, and contents dispensed into triplicate double chamber slides. All cultures were incubated for 10-12 days at 37° C., 5% $CO_2$.

Following incubation, cultures were assessed microscopically for colony formation prior to dehydration and fixation of the slide. Using an antibody staining protocol to detect GPIIa/IIb (CD41) expression, the colonies on the slide were stained using an alkaline phosphatase detection system as described in the StemCell Technical Manual, "Assays for the Quantitation of Human and Murine Megakaryocytic Progenitors", Section 7, herein incorporated by reference in its entirety. Colony numbers were scored and assessed by trained StemCell personnel. The colonies were divided into the following categories, based on size and morphology: i) CFU-Mk (2-20)—the small megakaryocytic colony derived from this more mature progenitor cell contains 2-20 cells; ii)

CFU-Mk—the medium megakaryocytic colony derived from this more primitive progenitor cell contains 21-49 cells and; iii) CFU-Mk (>50)—the large megakaryocytic colony derived from this most primitive lineage-restricted progenitor cell contains >50 cells.

Figure 26A:
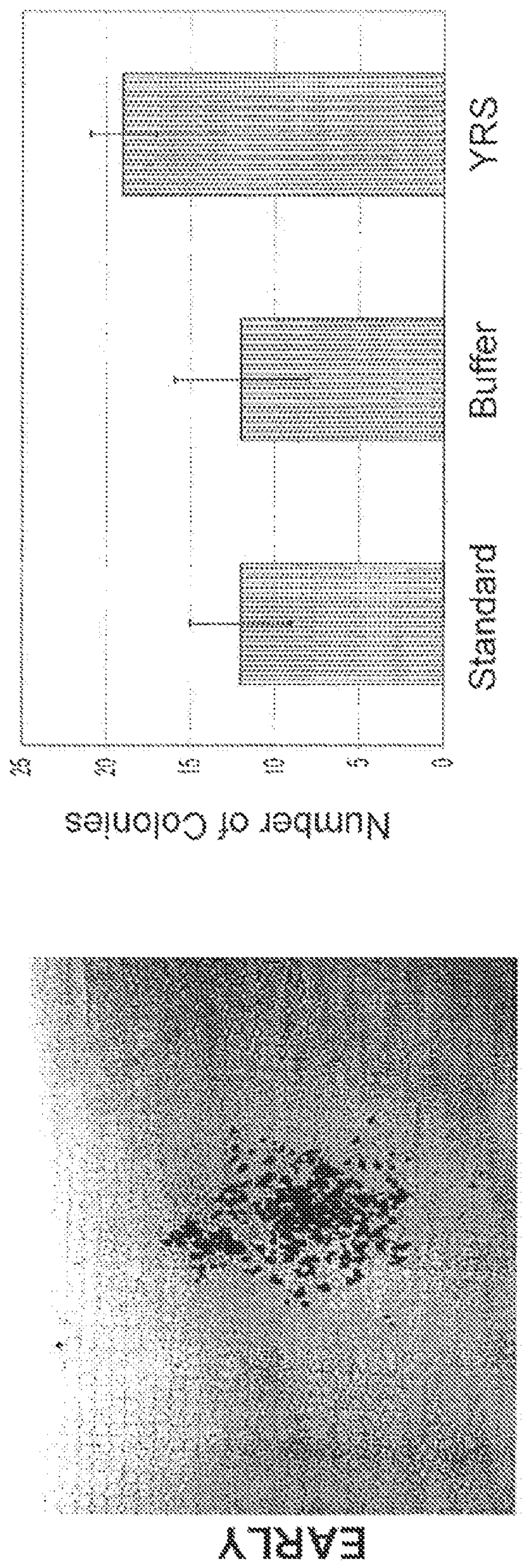
Figure 26B:
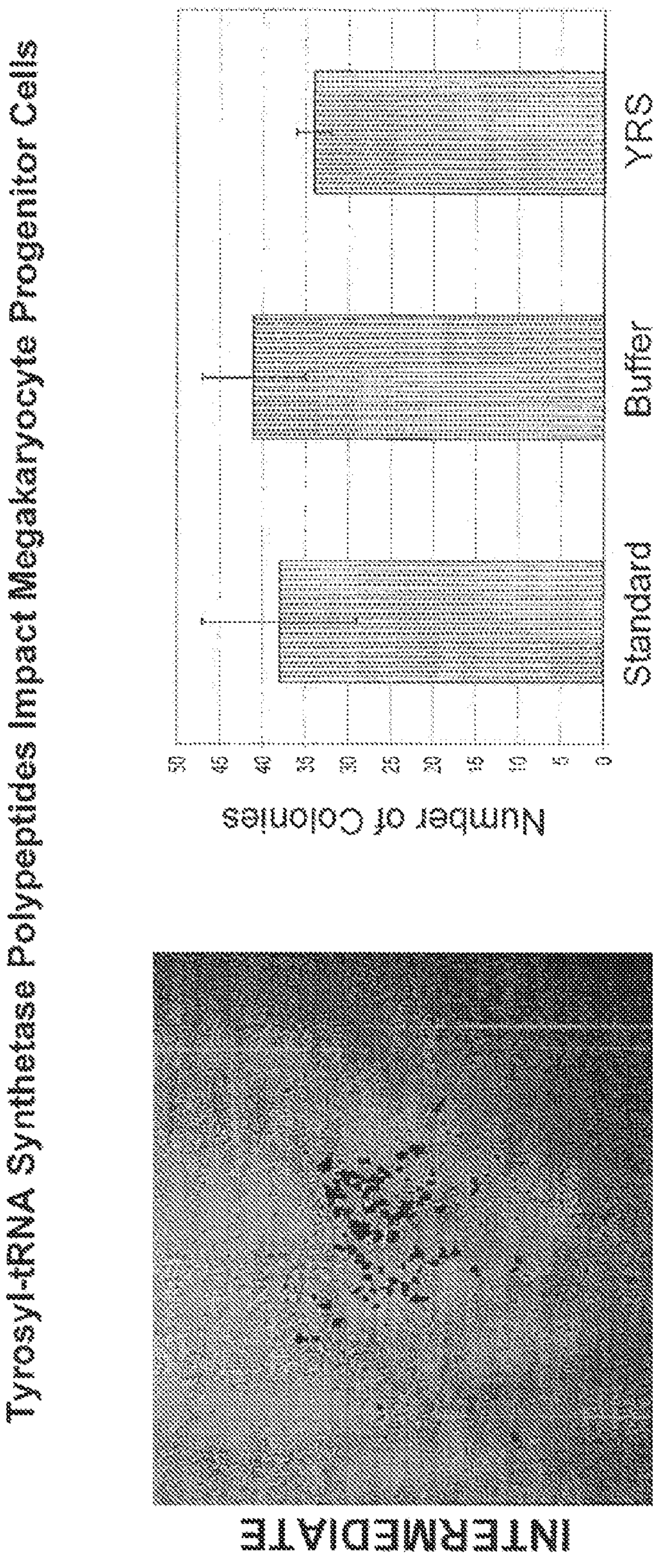

FIGS. 26(A)-26(C) show the impact of the tyrosyl-tRNA synthetase polypeptides on the most primitive lineage-restricted progenitors (stimulation) (FIG. 26(A)), and on the more mature progenitors (inhibition) (FIGS. 26 (B) and (C)).

The invention claimed is:

1. A composition adapted for administration, comprising a physiologically acceptable excipient and/or carrier and a non-naturally occurring tyrosyl-tRNA synthetase polypeptide having a cell-signaling activity, wherein the tyrosyl-tRNA synthetase polypeptide consists of an amino acid sequence at least 95% identical to the amino acid sequence of SEQ ID NO: 6, or 10 or a fragment thereof which is at least 300 contiguous amino acids of SEQ ID NO: 6 or 10.

2. The composition of claim 1, further comprising a second tyrosyl-tRNA synthetase polypeptide, wherein the two tyrosyl-tRNA synthetase polypeptides form a dimer.

3. The composition of claim 2, wherein the dimer is a homodimer.

4. The composition of claim 3, wherein the dimer is a heterodimer.

5. The composition of claim 4, wherein the heterodimer comprises a full-length tyrosyl-tRNA synthetase polypeptide and a truncated tyrosyl-tRNA synthetase polypeptide.

6. The composition of claim 1, further comprising a heterologous polypeptide, wherein the tyrosyl-tRNA synthetase polypeptide and the heterologous polypeptide form a heterodimer or a fusion protein.

7. The composition of claim 1, wherein the tyrosyl-tRNA synthetase polypeptide consists essentially of an amino acid sequence at least 95% identical to SEQ ID NO: 6 or a fragment thereof which is at least 300 contiguous amino acids of SEQ ID NO: 6.

8. The composition of claim 1, wherein the tyrosyl-tRNA synthetase polypeptide consists essentially of an amino acid sequence at least 95% identical to SEQ ID NO: 10 or a fragment thereof which is at least 300 contiguous amino acids of SEQ ID NO: 10.

9. The composition of claim 1, wherein the tyrosyl-tRNA synthetase polypeptide consists essentially of SEQ ID NO: 6.

10. The composition of claim 1, wherein the tyrosyl-tRNA synthetase polypeptide consists essentially of SEQ ID NO: 10.

* * * * *

SEQUENCE LISTING

```
<160> NUMBER OF SEQ ID NOS: 15

<210> SEQ ID NO 1
<211> LENGTH: 528
<212> TYPE: PRT
<213> ORGANISM: Homo sapiens

<400> SEQUENCE: 1

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335
```

```
Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile Pro Ser Arg Leu
        355                 360                 365

Asp Ile Arg Val Gly Lys Ile Ile Thr Val Glu Lys His Pro Asp Ala
    370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Val Leu Cys Asn Leu Lys Pro Gln Lys Met Arg
            420                 425                 430

Gly Val Glu Ser Gln Gly Met Leu Leu Cys Ala Ser Ile Glu Gly Ile
        435                 440                 445

Asn Arg Gln Val Glu Pro Leu Asp Pro Pro Ala Gly Ser Ala Pro Gly
    450                 455                 460

Glu His Val Phe Val Lys Gly Tyr Glu Lys Gly Gln Pro Asp Glu Glu
465                 470                 475                 480

Leu Lys Pro Lys Lys Lys Val Phe Glu Lys Leu Gln Ala Asp Phe Lys
                485                 490                 495

Ile Ser Glu Glu Cys Ile Ala Gln Trp Lys Gln Thr Asn Phe Met Thr
            500                 505                 510

Lys Leu Gly Ser Ile Ser Cys Lys Ser Leu Lys Gly Gly Asn Ile Ser
        515                 520                 525


<210> SEQ ID NO 2
<211> LENGTH: 528
<212> TYPE: PRT
<213> ORGANISM: Homo sapiens

<400> SEQUENCE: 2

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
```

-continued

```
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Ala Pro Asp Pro Ser Lys Gln Lys Pro Met Ala Lys
            340                 345                 350

Gly Pro Ala Lys Asn Ser Glu Pro Glu Glu Val Ile Pro Ser Arg Leu
        355                 360                 365

Asp Ile Arg Val Gly Lys Ile Ile Thr Val Glu Lys His Pro Asp Ala
    370                 375                 380

Asp Ser Leu Tyr Val Glu Lys Ile Asp Val Gly Glu Ala Glu Pro Arg
385                 390                 395                 400

Thr Val Val Ser Gly Leu Val Gln Phe Val Pro Lys Glu Glu Leu Gln
                405                 410                 415

Asp Arg Leu Val Val Val Leu Cys Asn Leu Lys Pro Gln Lys Met Arg
            420                 425                 430

Gly Val Glu Ser Gln Gly Met Leu Leu Cys Ala Ser Ile Glu Gly Ile
        435                 440                 445

Asn Arg Gln Val Glu Pro Leu Asp Pro Pro Ala Gly Ser Ala Pro Gly
    450                 455                 460

Glu His Val Phe Val Lys Gly Tyr Glu Lys Gly Gln Pro Asp Glu Glu
465                 470                 475                 480

Leu Lys Pro Lys Lys Lys Val Phe Glu Lys Leu Gln Ala Asp Phe Lys
                485                 490                 495

Ile Ser Glu Glu Cys Ile Ala Gln Trp Lys Gln Thr Asn Phe Met Thr
            500                 505                 510

Lys Leu Gly Ser Ile Ser Cys Lys Ser Leu Lys Gly Gly Asn Ile Ser
        515                 520                 525


<210> SEQ ID NO 3
<211> LENGTH: 364
<212> TYPE: PRT
<213> ORGANISM: Homo sapiens

<400> SEQUENCE: 3

Met Gly Asp Ala Pro Ser Pro Glu Glu Lys Leu His Leu Ile Thr Arg
1               5                   10                  15

Asn Leu Gln Glu Val Leu Gly Glu Glu Lys Leu Lys Glu Ile Leu Lys
            20                  25                  30
```

-continued

```
Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Pro Ala Lys Asn Ser Glu Pro Glu Glu Val Ile
        355                 360
```

<210> SEQ ID NO 4
<211> LENGTH: 1683
<212> TYPE: DNA
<213> ORGANISM: Homo sapiens

<400> SEQUENCE: 4

```
atgggggacg ctcccagccc tgaagagaaa ctgcacctta tcacccggaa cctgcaggag      60

gttctggggg aagagaagct gaaggagata ctgaaggagc gggaacttaa aatttactgg     120

ggaacggcaa ccacgggcaa accacatgtg gcttactttg tgcccatgtc aaagattgca     180

gacttcttaa aggcagggtg tgaggtaaca attctgtttg cggacctcca cgcatacctg     240
```

-continued

```
gataacatga aagccccatg ggaacttcta gaactccgag tcagttacta tgagaatgtg    300

atcaaagcaa tgctggagag cattggtgtg cccttggaga agctcaagtt catcaaaggc    360

actgattacc agctcagcaa agagtacaca ctagatgtgt acagactctc ctccgtggtc    420

acacagcacg attccaagaa ggctggagct gaggtggtaa agcaggtgga gcaccctttg    480

ctgagtggcc tcttataccc cggactgcag gctttggatg aagagtattt aaaagtagat    540

gcccaatttg gaggcattga tcagagaaag attttcacct ttgcagagaa gtacctccct    600

gcacttggct attcaaaacg ggtccatctg atgaatccta tggttccagg attaacaggc    660

agcaaaatga gctcttcaga agaggagtcc aagattgatc tccttgatcg gaaggaggat    720

gtgaagaaaa aactgaagaa ggccttctgt gagccaggaa atgtggagaa caatggggtt    780

ctgtccttca tcaagcatgt cctttttccc cttaagtccg agtttgtgat cctacgagat    840

gagaaatggg gtggaaacaa aacctacaca gcttacgtgg acctggaaaa ggactttgct    900

gctgaggttg tacatcctgg agacctgaag aattctgttg aagtcgcact gaacaagttg    960

ctggatccaa tccgggaaaa gtttaatacc cctgccctga aaaaactggc cagcgctgcc   1020

tacccagatc cctcaaagca gaagccaatg gccaaaggcc ctgccaagaa ttcagaacca   1080

gaggaggtca tcccatcccg gctggatatc cgtgtgggga aaatcatcac tgtggagaag   1140

cacccagatg cagacagcct gtatgtagag aagattgacg tgggggaagc tgaaccacgg   1200

actgtggtga gcggcctggt acagttcgtg cccaaggagg aactgcagga caggctggta   1260

gtggtgctgt gcaacctgaa accccagaag atgagaggag tcgagtccca aggcatgctt   1320

ctgtgtgctt ctatagaagg gataaaccgc caggttgaac ctctggaccc tccggcaggc   1380

tctgctcctg gtgagcacgt gtttgtgaag ggctatgaaa agggccaacc agatgaggag   1440

ctcaagccca agaagaaagt cttcgagaag ttgcaggctg acttcaaaat ttctgaggag   1500

tgcatcgcac agtggaagca aaccaacttc atgaccaagc tgggctccat ttcctgtaaa   1560

tcgctgaaag gggggaacat tagctagcca gcccagcatc ttcccccctt cttccaccac   1620

tgagtcatct gctgtctctt cagtctgctc catccatcac ccatttaccc atctctcagg   1680

aca                                                                 1683


<210> SEQ ID NO 5
<211> LENGTH: 8
<212> TYPE: PRT
<213> ORGANISM: Artificial Sequence
<220> FEATURE:
<223> OTHER INFORMATION: C-terminal tag

<400> SEQUENCE: 5

Leu Glu His His His His His His
1               5


<210> SEQ ID NO 6
<211> LENGTH: 348
<212> TYPE: PRT
<213> ORGANISM: Homo sapiens
<220> FEATURE:
<221> NAME/KEY: VARIANT
<222> LOCATION: (1)..(9)
<223> OTHER INFORMATION: Xaa = Any Amino Acid

<400> SEQUENCE: 6

Xaa Xaa Xaa Xaa Xaa Xaa Xaa Xaa Xaa Lys Ile Phe Thr Phe Ala Glu
1               5                   10                  15

Lys Tyr Leu Pro Ala Leu Gly Tyr Ser Lys Arg Val His Leu Met Asn
```

```
            20                  25                  30

Pro Met Val Pro Gly Leu Thr Gly Ser Lys Met Ser Ser Ser Glu Glu
        35                  40                  45

Glu Ser Lys Ile Asp Leu Leu Asp Arg Lys Glu Asp Val Lys Lys Lys
    50                  55                  60

Leu Lys Lys Ala Phe Cys Glu Pro Gly Asn Val Glu Asn Asn Gly Val
65                  70                  75                  80

Leu Ser Phe Ile Lys His Val Leu Phe Pro Leu Lys Ser Glu Phe Val
                85                  90                  95

Ile Leu Arg Asp Glu Lys Trp Gly Gly Asn Lys Thr Tyr Thr Ala Tyr
            100                 105                 110

Val Asp Leu Glu Lys Asp Phe Ala Ala Glu Val Val His Pro Gly Asp
        115                 120                 125

Leu Lys Asn Ser Val Glu Val Ala Leu Asn Lys Leu Leu Asp Pro Ile
    130                 135                 140

Arg Glu Lys Phe Asn Thr Pro Ala Leu Lys Lys Leu Ala Ser Ala Ala
145                 150                 155                 160

Tyr Pro Asp Pro Ser Lys Gln Lys Pro Met Ala Lys Gly Pro Ala Lys
                165                 170                 175

Asn Ser Glu Pro Glu Glu Val Ile Pro Ser Arg Leu Asp Ile Arg Val
            180                 185                 190

Gly Lys Ile Ile Thr Val Glu Lys His Pro Asp Ala Asp Ser Leu Tyr
        195                 200                 205

Val Glu Lys Ile Asp Val Gly Glu Ala Glu Pro Arg Thr Val Val Ser
    210                 215                 220

Gly Leu Val Gln Phe Val Pro Lys Glu Glu Leu Gln Asp Arg Leu Val
225                 230                 235                 240

Val Val Leu Cys Asn Leu Lys Pro Gln Lys Met Arg Gly Val Glu Ser
                245                 250                 255

Gln Gly Met Leu Leu Cys Ala Ser Ile Glu Gly Ile Asn Arg Gln Val
            260                 265                 270

Glu Pro Leu Asp Pro Pro Ala Gly Ser Ala Pro Gly Glu His Val Phe
        275                 280                 285

Val Lys Gly Tyr Glu Lys Gly Gln Pro Asp Glu Glu Leu Lys Pro Lys
    290                 295                 300

Lys Lys Val Phe Glu Lys Leu Gln Ala Asp Phe Lys Ile Ser Glu Glu
305                 310                 315                 320

Cys Ile Ala Gln Trp Lys Gln Thr Asn Phe Met Thr Lys Leu Gly Ser
                325                 330                 335

Ile Ser Cys Lys Ser Leu Lys Gly Gly Asn Ile Ser
            340                 345


<210> SEQ ID NO 7
<211> LENGTH: 2178
<212> TYPE: DNA
<213> ORGANISM: Homo sapiens

<400> SEQUENCE: 7

ttcagaaagt ggtggaggga agacttcctt tttcccagag acagaaggtt atgcacccag      60

tggcctggga ccattgttct gggctttttt tcccttcgac atggatttgc ttctcactgt     120

gtaccccaac caccaaaacc accctgagat caatgctggt gctcctgcat cagatggctt     180

agagatcctt ccacctctta acacaagcat ctaggtccac tttactcaaa tctggcctca     240

gttgagagca gagtatacca tcagagccca ttctcctgtc tgctgtctgg gacgtggaaa     300
```

-continued

```
gaaagttagc tctagggggt ctttccaggg gcctctgtaa ggactggatg ctcctttccg    360

gaatccaaga gttcaccagg ctgcttctct aatggacgat gatcctcttc ctcctgacgt    420

ctctccctgg cagcacccag atgcagacag cctgtatgta gagaagattg acgtggggga    480

agctgaacca cggactgtgg tgagcggcct ggtacagttc gtgcccaagg aggaactgca    540

ggacaggctg gtagtggtgc tgtgcaacct gaaaccccag aagatgagag gagtcgagtc    600

ccaaggcatg cttctgtgtg cttctatgtg agtgaggact tggagtgggg cacaggacct    660

ggggaggcca ggaagagtag ggaatcagcc catatgatgt ccttccacac accaggtgga    720

agctctgaga acacgtgcct cttccttgct gatgccaaaa gttgatgcat gaaggactta    780

tcgtacaagt actgttaatg aagcatttta cctacagtta attttgttaa aatagaaatg    840

gagggctcaa accagtacat acccaagtct tactactagt aaggagtgga gcagggattc    900

aaatcccagt tttgatgtct ataaagtcct cgctacgtta ttttatactt cctcccctag    960

aaacacagat tttggtatct tgacacacaa ttttggtata gcctgggtta atgtaaccct   1020

ggtgatatgc agggatgtag caagataaga ggacctcctg gggctctggt actgaggatg   1080

ccctaaatcc catcagggcc cctgtgtaaa ggcccggatt gctttggcct ccacagtcac   1140

tggaacccat ccatagcctc actcttctct tgtcctgtgt cttcccagag aagggataaa   1200

ccgccaggtt gaacctctgg accctccggc aggctctgct cctggtgagc acgtgtttgt   1260

gaagggctat gaaaagggcc aaccagatga ggagctcaag cccaagagga aagtcttcga   1320

gaagttgcag gctgacttca aaatttctga ggagtgcatc gcacagtgga agcaaaccaa   1380

cttcatgacc aagctgggct ccatttcctg taaatcgctg aaagggggga acattagcta   1440

gccagcccag catcttcccc ccttcttcca ccactgagtc atctgctgtc tcttcagtct   1500

gctccaccca tcacccattt acccatctct caggacacgg aagcagcggg tttggactct   1560

ttattcggtg cagaactcgg caaggggcag cttaccctcc ccagaaccca ggatcatcct   1620

gtctggctgc agtgagagac caacccctaa caagggctgg gccacagcag ggagtccagc   1680

cctaccttct tcccttggca gctggagaaa tctggtttca atataactca tttaaaaatt   1740

tatgccacag tccttataat tggaaaaata ctggtgccca ggttttcttg gagttatcca   1800

agcagctgcg cccctagctg ggatctggta cctggactag gctaattaca gcttctcccc   1860

aacaggaaac tgtgggattt gaaaaggaaa gggaagggaa aacagagaac ctagtggtct   1920

accaagtggt tggcaacttt cccaatgtct gcttactctg aggcttggca ctgggggcca   1980

gggcctgccc cagggctcct ggaatttccc ttgatccagc taggctggga cactccctaa   2040

atcagctgcg tgttgttagc atcaggcaga atgaatggca gagagtgatt ctgtcttcat   2100

agagggtggg gtacttctcc ataaggcatc tcagtcaaat ccccatcact gtcataaatt   2160

caaataaaat gtctgaac                                                 2178
```

<210> SEQ ID NO 8
<211> LENGTH: 388
<212> TYPE: PRT
<213> ORGANISM: Homo sapiens
<220> FEATURE:
<221> NAME/KEY: VARIANT
<222> LOCATION: (354)..(388)
<223> OTHER INFORMATION: Xaa = Any Amino Acid

<400> SEQUENCE: 8

```
Met Gly Asp Ala Pro Ser Pro Glu Glu Lys Leu His Leu Ile Thr Arg
1               5                   10                  15
```

```
Asn Leu Gln Glu Val Leu Gly Glu Glu Lys Leu Lys Glu Ile Leu Lys
            20                  25                  30

Glu Arg Glu Leu Lys Ile Tyr Trp Gly Thr Ala Thr Thr Gly Lys Pro
        35                  40                  45

His Val Ala Tyr Phe Val Pro Met Ser Lys Ile Ala Asp Phe Leu Lys
    50                  55                  60

Ala Gly Cys Glu Val Thr Ile Leu Phe Ala Asp Leu His Ala Tyr Leu
65                  70                  75                  80

Asp Asn Met Lys Ala Pro Trp Glu Leu Leu Glu Leu Arg Val Ser Tyr
                85                  90                  95

Tyr Glu Asn Val Ile Lys Ala Met Leu Glu Ser Ile Gly Val Pro Leu
            100                 105                 110

Glu Lys Leu Lys Phe Ile Lys Gly Thr Asp Tyr Gln Leu Ser Lys Glu
        115                 120                 125

Tyr Thr Leu Asp Val Tyr Arg Leu Ser Ser Val Val Thr Gln His Asp
    130                 135                 140

Ser Lys Lys Ala Gly Ala Glu Val Val Lys Gln Val Glu His Pro Leu
145                 150                 155                 160

Leu Ser Gly Leu Leu Tyr Pro Gly Leu Gln Ala Leu Asp Glu Glu Tyr
                165                 170                 175

Leu Lys Val Asp Ala Gln Phe Gly Gly Ile Asp Gln Arg Lys Ile Phe
            180                 185                 190

Thr Phe Ala Glu Lys Tyr Leu Pro Ala Leu Gly Tyr Ser Lys Arg Val
        195                 200                 205

His Leu Met Asn Pro Met Val Pro Gly Leu Thr Gly Ser Lys Met Ser
    210                 215                 220

Ser Ser Glu Glu Glu Ser Lys Ile Asp Leu Leu Asp Arg Lys Glu Asp
225                 230                 235                 240

Val Lys Lys Lys Leu Lys Lys Ala Phe Cys Glu Pro Gly Asn Val Glu
                245                 250                 255

Asn Asn Gly Val Leu Ser Phe Ile Lys His Val Leu Phe Pro Leu Lys
            260                 265                 270

Ser Glu Phe Val Ile Leu Arg Asp Glu Lys Trp Gly Gly Asn Lys Thr
        275                 280                 285

Tyr Thr Ala Tyr Val Asp Leu Glu Lys Asp Phe Ala Ala Glu Val Val
    290                 295                 300

His Pro Gly Asp Leu Lys Asn Ser Val Glu Val Ala Leu Asn Lys Leu
305                 310                 315                 320

Leu Asp Pro Ile Arg Glu Lys Phe Asn Thr Pro Ala Leu Lys Lys Leu
                325                 330                 335

Ala Ser Ala Ala Tyr Pro Asp Pro Ser Lys Gln Lys Pro Met Ala Lys
            340                 345                 350

Gly Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
    370                 375                 380

Xaa Xaa Xaa Xaa
385
```

<210> SEQ ID NO 9
<211> LENGTH: 1167
<212> TYPE: DNA
<213> ORGANISM: Homo sapiens -continued

<400> SEQUENCE: 9

```
atgggggacg ctcccagccc tgaagagaaa ctgcacctta tcacccggaa cctgcaggag     60
gttctggggg aagagaagct gaaggagata ctgaaggagc gggaacttaa aatttactgg    120
ggaacggcaa ccacgggcaa accacatgtg gcttactttg tgcccatgtc aaagattgca    180
gacttcttaa aggcagggtg tgaggtaaca attctgtttg cggacctcca cgcatacctg    240
gataacatga aagccccatg ggaacttcta gaactccgag tcagttacta tgagaatgtg    300
atcaaagcaa tgctggagag cattggtgtg cccttggaga agctcaagtt catcaaaggc    360
actgattacc agctcagcaa agagtacaca ctagatgtgt acagactctc ctccgtggtc    420
acacagcacg attccaagaa ggctggagct gaggtggtaa agcaggtgga gcaccctttg    480
ctgagtggcc tcttataccc cggactgcag gctttggatg aagagtattt aaaagtagat    540
gcccaatttg gaggcattga tcagagaaag attttcacct ttgcagagaa gtacctccct    600
gcacttggct attcaaaacg ggtccatctg atgaatccta tggttccagg attaacaggc    660
agcaaaatga gctcttcaga agaggagtcc aagattgatc tccttgatcg gaaggaggat    720
gtgaagaaaa aactgaagaa ggccttctgt gagccaggaa atgtggagaa caatggggtt    780
ctgtccttca tcaagcatgt cctttttccc cttaagtccg agtttgtgat cctacgagat    840
gagaaatggg gtggaaacaa aacctacaca gcttacgtgg acctggaaaa ggactttgct    900
gctgaggttg tacatcctgg agacctgaag aattctgttg aagtcgcact gaacaagttg    960
ctggatccaa tccgggaaaa gtttaatacc cctgccctga aaaaactggc cagcgctgcc   1020
tacccagatc cctcaaagca gaagccaatg gccaaaggcc tgccaagaat tcagaaccag   1080
aggaggtcat cccatcccgg ctggatatcc gtgtggggaa aatcatcact gtggagaagc   1140
acccagatgc agacagcctg tatgtag                                       1167
```

<210> SEQ ID NO 10
<211> LENGTH: 318
<212> TYPE: PRT
<213> ORGANISM: Homo sapiens

<400> SEQUENCE: 10

```
Met Asn Pro Met Val Pro Gly Leu Thr Gly Ser Lys Met Ser Ser Ser
1               5                   10                  15

Glu Glu Glu Ser Lys Ile Asp Leu Leu Asp Arg Lys Glu Asp Val Lys
            20                  25                  30

Lys Lys Leu Lys Lys Ala Phe Cys Glu Pro Gly Asn Val Glu Asn Asn
        35                  40                  45

Gly Val Leu Ser Phe Ile Lys His Val Leu Phe Pro Leu Lys Ser Glu
    50                  55                  60

Phe Val Ile Leu Arg Asp Glu Lys Trp Gly Gly Asn Lys Thr Tyr Thr
65                  70                  75                  80

Ala Tyr Val Asp Leu Glu Lys Asp Phe Ala Ala Glu Val Val His Pro
                85                  90                  95

Gly Asp Leu Lys Asn Ser Val Glu Val Ala Leu Asn Lys Leu Leu Asp
            100                 105                 110

Pro Ile Arg Glu Lys Phe Asn Thr Pro Ala Leu Lys Lys Leu Ala Ser
        115                 120                 125

Ala Ala Tyr Pro Asp Pro Ser Lys Gln Lys Pro Met Ala Lys Gly Pro
    130                 135                 140

Ala Lys Asn Ser Glu Pro Glu Glu Val Ile Pro Ser Arg Leu Asp Ile
145                 150                 155                 160
```

```
Arg Val Gly Lys Ile Ile Thr Val Glu Lys His Pro Asp Ala Asp Ser
                165                 170                 175

Leu Tyr Val Glu Lys Ile Asp Val Gly Glu Ala Glu Pro Arg Thr Val
            180                 185                 190

Val Ser Gly Leu Val Gln Phe Val Pro Lys Glu Glu Leu Gln Asp Arg
        195                 200                 205

Leu Val Val Val Leu Cys Asn Leu Lys Pro Gln Lys Met Arg Gly Val
    210                 215                 220

Glu Ser Gln Gly Met Leu Leu Cys Ala Ser Ile Glu Gly Ile Asn Arg
225                 230                 235                 240

Gln Val Glu Pro Leu Asp Pro Pro Ala Gly Ser Ala Pro Gly Glu His
                245                 250                 255

Val Phe Val Lys Gly Tyr Glu Lys Gly Gln Pro Asp Glu Glu Leu Lys
            260                 265                 270

Pro Lys Lys Lys Val Phe Glu Lys Leu Gln Ala Asp Phe Lys Ile Ser
        275                 280                 285

Glu Glu Cys Ile Ala Gln Trp Lys Gln Thr Asn Phe Met Thr Lys Leu
    290                 295                 300

Gly Ser Ile Ser Cys Lys Ser Leu Lys Gly Gly Asn Ile Ser
305                 310                 315
```

<210> SEQ ID NO 11
<211> LENGTH: 1736
<212> TYPE: DNA
<213> ORGANISM: Homo sapiens

<400> SEQUENCE: 11

```
gaaagatttt cacctttgca gagaagtacc tccctgcact tggctattca aaacgggtcc     60

atctgatgaa tcctatggtt ccaggattaa caggcagcaa aatgagctct tcagaagagg    120

agtccaagat tgatctcctt gatcggaagg aggatgtgaa gaaaaaactg aagaaggcct    180

tctgtgagcc aggaaatgtg gagaacaatg gggttctgtc cttcatcaag catgtccttt    240

ttccccttaa gtccgagttt gtgatcctac gagatgagaa atggggtgga aacaaaacct    300

acacagctta cgtggacctg gaaaaggact ttgctgctga ggttgtacat cctggagacc    360

tgaagaattc tgttgaagtc gcactgaaca agttgctgga tccaatccgg gaaaagttta    420

atacccctgc cctgaaaaaa ctggccagcg ctgcctaccc agatccctca aagcagaagc    480

caatggccaa aggccctgcc aagaattcag aaccagagga ggtcatccca tcccggctgg    540

atatccgtgt ggggaaaatc atcactgtgg agaagcaccc agatgcagac agcctgtatg    600

tagagaagat tgacgtgggg gaagctgaac cacggactgt ggtgagcggc ctggtacagt    660

tcgtgcccaa ggaggaactg caggacaggc tggtagtggt gctgtgcaac ctgaaacccc    720

agaagatgag aggagtcgag tcccaaggca tgcttctgtg tgcttctata gaagggataa    780

accgccaggt tgaacctctg gaccctccgg caggctctgc tcctggtgag cacgtgtttg    840

tgaagggcta tgaaaagggc caaccagatg aggagctcaa gcccaagaag aaagtcttcg    900

agaagttgca ggctgacttc aaaatttctg aggagtgcat cgcacagtgg aagcaaacca    960

acttcatgac caagctgggc tccatttcct gtaaatcgct gaaagggggg aacattagct   1020

agccagccca gcatcttccc cccttcttcc accactgagt catctgctgt ctcttcagtc   1080

tgctccatcc atcacccatt tacccatctc tcaggacacg gaagcagcgg gtttggactc   1140

tttattcggt gcagaactcg gcaaggggca gcttaccctc cccagaaccc aggatcatcc   1200
```

-continued

```
tgtctggctg cagtgagaga ccaaccccta acaagggctg ggccacagca gggagtccag   1260

ccctaccttc ttcccttggc agctggagaa atctggtttc aatataactc atttaaaaat   1320

ttatgccaca gtccttataa ttggaaaaat actggtgccc aggttttctt ggagttatcc   1380

aagcagctgc gcccctagct gggatctggt acctggacta ggctaattac agcttctccc   1440

caacaggaaa ctgtgggatt tgaaaaggaa agggaaggga aaacagagaa cctagtggtc   1500

taccaagtgg ttggcaactt tcccaatgtc tgcttactct gaggcttggc actgggggcc   1560

agggcctgcc ccagggctcc tggaatttcc cttgatccag ctaggctggg acactcccta   1620

aatcagctgc gtgttgttag catcaggcag aatgaatggc agagagtgat tctgtcttca   1680

tagagggtgg ggtacttctc cataaggcat ctcagtcaaa tccccatcac tgtcat       1736


<210> SEQ ID NO 12
<211> LENGTH: 179
<212> TYPE: PRT
<213> ORGANISM: Homo sapiens

<400> SEQUENCE: 12

Met Ala Lys Gly Pro Ala Lys Asn Ser Glu Pro Glu Glu Val Ile Pro
1               5                   10                  15

Ser Arg Leu Asp Ile Arg Val Gly Lys Ile Ile Thr Val Glu Lys His
            20                  25                  30

Pro Asp Ala Asp Ser Leu Tyr Val Glu Lys Ile Asp Val Gly Glu Ala
        35                  40                  45

Glu Pro Arg Thr Val Val Ser Gly Leu Val Gln Phe Val Pro Lys Glu
    50                  55                  60

Glu Leu Gln Asp Arg Leu Val Val Val Leu Cys Asn Leu Lys Pro Gln
65                  70                  75                  80

Lys Met Arg Gly Val Glu Ser Gln Gly Met Leu Leu Cys Ala Ser Ile
                85                  90                  95

Glu Gly Ile Asn Arg Gln Val Glu Pro Leu Asp Pro Pro Ala Gly Ser
            100                 105                 110

Ala Pro Gly Glu His Val Phe Val Lys Gly Tyr Glu Lys Gly Gln Pro
        115                 120                 125

Asp Glu Glu Leu Lys Pro Lys Lys Lys Val Phe Glu Lys Leu Gln Ala
    130                 135                 140

Asp Phe Lys Ile Ser Glu Glu Cys Ile Ala Gln Trp Lys Gln Thr Asn
145                 150                 155                 160

Phe Met Thr Lys Leu Gly Ser Ile Ser Cys Lys Ser Leu Lys Gly Gly
                165                 170                 175

Asn Ile Ser


<210> SEQ ID NO 13
<211> LENGTH: 1167
<212> TYPE: DNA
<213> ORGANISM: Homo sapiens

<400> SEQUENCE: 13

atgggggacg ctcccagccc tgaagagaaa ctgcacctta tcacccggaa cctgcaggag     60

gttctggggg aagagaagct gaaggagata ctgaaggagc gggaacttaa aatttactgg    120

ggaacggcaa ccacgggcaa accacatgtg gcttactttg tgcccatgtc aaagattgca    180

gacttcttaa aggcagggtg tgaggtaaca attctgtttg cggacctcca cgcatacctg    240

gataacatga aagccccatg ggaacttcta gaactccgag tcagttacta tgagaatgtg    300
```

```
atcaaagcaa tgctggagag cattggtgtg cccttggaga agctcaagtt catcaaaggc    360

actgattacc agctcagcaa agagtacaca ctagatgtgt acagactctc ctccgtggtc    420

acacagcacg attccaagaa ggctggagct gaggtggtaa agcaggtgga gcaccctttg    480

ctgagtggcc tcttataccc cggactgcag gctttggatg aagagtattt aaaagtagat    540

gcccaatttg gaggcattga tcagagaaag attttcacct ttgcagagaa gtacctccct    600

gcacttggct attcaaaacg ggtccatctg atgaatccta tggttccagg attaacaggc    660

agcaaaatga gctcttcaga agaggagtcc aagattgatc tccttgatcg gaaggaggat    720

gtgaagaaaa aactgaagaa ggccttctgt gagccaggaa atgtggagaa caatggggtt    780

ctgtccttca tcaagcatgt cctttttccc cttaagtccg agtttgtgat cctacgagat    840

gagaaatggg gtggaaacaa aacctacaca gcttacgtgg acctggaaaa ggactttgct    900

gctgaggttg tacatcctgg agacctgaag aattctgttg aagtcgcact gaacaagttg    960

ctggatccaa tccgggaaaa gtttaatacc cctgccctga aaaaactggc cagcgctgcc   1020

tacccagatc cctcaaagca gaagccaatg gccaaaggcc tgccaagaat tcagaaccag   1080

aggaggtcat cccatcccgg ctggatatcc gtgtggggaa aatcatcact gtggagaagc   1140

acccagatgc agacagcctg tatgtag                                       1167


<210> SEQ ID NO 14
<211> LENGTH: 188
<212> TYPE: PRT
<213> ORGANISM: Homo sapiens
<220> FEATURE:
<221> NAME/KEY: VARIANT
<222> LOCATION: (1)..(8)
<223> OTHER INFORMATION: Xaa = Any Amino Acid

<400> SEQUENCE: 14

Xaa Xaa Xaa Xaa Xaa Xaa Xaa Xaa Pro Met Ala Lys Gly Pro Ala Lys
1               5                   10                  15

Asn Ser Glu Pro Glu Glu Val Ile Pro Ser Arg Leu Asp Ile Arg Val
            20                  25                  30

Gly Lys Ile Ile Thr Val Glu Lys His Pro Asp Ala Asp Ser Leu Tyr
        35                  40                  45

Val Glu Lys Ile Asp Val Gly Glu Ala Glu Pro Arg Thr Val Val Ser
    50                  55                  60

Gly Leu Val Gln Phe Val Pro Lys Glu Glu Leu Gln Asp Arg Leu Val
65                  70                  75                  80

Val Val Leu Cys Asn Leu Lys Pro Gln Lys Met Arg Gly Val Glu Ser
                85                  90                  95

Gln Gly Met Leu Leu Cys Ala Ser Ile Glu Gly Ile Asn Arg Gln Val
            100                 105                 110

Glu Pro Leu Asp Pro Pro Ala Gly Ser Ala Pro Gly Glu His Val Phe
        115                 120                 125

Val Lys Gly Tyr Glu Lys Gly Gln Pro Asp Glu Glu Leu Lys Pro Lys
    130                 135                 140

Lys Lys Val Phe Glu Lys Leu Gln Ala Asp Phe Lys Ile Ser Glu Glu
145                 150                 155                 160

Cys Ile Ala Gln Trp Lys Gln Thr Asn Phe Met Thr Lys Leu Gly Ser
                165                 170                 175

Ile Ser Cys Lys Ser Leu Lys Gly Gly Asn Ile Ser
            180                 185
```

<210> SEQ ID NO 15
<211> LENGTH: 2262
<212> TYPE: DNA
<213> ORGANISM: Homo sapiens

<400> SEQUENCE: 15

```
gccagacaca gtggctcaca cctgtaatct taacactttg gaaggctgag gcaggcggat     60
cacttgagcc caaaagttag agaccaaaac ccagtctcta cccaaaaaaa aaaaaaaaaa    120
aaaaattagc caggcatagt agcacatgcc tgtagtccca gctacttggg aggctgaggt    180
gagaggatca cctgagcatg ggaagttgga gactgcagtg agccatgatc gcaccactgc    240
actccagcct gggcaacaga gtgagactct atgtctcaaa aaaagaaaaa tgatagaaat    300
tagattagac ctattatacc caaccggtat atagggtatc gatagtttct tacacagctg    360
ttgggcagag cctgcagagc ttagagaagc ttatctttag attctcccag tttccttcta    420
tgtgcatggg cctggctctt agttggccat ccacttgtgc gtaatgctaa gatattggca    480
ttgatagctt tgtgcgaccc ttccagaaaa aaactcagta actcagtaaa attttttttt    540
tttttctaa aagagacaga gtctggctct gttgcccagc ctggtcttga agtcctgggc    600
ttaagcaatc ctcccgtctc agcctcccaa agtgctagaa ttacaggtgt gagctaccac    660
acctggccaa gactcagtaa attctatgtg gaatgcatga atggaaatac ctaaaggagg    720
caaagctact actgctccct ccccgctagt ctaataattg agggagagaa cagatgaaaa    780
tcaggtatgt catgtctgaa aggttgccaa cccagtatta aagaagttac aactcagtgt    840
ttagactctg gggattctac actaaatctt acctaatctc agtgtcttaa cgtggtggga    900
tcagcagctg acctgccaca gggaagaatt ctacctcatg gggttcttct cattcccaga    960
gccaatggcc aaaggccctg ccaagaattc agaaccagag gaggtcatcc catcccggct   1020
ggatatccgt gtggggaaaa tcatcactgt ggagaagcac ccagatgcag acagcctgta   1080
tgtagagaag attgacgtgg gggaagctga accacggact gtggtgagcg gcctggtaca   1140
gttcgtgccc aaggaggaac tgcaggacag gctggtagtg gtgctgtgca acctgaaacc   1200
ccagaagatg agaggagtcg agtcccaagg catgcttctg tgtgcttcta tagaagggat   1260
aaaccgccag gttgaacctc tggaccctcc ggcaggctct gctcctggtg agcacgtgtt   1320
tgtgaagggc tatgaaaagg gccaaccaga tgaggagctc aagcccaaga agaaagtctt   1380
cgagaagttg caggctgact tcaaaatttc tgaggagtgc atcgcacagt ggaagcaaac   1440
caacttcatg accaagctgg gctccatttc ctgtaaatcg ctgaaagggg ggaacattag   1500
ctagccagcc cagcatcttc ccccttctt ccaccactga gtcatctgct gtctcttcag   1560
tctgctccat ccatcaccca tttacccatc tctcaggaca cggaagcagc gggtttggac   1620
tctttattcg gtgcagaact cggcaagggg cagcttaccc tccccagaac ccaggatcat   1680
cctgtctggc tgcagtgaga gaccaacccc taacaagggc tgggccacag cagggagtcc   1740
agccctacct tcttcccttg gcagctggag aaatctggtt tcaatataac tcatttaaaa   1800
atttatgcca cagtccttat aattggaaaa atactggtgc ccaggttttc ttggagttat   1860
ccaagcagct gcgcccctag ctgggatctg gtacctggac taggctaatt acagcttctc   1920
cccaacagga aactgtggga tttgaaaagg aaagggaagg gaaaacagag aacctagtgg   1980
tctaccaagt ggttggcaac tttcccaatg tctgcttact ctgaggcttg gcactggggg   2040
ccagggcctg ccccagggct cctggaattt cccttgatcc agctaggctg ggacactccc   2100
taaatcagct gcgtgttgtt agcatcaggc agaatgaatg gcagagagtg attctgtctt   2160
```

-continued

| | |
|---|---|
| catagagggt ggggtacttc tccataaggc atctcagtca aatccccatc actgtcataa | 2220 |
| attcaaataa aatgtctgaa caagggaaaa aaaaaaaaaa aa | 2262 |